(12) United States Patent
Ohashi et al.

(10) Patent No.: US 9,366,958 B2
(45) Date of Patent: Jun. 14, 2016

(54) PHOTOACID GENERATOR, CHEMICALLY AMPLIFIED RESIST COMPOSITION, AND PATTERNING PROCESS

(71) Applicant: Shin-Etsu Chemical Co., Ltd., Tokyo (JP)

(72) Inventors: Masaki Ohashi, Joetsu (JP); Masahiro Fukushima, Joetsu (JP)

(73) Assignee: SHIN-ETSU CHEMICAL CO., LTD., TOKYO (JP)

( * ) Notice: Subject to any disclaimer, the term of this patent is extended or adjusted under 35 U.S.C. 154(b) by 0 days.

(21) Appl. No.: 14/685,895

(22) Filed: Apr. 14, 2015

(65) Prior Publication Data

US 2015/0301449 A1    Oct. 22, 2015

(30) Foreign Application Priority Data

Apr. 22, 2014 (JP) ................................. 2014-088137

(51) Int. Cl.

| | |
|---|---|
| *G03F 7/004* | (2006.01) |
| *C07C 381/12* | (2006.01) |
| *C07C 309/17* | (2006.01) |
| *G03F 7/027* | (2006.01) |
| *G03F 7/20* | (2006.01) |
| *C07D 333/46* | (2006.01) |
| *G03F 7/038* | (2006.01) |

(Continued)

(52) U.S. Cl.
CPC .............. *G03F 7/027* (2013.01); *C07C 309/12* (2013.01); *C07C 309/73* (2013.01); *C07C 381/12* (2013.01); *C07D 333/46* (2013.01); *G03F 7/038* (2013.01); *G03F 7/20* (2013.01); *G03F 7/2041* (2013.01); *H01L 21/0274* (2013.01); *C07C 2103/74* (2013.01); *G03F 7/32* (2013.01)

(58) Field of Classification Search
CPC ....... G03F 7/004; G03F 7/2041; G03F 7/038; G03F 7/32; H01L 21/0274; H01L 21/0276; C07C 381/12; C07C 309/12; C07C 309/73; C07D 333/46; C07D 307/64
USPC .............. 430/270.1, 913, 914, 434, 942, 322; 560/14, 114, 116, 151
See application file for complete search history.

(56) References Cited

U.S. PATENT DOCUMENTS

| | | | |
|---|---|---|---|
| 5,650,483 | A | 7/1997 | Malik et al. |
| 6,037,098 | A | 3/2000 | Aoai et al. |

(Continued)

FOREIGN PATENT DOCUMENTS

| | | |
|---|---|---|
| JP | 3773139 B2 | 5/2006 |
| JP | 3790649 B2 | 6/2006 |

(Continued)

OTHER PUBLICATIONS

Dammel et al., "193 nm Immersion Lithography—Taking the Plunge", Journal of Photopolymer Science and Technology, 2004, pp. 587-601, vol. 17, No. 4, cited in the Specification.

(Continued)

*Primary Examiner* — Amanda C Walke
(74) *Attorney, Agent, or Firm* — Westerman, Hattori, Daniels & Adrian, LLP

(57) ABSTRACT

An onium salt having an anion moiety of a specific bissulfonate structure is an effective photoacid generator. A resist composition comprising the PAG forms a pattern with a good balance of sensitivity and MEF, and minimal defects and offers a precise micropatterning resist material.

11 Claims, 12 Drawing Sheets

(51) Int. Cl.
 *H01L 21/027* (2006.01)
 *C07C 309/12* (2006.01)
 *C07C 309/73* (2006.01)
 *G03F 7/32* (2006.01)

(56) References Cited

U.S. PATENT DOCUMENTS

| | | | |
|---|---|---|---|
| 6,316,500 | B1 | 11/2001 | Elder et al. |
| 7,511,169 | B2 | 3/2009 | Ohsawa et al. |
| 7,527,912 | B2 | 5/2009 | Ohsawa et al. |
| 7,537,880 | B2 | 5/2009 | Harada et al. |
| 7,556,909 | B2 | 7/2009 | Kobayashi et al. |
| 7,622,242 | B2 | 11/2009 | Hatakeyama et al. |
| 7,771,914 | B2 | 8/2010 | Hatakeyama et al. |
| 7,858,289 | B2 | 12/2010 | Yamashita |
| 7,919,226 | B2 | 4/2011 | Ohsawa et al. |
| 8,034,547 | B2 | 10/2011 | Tsubaki et al. |
| 8,057,981 | B2 | 11/2011 | Harada et al. |
| 8,057,985 | B2 | 11/2011 | Ohashi et al. |
| 8,101,335 | B2 | 1/2012 | Harada et al. |
| 8,114,570 | B2 | 2/2012 | Ohsawa et al. |
| 8,114,571 | B2 | 2/2012 | Ohashi et al. |
| 8,173,354 | B2 | 5/2012 | Ohsawa et al. |
| 8,227,183 | B2 | 7/2012 | Tsubaki et al. |
| 8,241,840 | B2 | 8/2012 | Tsubaki et al. |
| 8,252,504 | B2 | 8/2012 | Harada et al. |
| 8,268,528 | B2 | 9/2012 | Harada et al. |
| 8,283,104 | B2 | 10/2012 | Ohashi et al. |
| 8,313,886 | B2 | 11/2012 | Harada et al. |
| 8,394,570 | B2 | 3/2013 | Ohashi et al. |
| 8,431,323 | B2 | 4/2013 | Watanabe et al. |
| 8,435,717 | B2 | 5/2013 | Hagiwara et al. |
| 8,530,148 | B2 | 9/2013 | Tsubaki et al. |
| 8,535,869 | B2 | 9/2013 | Ohsawa et al. |
| 8,580,478 | B2 * | 11/2013 | Yamato ................ C07C 271/24 430/270.1 |
| 8,597,869 | B2 | 12/2013 | Sagehashi et al. |
| 8,795,942 | B2 | 8/2014 | Kobayashi et al. |
| 2006/0220339 | A1 | 10/2006 | Kusaka et al. |
| 2008/0044738 | A1 | 2/2008 | Harada et al. |
| 2008/0090172 | A1 | 4/2008 | Hatakeyama et al. |
| 2010/0099042 | A1 | 4/2010 | Ohashi et al. |
| 2010/0209827 | A1 | 8/2010 | Ohashi et al. |
| 2012/0129103 | A1 | 5/2012 | Ohsawa et al. |
| 2013/0337378 | A1 | 12/2013 | Ohashi et al. |
| 2014/0005301 | A1 * | 1/2014 | Kunimoto ............ C07D 307/10 523/400 |
| 2015/0044509 | A1 * | 2/2015 | Kunimoto ............. C09D 11/02 428/704 |

FOREIGN PATENT DOCUMENTS

| | | |
|---|---|---|
| JP | 2006-281975 A | 10/2006 |
| JP | 2007-145797 A | 6/2007 |
| JP | 2007-145804 A | 6/2007 |
| JP | 3991462 B2 | 10/2007 |
| JP | 2008-13551 A | 1/2008 |
| JP | 2008-106045 A | 5/2008 |
| JP | 2008-111103 A | 5/2008 |
| JP | 2008-122932 A | 5/2008 |
| JP | 2008-158339 A | 7/2008 |
| JP | 2008-281974 A | 11/2008 |
| JP | 2009-7327 A | 1/2009 |
| JP | 2009-98638 A | 5/2009 |
| JP | 2009-109595 A | 5/2009 |
| JP | 2009-191151 A | 8/2009 |
| JP | 2009-192784 A | 8/2009 |
| JP | 2009-258695 A | 11/2009 |
| JP | 2009-269953 A | 11/2009 |
| JP | 2009-276363 A | 11/2009 |
| JP | 2010-77404 A | 4/2010 |
| JP | 2010-107695 A | 5/2010 |
| JP | 2010-116550 A | 5/2010 |
| JP | 2010-134012 A | 6/2010 |
| JP | 2010-155824 A | 7/2010 |
| JP | 2010-215608 A | 9/2010 |
| JP | 4554665 B2 | 9/2010 |
| JP | 2010-250105 A | 11/2010 |
| JP | 2011-16746 A | 1/2011 |
| JP | 201142789 A | 3/2011 |
| JP | 2012-41320 A | 3/2012 |
| JP | 2012-46501 A | 3/2012 |
| JP | 2012-106986 A | 6/2012 |
| JP | 2012-107151 A | 6/2012 |
| JP | 2012-153644 A | 8/2012 |
| JP | 201404769 A | 2/2014 |
| WO | 2011/048919 A1 | 4/2011 |

OTHER PUBLICATIONS

Dffice Action dated Apr. 18, 2016, issued in counterpart Taiwanese Application no. 104112507 (5 pages).

* cited by examiner

PHOTOACID GENERATOR, CHEMICALLY AMPLIFIED RESIST COMPOSITION, AND PATTERNING PROCESS

CROSS-REFERENCE TO RELATED APPLICATION

This non-provisional application claims priority under 35 U.S.C. §119(a) on Patent Application No. 2014-088137 filed in Japan on Apr. 22, 2014, the entire contents of which are hereby incorporated by reference.

TECHNICAL FIELD

This invention relates to a photoacid generator of specific structure, a chemically amplified resist composition comprising the photoacid generator, and a patterning process using the resist composition.

BACKGROUND ART

While a number of recent efforts are being made to achieve a finer pattern rule in the drive for higher integration and operating speeds in LSI devices, DUV and EUV lithography processes are thought to hold particular promise as the next generation in microfabrication technology. In particular, photolithography using an ArF excimer laser as the light source is requisite to the micropatterning technique capable of achieving a feature size of 0.13 µm or less.

The ArF lithography started partial use from the fabrication of 130-nm node devices and became the main lithography since 90-nm node devices. Although lithography using $F_2$ laser (157 nm) was initially thought promising as the next lithography for 45-nm node devices, its development was retarded by several problems. A highlight was suddenly placed on the ArF immersion lithography that introduces a liquid having a higher refractive index than air (e.g., water, ethylene glycol, glycerol) between the projection lens and the wafer, allowing the projection lens to be designed to a numerical aperture (NA) of 1.0 or higher and achieving a higher resolution. See Non-Patent Document 1. The ArF immersion lithography is now implemented on the commercial stage. The immersion lithography requires a resist material which is substantially insoluble in water.

In the photolithography using an ArF excimer laser (wavelength 193 nm), a high sensitivity resist material capable of achieving a high resolution at a small dose of exposure is needed to prevent the degradation of precise and expensive optical system materials. Among several measures for providing high sensitivity resist material, the most common is to select each component which is highly transparent at the wavelength of 193 nm. For example, polymers of acrylic acid and derivatives thereof, norbornene-maleic anhydride alternating copolymers, polynorbornene, ring-opening metathesis polymerization (ROMP) polymers, and hydrogenated ROMP polymers have been proposed as the base resin. This choice is effective to some extent in that the transparency of a resin alone is increased.

Recently a highlight is put on the negative tone resist adapted for organic solvent development as well as the positive tone resist adapted for alkaline development. It would be desirable if a very fine hole pattern, which is not achievable with the positive tone, is resolvable through negative tone exposure. To this end, a positive resist material featuring a high resolution is subjected to organic solvent development to form a negative pattern. An attempt to double a resolution by combining two developments, alkali development and organic solvent development is under study.

As the ArF resist material for negative tone development with organic solvent, positive ArF resist compositions of the prior art design may be used. Such pattern forming processes are described in Patent Documents 1 to 3.

To meet the current rapid progress of microfabrication technology, development efforts are put on not only the process, but also the resist material. Studies have also been made on photoacid generators (PAGs). Commonly used are sulfonium salts of triphenylsulfonium cation with perfluoroalkanesulfonic acid anion. These salts generate perfluoroalkanesulfonic acids, especially perfluorooctanesulfonic acid (PFOS), which are considered problematic with respect to their non-degradability, biological concentration and toxicity. It is rather restricted to apply these salts to the resist material. Instead, PAGs capable of generating perfluorobutanesulfonic acid are currently used, but are awkward to achieve a high resolution because of substantial diffusion of the generated acid in the resist material. To address the problem, partially fluorinated alkane sulfonic acids and salts thereof are developed. For instance, Patent Document 1 refers to the prior art PAGs capable of generating $\alpha,\alpha$-difluoroalkanesulfonic acid, such as di(4-tert-butylphenyl)iodonium 1,1-difluoro-2-(1-naphthyl)ethanesulfonate and PAGs capable of generating $\alpha,\alpha,\beta,\beta$-tetrafluoroalkanesulfonic acid. Despite a reduced degree of fluorine substitution, these PAGs still have the following problems. Since they do not have a decomposable substituent group such as ester structure, they are unsatisfactory from the aspect of environmental safety due to ease of decomposition. The molecular design to change the size of alkanesulfonic acid is limited. Fluorine-containing starting reactants are expensive.

As the circuit line width is reduced, the degradation of contrast by acid diffusion becomes more serious for the resist material. The reason is that the pattern feature size is approaching the diffusion length of acid. This invites a lowering of mask fidelity and a degradation of pattern rectangularity because a dimensional shift on wafer (known as mask error factor (MEF)) relative to a dimensional shift on mask is exaggerated. Accordingly, to gain more benefits from a reduction of exposure light wavelength and an increase of lens NA, the resist material is required to increase a dissolution contrast or restrain acid diffusion, as compared with the prior art materials. One approach is to lower the bake temperature for suppressing acid diffusion and hence, improving MEF. A low bake temperature, however, inevitably leads to a low sensitivity.

Incorporating a bulky substituent or polar group into PAG is effective for suppressing acid diffusion. Patent Document 4 describes a PAG having 2-acyloxy-1,1,3,3,3-pentafluoropropane-1-sulfonic acid which is fully soluble and stable in resist solvents and allows for a wide span of molecular design. In particular, a PAG having incorporated therein a bulky substituent, 2-(1-adamantyloxy)-1,1,3,3,3-pentafluoropropane-1-sulfonic acid is characterized by slow acid diffusion. A resist composition comprising this PAG, however, is still insufficient in precise control of acid diffusion, and its lithography performance is unsatisfactory when evaluated totally in terms of MEF, pattern profile and sensitivity.

Patent Document 5 discloses a PAG having bissulfonium cation. Patent Documents 6 and 7 disclose PAGs having bissulfonate anion. Because of their low solvent solubility, these bis-sulfonium salts are limited in addition amount and undesirably cause defects to be described below.

As resist patterns with high resolution are currently required, not only lithography characteristics including pattern profile, contrast, MEEF and roughness are necessary, but improvements in (surface) defects of resist patterns as developed become more requisite. The surface defects refer to all faults which are detected when the resist pattern as developed is observed from just above by a surface flaw detector (trade name KLA by KLA-Tencor Co., Ltd.). Such faults include scum, foam, debris, and bridges between resist pattern features after development. These defects form because PAG or other resist components have low solubility in casting solvent and leave undissolved residues after developer immersion.

CITATION LIST

Patent Document 1: JP-A 2008-281974
Patent Document 2: JP-A 2008-281975
Patent Document 3: JP 4554665
Patent Document 4: JP-A 2007-145797
Patent Document 5: JP 3773139
Patent Document 6: JP-A 2008-013551
Patent Document 7: WO 2011/048919
Non-Patent Document 1: Journal of Photopolymer Science and Technology, Vol. 17, No. 4, p 587 (2004)

DISCLOSURE OF THE INVENTION

The photoacid generator (PAG) produces an acid which must satisfy many requirements including a sufficient acid strength to cleave acid labile groups in a resist material, high sensitivity, stability in the resist material during shelf storage, adequately controlled diffusion in the resist material, low volatility, minimal foreign matter left after development and resist removal, and good degradability in that it is decomposed away after the expiration of its role in lithography without imposing a load to the environment. In the case of ArF immersion lithography, minimal dissolution in water is also desirable. No resist compositions using prior art PAGs satisfy these requirements.

An object of the invention is to provide a photoacid generator, a chemically amplified resist composition comprising the photoacid generator, and a patterning process using the resist composition, wherein the composition forms a pattern with a good balance of sensitivity and MEF, rectangular profile, and minimal defects when processed by photolithography using high-energy radiation such as ArF excimer laser, EB or EUV as light source.

The inventors have found that a resist composition comprising a photoacid generator in the form of an onium salt having a specific structure forms a pattern with a good balance of sensitivity and MEF, and minimal defects and is thus a quite effective resist material for precise micropatterning.

In one aspect, the invention provides a photoacid generator having the general formula (1a).

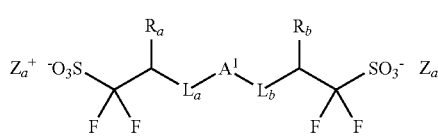

(1a)

Herein $A^1$ is a straight, branched or cyclic $C_1$-$C_{30}$ divalent hydrocarbon group which may be substituted with or separated by a heteroatom, $L_a$ and $L_b$ are each independently a linking group selected from ether bond, ester bond, sulfonic acid ester bond, carbonate bond, and carbamate bond, $R_a$ and $R_b$ are each independently hydrogen or trifluoromethyl, $Z_a^+$ and $Z_b^+$ are each independently a sulfonium or iodonium cation.

The preferred photoacid generator has the structure of the general formula (1b).

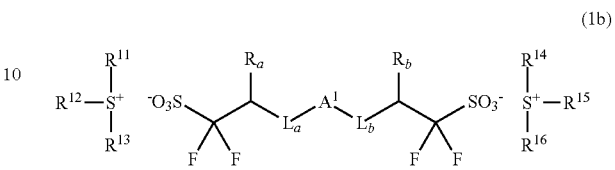

(1b)

Herein $A^1$, $L_a$, $L_b$, $R_a$ and $R_b$ are as defined above, $R^{11}$, $R^{12}$, $R^{13}$, $R^{14}$, $R^{15}$, and $R^{16}$ are each independently a straight, branched or cyclic $C_1$-$C_{10}$ alkyl or alkenyl group which may be substituted with or separated by a heteroatom, or a $C_6$-$C_{18}$ aryl or aralkyl group which may be substituted with or separated by a heteroatom, any two of $R^{11}$, $R^{12}$ and $R^{13}$ or any two of $R^{14}$, $R^{15}$ and $R^{16}$ may bond together to form a ring with the adjacent sulfur atom.

In another aspect, the invention provides a chemically amplified resist composition comprising a base resin, the photoacid generator defined above, and an organic solvent.

In a preferred embodiment, the base resin is a polymer comprising recurring units having the general formula (2) and recurring units having the general formula (3).

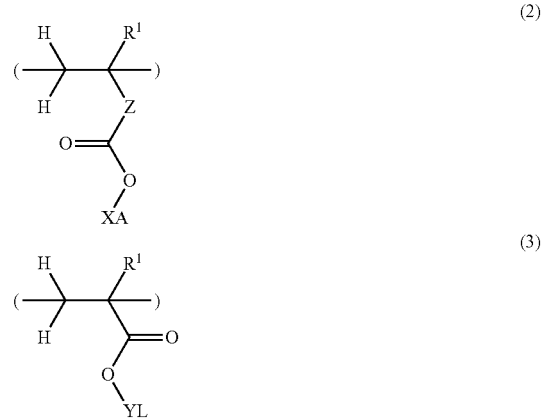

Herein $R^1$ is hydrogen, fluorine, methyl or trifluoromethyl, Z is a single bond, phenylene group, naphthylene group or (backbone)-C(=O)—O—Z'—, Z' is a straight, branched or cyclic $C_1$-$C_{10}$ alkylene group which may contain a hydroxyl radical, ether bond, ester bond or lactone ring, or phenylene group or naphthylene group, XA is an acid labile group, and YL is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

The resist composition may further comprise a photoacid generator other than the photoacid generator defined above, a quencher, a surfactant which is insoluble or substantially insoluble in water and soluble in alkaline developer, and a surfactant which is insoluble or substantially insoluble in water and alkaline developer.

In a further aspect, the invention provides a pattern forming process comprising the steps of applying the chemically amplified resist composition defined above onto a substrate to form a coating, baking, exposing the coating to high-energy radiation, and developing the exposed coating in a developer.

Preferably, the exposure step is carried out by immersion lithography using a liquid having a refractive index of at least 1.0 between the resist coating and a projection lens. More preferably, a protective film is coated on the resist coating prior to the exposure step, wherein immersion lithography is carried out while the liquid is held between the protective film and the projection lens. The high-energy radiation is typically KrF excimer laser, ArF excimer laser, electron beam or soft X-ray having a wavelength of 3 to 15 nm.

Advantageous Effects of Invention

A resist composition comprising the inventive photoacid generator, when processed by lithography, forms a pattern with a good balance of sensitivity and MEF and minimal defects. It is thus a quite effective resist material for precise micropatterning.

DESCRIPTION OF THE PREFERRED EMBODIMENTS

Figure 1:
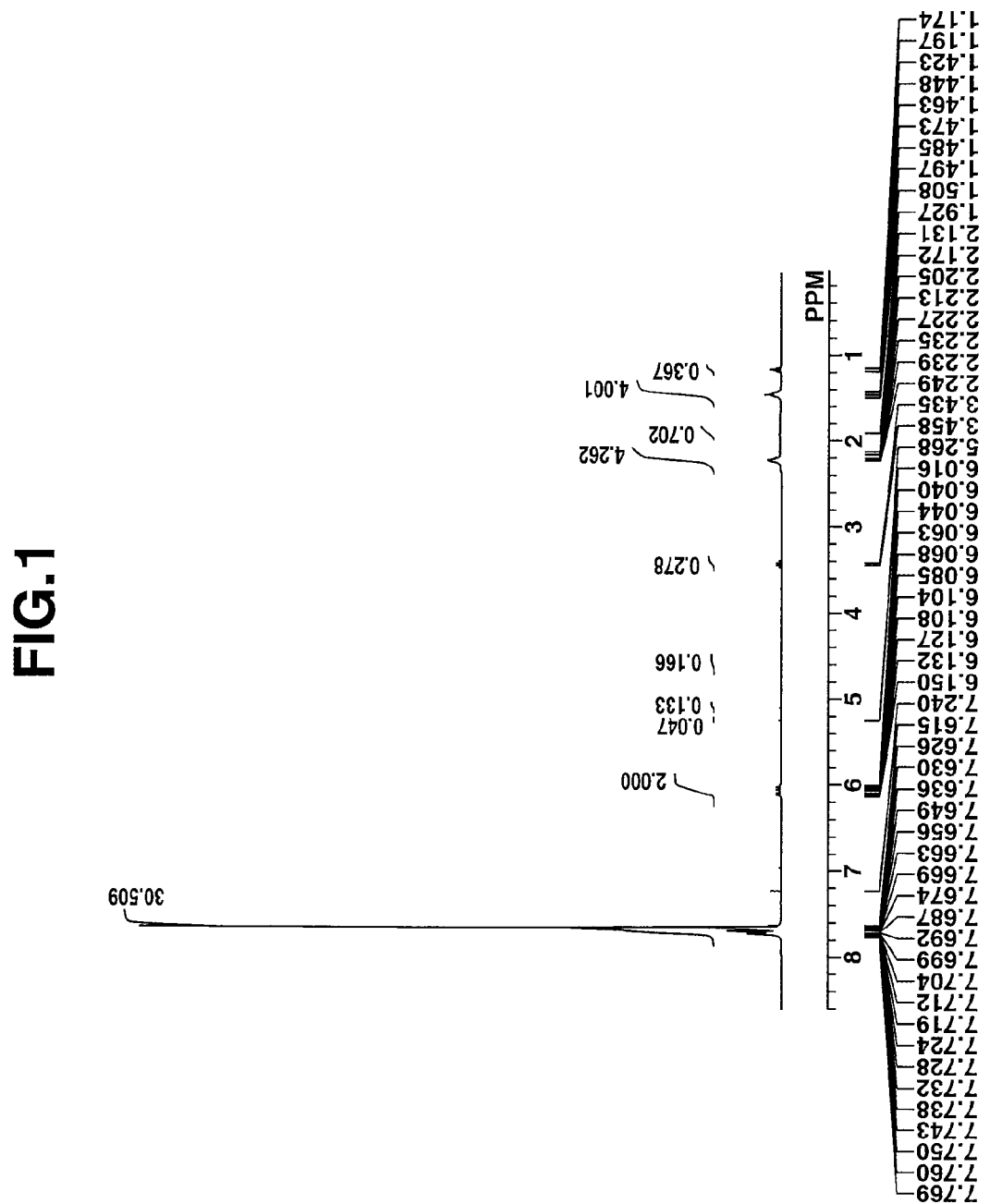
FIG. 1 is a diagram showing the $^1$H-NMR/DMSO-$d_6$ spectrum of PAG-1 in Synthesis Example 1-1.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. In chemical formulae, the broken line denotes a valence bond. Ac stands for acetyl, and Ph for phenyl.

The abbreviations have the following meaning.
EB: electron beam
UV: ultraviolet
EUV: extreme ultraviolet
PAG: photoacid generator
PEB: post-exposure bake
MEF: mask error factor The term "high-energy radiation" is intended to encompass KrF excimer laser, ArF excimer laser, EB, and soft x-ray.

Photoacid Generator

The invention provides a photoacid generator having the general formula (1a).

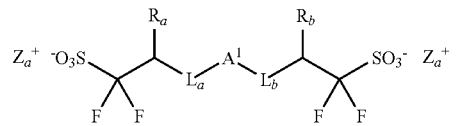

(1a)

Herein $A^1$ is a straight, branched or cyclic $C_1$-$C_{30}$ divalent hydrocarbon group which may be substituted with or separated by a heteroatom, $L_a$ and $L_b$ are each independently a linking group selected from ether bond, ester bond, sulfonic acid ester bond, carbonate bond, and carbamate bond, $R_a$ and $R_b$ are each independently hydrogen or trifluoromethyl, $Z_a^+$ and $Z_b^+$ are each independently a sulfonium or iodonium cation.

In formula (1a), $A^1$ is a straight, branched or cyclic $C_1$-$C_{30}$ divalent hydrocarbon group which may be substituted with or separated by a heteroatom. Suitable divalent hydrocarbon groups include straight alkanediyl groups such as methylene, ethylene, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; divalent saturated cyclic hydrocarbon groups such as cyclopentanediyl, cyclohexanediyl, norbornanediyl, and adamantanediyl; and divalent unsaturated cyclic hydrocarbon groups such as phenylene and naphthylene. Also included are substituted forms of the foregoing groups in which one or more hydrogen atoms are substituted by an alkyl group(s) such as methyl, ethyl, propyl, n-butyl, or tert-butyl; and substituted forms of the foregoing groups in which one or more heteroatoms such as oxygen, sulfur, nitrogen, and halogen atom may replace to eventually form a hydroxyl, cyano, carbonyl, ether bond, ester bond, sulfonic acid ester bond, carbonate bond, lactone ring, sultone ring, carboxylic anhydride or haloalkyl group. Of these, unsubstituted alkylene groups are preferred because of availability of starting reactants.

$L_a$ and $L_b$ are each independently a linking group selected from ether bond, ester bond, sulfonic acid ester bond, carbonate bond, and carbamate bond, preferably ether bond (—O—) or ester bond (—COO—).

$R_a$ and $R_b$ are each independently hydrogen or trifluoromethyl. Most preferably both $R_a$ and $R_b$ are trifluoromethyl. The corresponding compounds are easy and inexpensive to synthesize as compared with those compounds wherein $R_a$ and $R_b$ are different, and improved in solubility as compared with those compounds wherein $R_a$ and $R_b$ are hydrogen. This is probably because the carbon atom to which trifluoromethyl is attached is asymmetric.

$Z_a^+$ and $Z_b^+$ are each independently a sulfonium cation or iodonium cation. Suitable iodonium cations include diphenyliodonium, bis(4-methylphenyl)iodonium, bis(4-ethylphenyl)iodonium, bis(4-tert-butylphenyl)iodonium, bis(4-(1,1-dimethylpropyl)phenyl)iodonium, 4-methoxyphenylphenyliodonium, 4-tert-butoxyphenylphenyliodonium, 4-acryloyloxyphenylphenyliodonium, and 4-methacryloyloxyphenylphenyliodonium, with bis(4-tert-butylphenyl)iodonium being preferred. The sulfonium cation will be described later.

Preferably, the photoacid generator of formula (1a) has the structure of the general formula (1b).

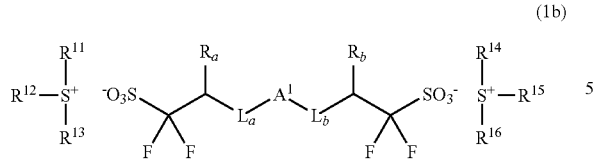
(1b)

Herein $A^1$, $L_a$, $L_b$, $R_a$ and $R_b$ are as defined above, $R^{11}$, $R^{12}$, $R^{13}$, $R^{14}$, $R^{15}$, and $R^{16}$ are each independently a straight, branched or cyclic $C_1$-$C_{10}$ alkyl or alkenyl group which may be substituted with or separated by a heteroatom, or a $C_6$-$C_{18}$ aryl or aralkyl group which may be substituted with or separated by a heteroatom, any two of $R^{11}$, $R^{12}$ and $R^{13}$ or any two of $R^{14}$, $R^{15}$ and $R^{16}$ may bond together to form a ring with the adjacent sulfur atom.

Suitable groups of $R^{11}$ to $R^{16}$ include alkyl groups such as methyl, ethyl, n-propyl, isopropyl, n-butyl, tert-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl and thienyl; and aralkyl groups such as benzyl, 1-phenylethyl and 2-phenylethyl, with the aryl groups being preferred. Also included are substituted forms of the foregoing groups in which one or more hydrogen atoms are substituted by a heteroatom(s) such as oxygen, sulfur, nitrogen, and halogen atom, or which may be separated by a heteroatom(s) such as oxygen, sulfur or nitrogen, so that a hydroxyl, cyano, carbonyl, ether bond, ester bond, sulfonic acid ester bond, carbonate bond, lactone ring, sultone ring, carboxylic anhydride or haloalkyl group may eventually form or intervene. When any two of $R^{11}$, $R^{12}$ and $R^{13}$ or any two of $R^{14}$, $R^{15}$ and $R^{16}$ bond together to form a ring with the adjacent sulfur atom, suitable rings are shown below.

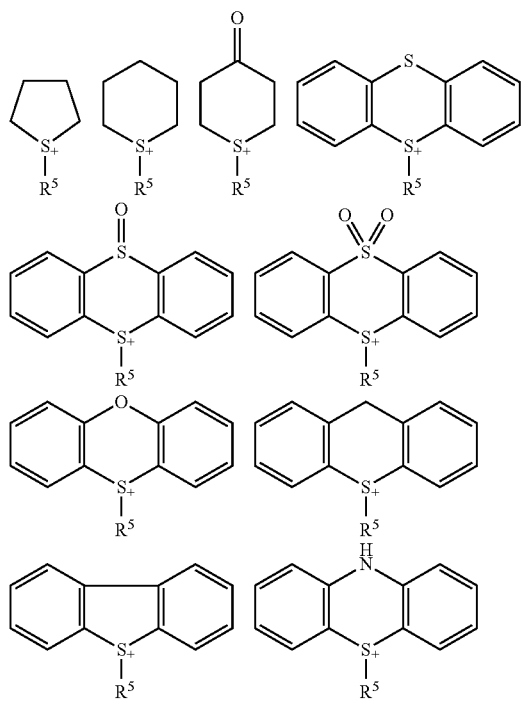

Herein $R^5$ is as defined and exemplified for $R^{11}$.

The cation moiety of the sulfonium salt having formula (1a) or (1b) is exemplified by the following structures, but not limited thereto.

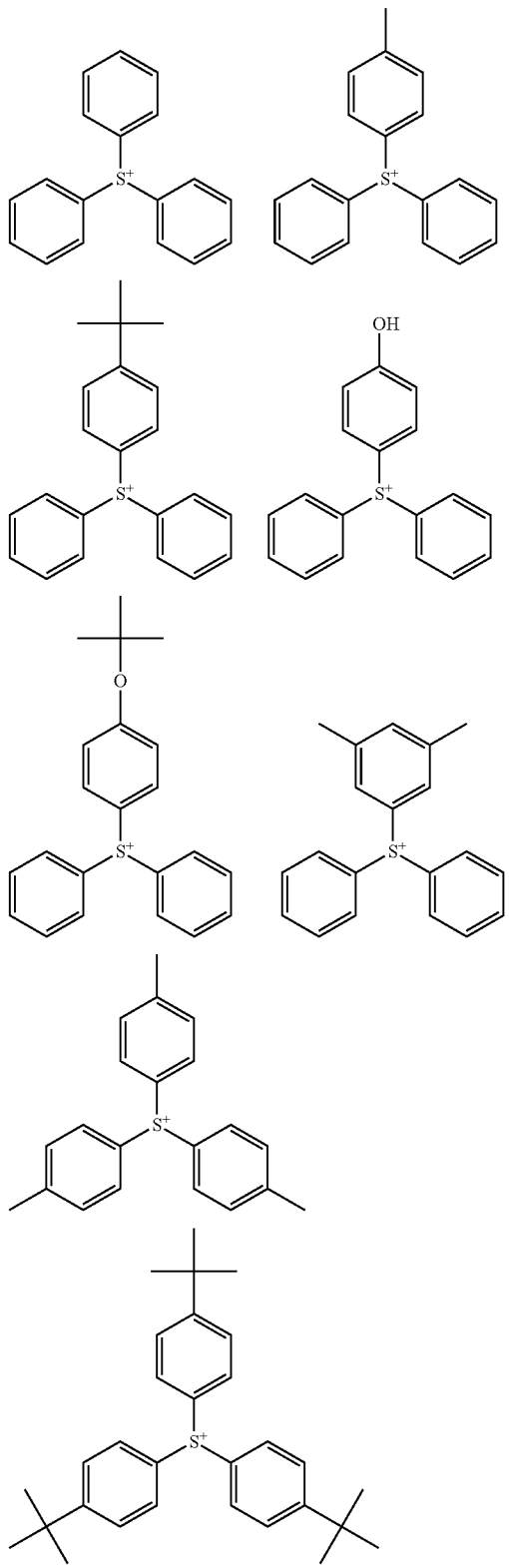

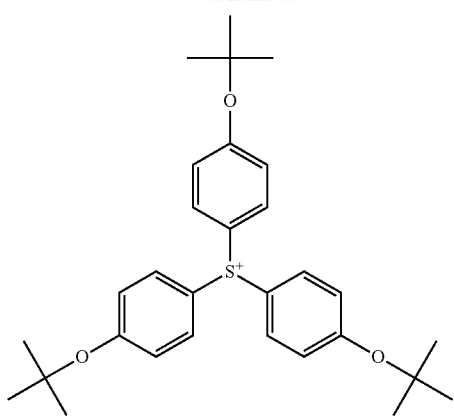
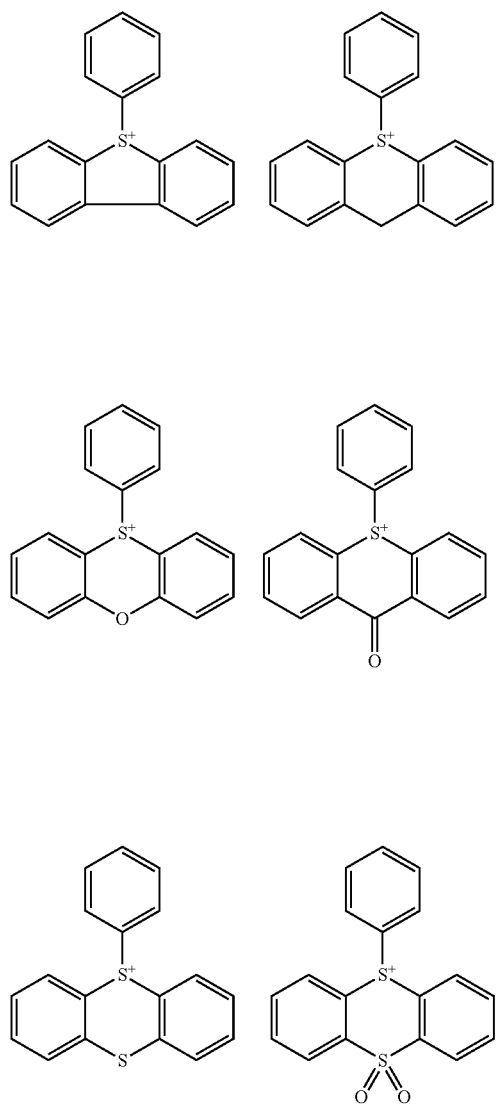
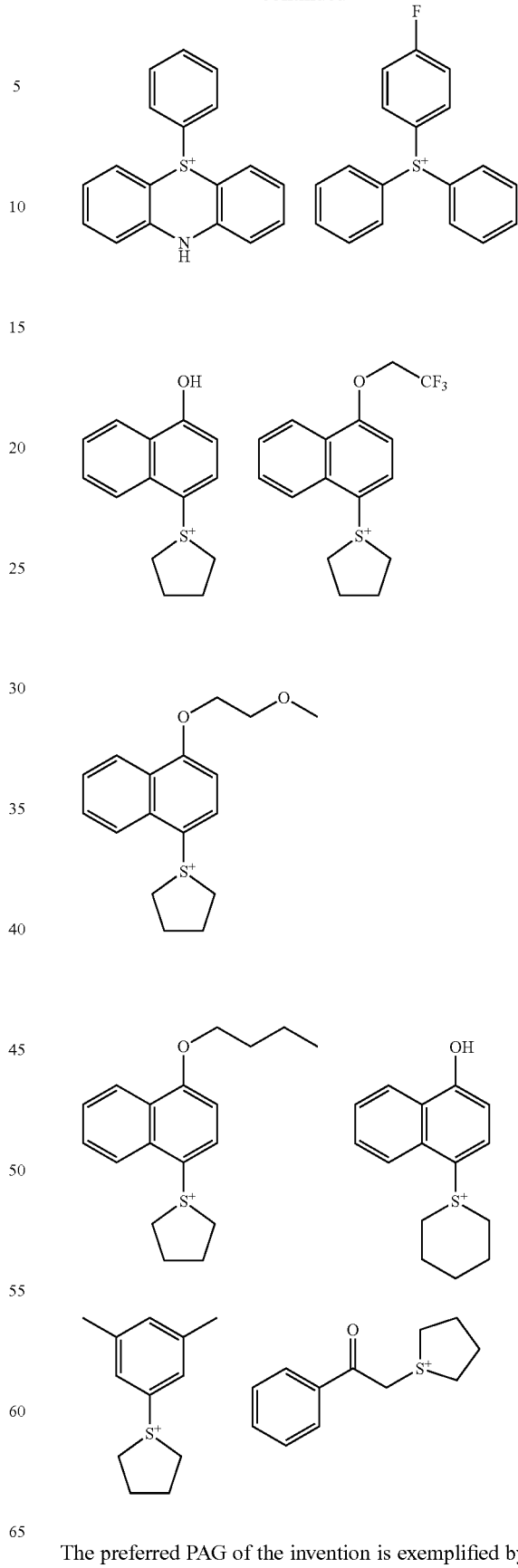
The preferred PAG of the invention is exemplified by the following structures, but not limited thereto.

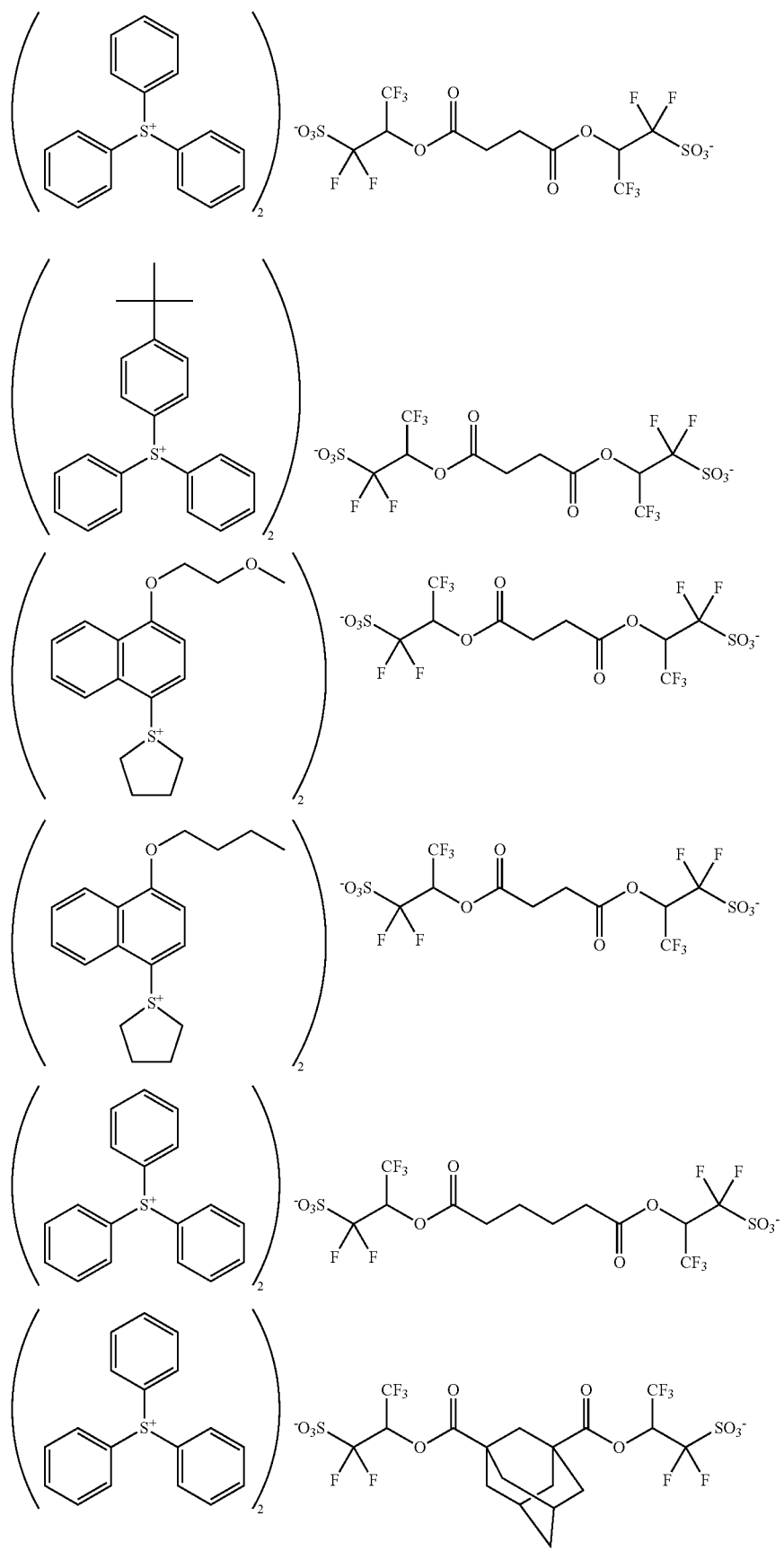

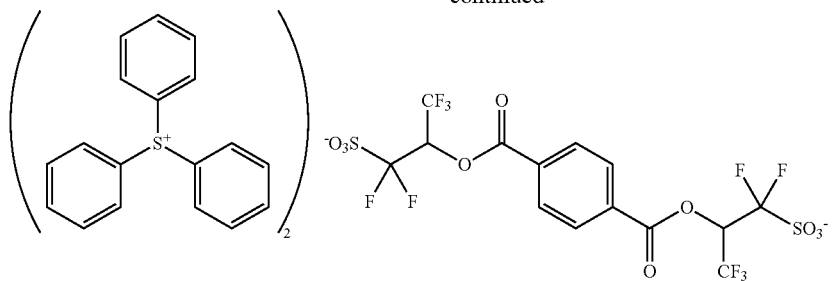
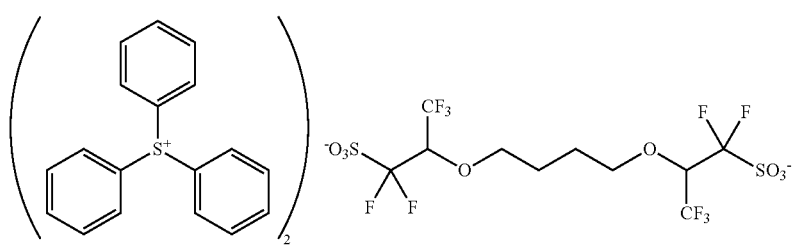
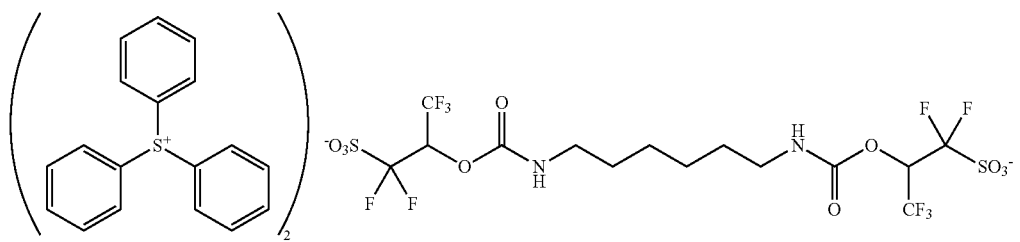
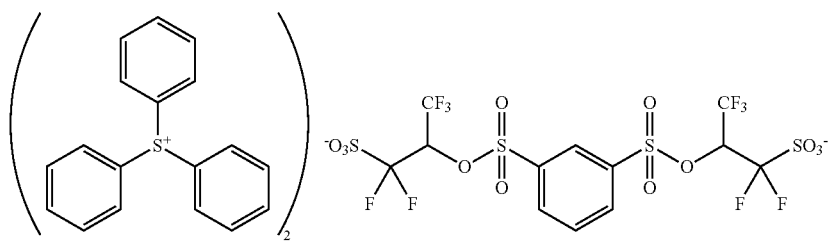
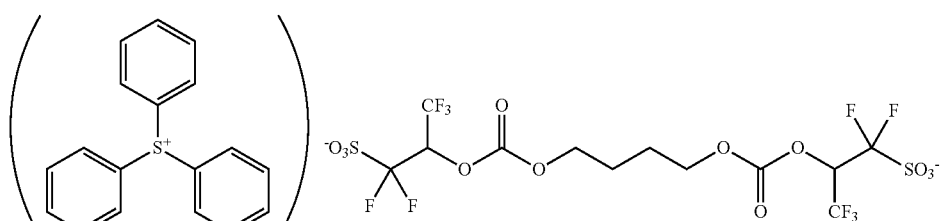
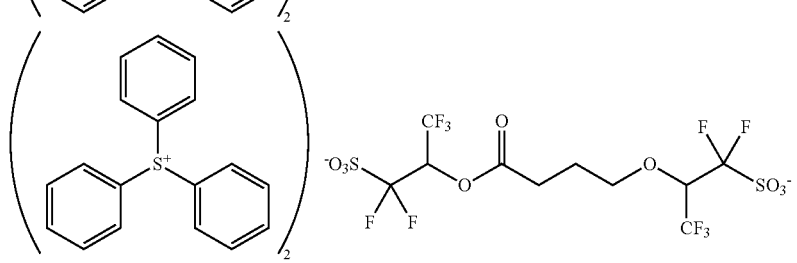

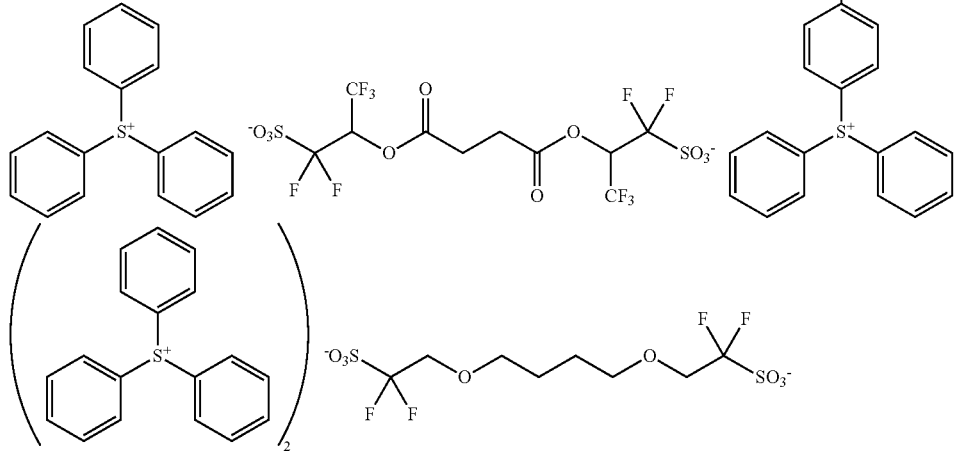

The PAG of the invention is characterized in that the anion moiety has a specific bissulfonate structure. A resist composition comprising the PAG of the invention has a high ability to control acid diffusion and eventually achieves improvements in resist characteristics, especially MEF. It is believed that these improvements are attributable to a highly polar structure having two salt structures within the molecule. It is noted that JP 3773139 discloses a resist composition comprising a bissulfonium cation. Since the polarity of the anion moiety is unchanged from prior art monosulfonium salts, the resist composition of JP 3773139 is believed not to have a high acid diffusion control ability comparable to the invention, failing to exert satisfactory lithography performance.

JP-A 2008-013551 and WO 2011/048919 describe resist compositions comprising a PAG having a bissulfonate anion. In general, bisonium salts are less soluble in organic solvents because of their high polarity. This nature may interfere with coating and suggest dissolution in water during immersion lithography, both resulting in defects. In contrast, the PAG of the invention has improved solvent solubility, minimizes defect formation, and offers a very useful resist composition.

Further the PAG of the invention has a high sensitivity as compared with conventional monoonium salts. Although the reason is not well understood, the invention is eventually successful in achieving a good balance of sensitivity and MEF, which are in a tradeoff relationship in the prior art.

When compounded in a resist composition, the PAG having formula (1a) or (1b) is preferably used in an amount of 0.1 to 40 parts, more preferably 1 to 20 parts by weight per 100 parts by weight of the base resin. Outside the range, less amounts fail to achieve the desired function whereas more amounts may result in performance degradations such as a low sensitivity and formation of foreign particles due to poor solubility.

The PAG or carboxylic acid onium salt of the invention may be synthesized according to the following Scheme 1, for example.

Scheme 1

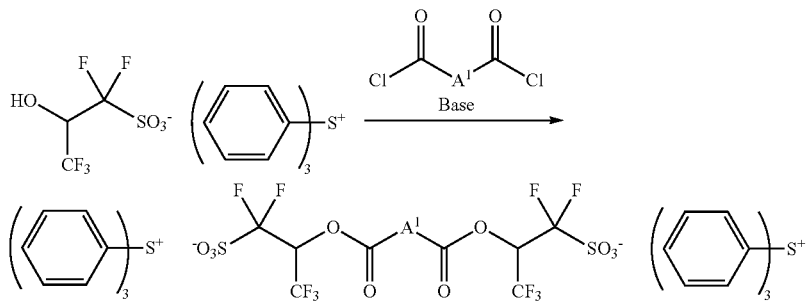

Herein $A^1$ is as defined above.

The starting reactant, triphenylsulfonium 1,1,3,3,3-pentafluoro-2-hydroxypropane-1-sulfonate is reacted with a disulfonyl halide under basic conditions to synthesize the desired bissulfonium salt.

It is possible to similarly synthesize a bisonium salt having an ether bond if a terminally dihalogenated alkyl is used instead of the acid halide, a bisonium salt having a carbamate bond if a diisocyanate compound is used instead, a bisonium salt having a sulfonic acid ester bond if a disulfonyl halide is used instead, and a bisonium salt having a carbonate bond if a di-haloformic acid ester is used instead. If the cation of the starting reactant is changed, a bisonium salt having a different cation structure may be synthesized. Also iodonium cation salts may be similarly synthesized.

In an alternative synthesis route, a derivative is prepared from the starting reactant whose cation species is changed to an alkali metal salt such as sodium or potassium or ammonium salt, according to the above Scheme, and ion exchange reaction is effected on the derivative to convert its cation species to the desired one. The ion exchange reaction may be readily effected by well-known methods, for example, with reference to JP-A 2007-145797.

Resist Composition

Another embodiment of the invention is a chemically amplified resist composition comprising (A) the photoacid generator having formula (1a) or (1b) as an essential component, (B) a base resin, and (E) an organic solvent. The composition may further comprise:

(C) a photoacid generator other than the photoacid generator having formula (1a) or (1b) (also referred to as second photoacid generator), (D) a quencher, (F) a surfactant which is insoluble or substantially insoluble in water and soluble in alkaline developer, and/or a surfactant which is insoluble or substantially insoluble in water and alkaline developer (also referred to as hydrophobic resin), and (G) an organic acid derivative and/or fluorinated alcohol. Components (C), (D), (F), and (G) are optional, that is, may be added if necessary.

(B) Base Resin

The base resin used herein is preferably a polymer comprising recurring units having the general formula (2) and recurring units having the general formula (3).

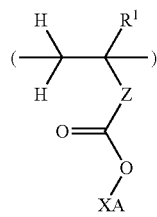

(2)

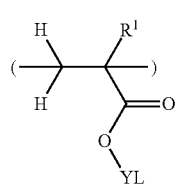

(3)

Herein $R^1$ is hydrogen, fluorine, methyl or trifluoromethyl. Z is a single bond, phenylene group, naphthylene group or (backbone)-C(=O)—O—Z'—, wherein Z' is a $C_1$-$C_{10}$ straight, or $C_3$-$C_{10}$ branched or cyclic alkylene group which may contain a hydroxyl radical, ether bond, ester bond or lactone ring, or phenylene group or naphthylene group. XA is an acid labile group. YL is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

Examples of the structure having formula (2) wherein Z is a variant are shown below.

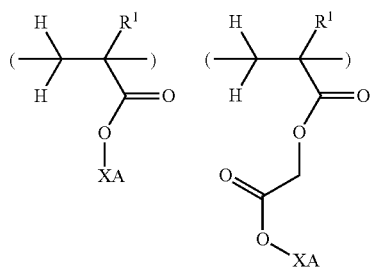

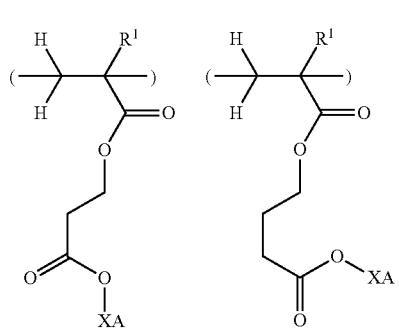

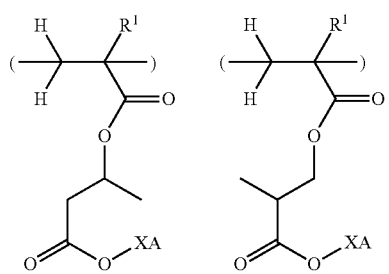

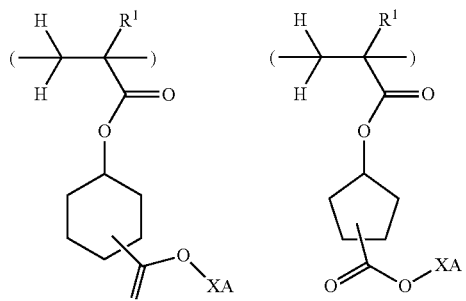

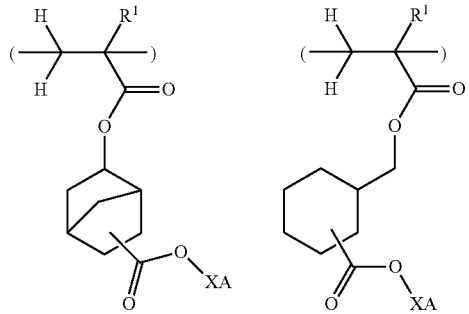

-continued

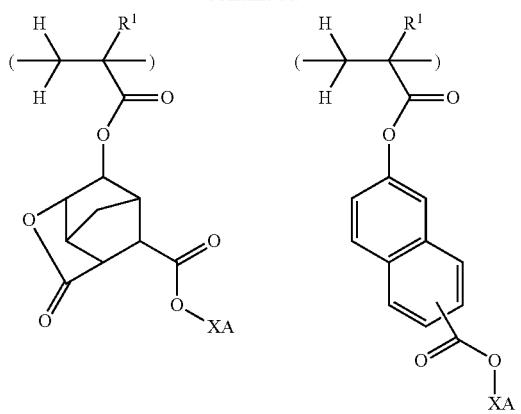

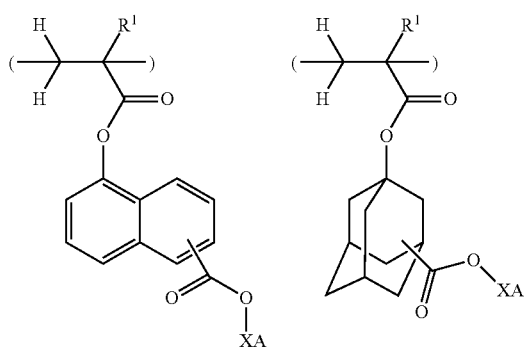

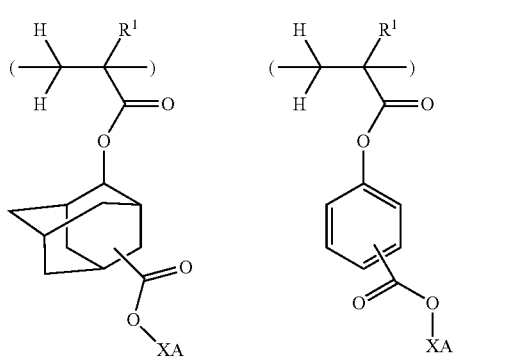

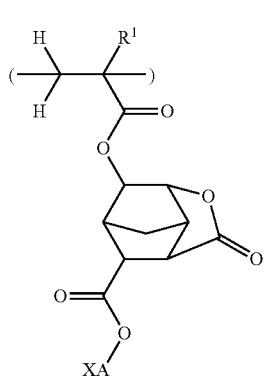

-continued

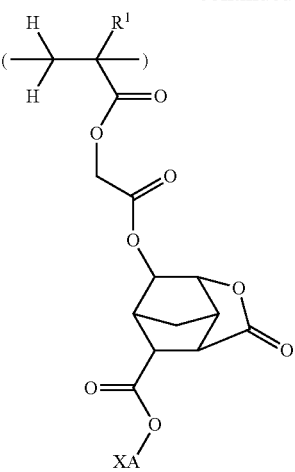

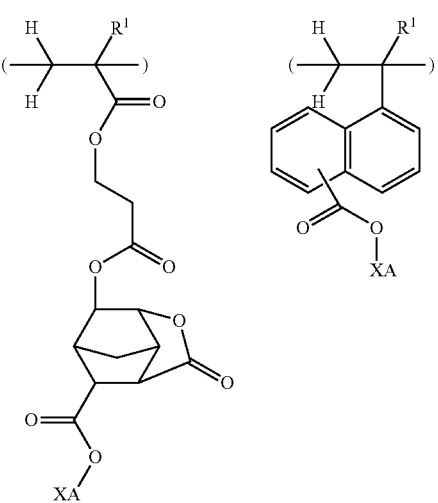

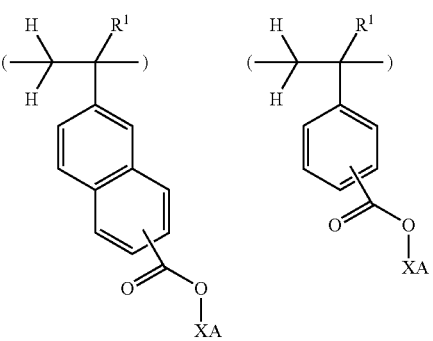

Under the action of acid, a polymer comprising recurring units of formula (2) is decomposed to generate carboxylic acid, turning to be an alkali soluble polymer. The acid labile group represented by XA may be selected from a variety of such groups. Examples of the acid labile group include groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

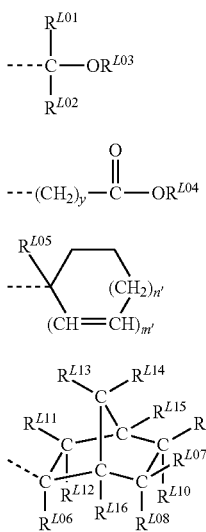

(L1)

(L2)

(L3)

(L4)

In these formulae (and throughout the disclosure), the broken line denotes a valence bond.

In formula (L1), $R^{L01}$ and $R^{L02}$ each are hydrogen or a straight, branched or cyclic alkyl group of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like, or in which an oxygen atom intervenes between carbon atoms. Exemplary straight, branched or cyclic alkyl groups include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl. Illustrative examples of the substituted alkyl groups are shown below.

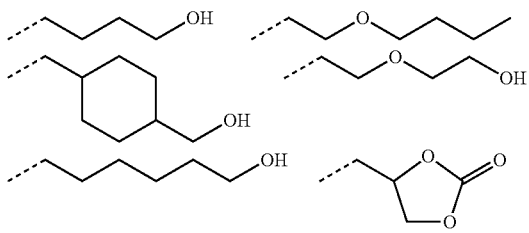

A pair of $R^{L01}$ and $R^{L02}$, $R^{L01}$ and $R^{L03}$, or R and R may bond together to form a ring with the carbon and oxygen atoms to which they are attached. Each of $R^{L01}$, $R^{L02}$ and $R^{L03}$ is a straight or branched alkylene group of 1 to 18 carbon atoms, preferably 1 to 10 carbon atoms when they form a ring.

In formula (L2), $R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is a substituted or unsubstituted, straight, branched or cyclic $C_1$-$C_8$ alkyl group or a substituted or unsubstituted $C_6$-$C_{20}$ aryl group. Examples of the optionally substituted alkyl group include straight, branched or cyclic alkyl groups such as methyl, ethyl, propyl, isopropyl, n-butyl, sec-butyl, tert-butyl, tert-amyl, n-pentyl, n-hexyl, cyclopentyl, and cyclohexyl, and substituted forms of such groups in which some hydrogen atoms are substituted by hydroxyl, alkoxy, carboxyl, alkoxycarbonyl, oxo, amino, alkylamino, cyano, mercapto, alkylthio, sulfo or other groups. Examples of the optionally substituted aryl groups include phenyl, methylphenyl, naphthyl, anthryl, phenanthryl, and pyrenyl. Letter m' is equal to 0 or 1, n' is equal to 0, 1, 2 or 3, and 2m'+n' is equal to 2 or 3.

In formula (L4), $R^{L06}$ is a substituted or unsubstituted, straight, branched or cyclic $C_1$-$C_8$ alkyl group or a substituted or unsubstituted $C_6$-$C_{20}$ aryl group. Examples of these groups are the same as exemplified for $R^{L05}$. $R^{L07}$ to $R^{L16}$ independently represent hydrogen or monovalent $C_1$-$C_{15}$ hydrocarbon groups. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxyl, alkoxycarbonyl, oxo, amino, alkylamino, cyano, mercapto, alkylthio, sulfo or other groups. Alternatively, two of $R^{L07}$ to $R^{L16}$, taken together, form a ring with the carbon atom to which they are attached (for example, a pair of $R^{L07}$ and $R^{L08}$, $R^{L07}$ and $R^{L09}$, $R^{L07}$ and $R^{L10}$, $R^{L08}$ and $R^{L10}$, $R^{L09}$ and $R^{L10}$, $R^{L11}$ and $R^{L12}$, or $R^{L13}$ and $R^{L14}$ form a ring). Each of $R^{L07}$ to $R^{L16}$ represents a divalent $C_1$-$C_{15}$ hydrocarbon group when they form a ring, examples of which are the ones exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or $R^{L14}$ and $R^{L15}$).

Of the acid labile groups of formula (L1), the straight and branched ones are exemplified by the following groups.

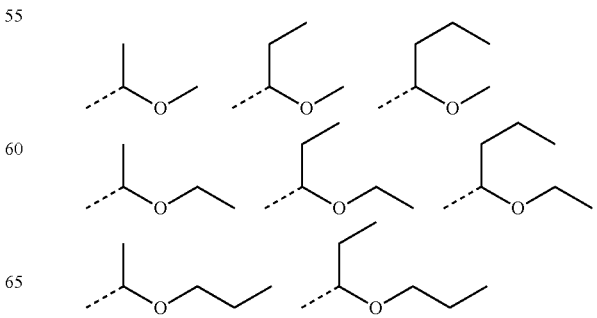

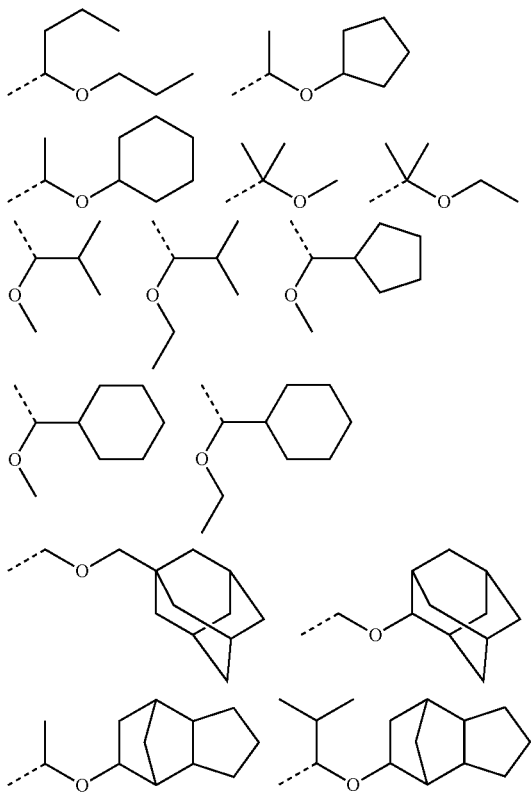

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethyl cyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl groups.

Of the acid labile groups having formula (L4), groups having the following formulas (L4-1) to (L4-4) are preferred.

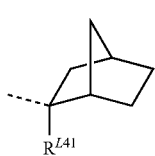
(L4-1)

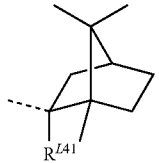
(L4-2)

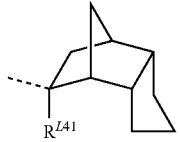
(L4-3)

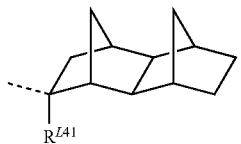
(L4-4)

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two selected from groups having the following general formulas (L4-3-1) and (L4-3-2).

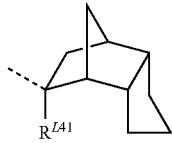
(L4-3-1)

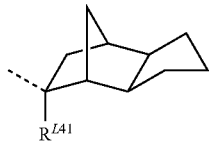
(L4-3-2)

Similarly, the general formula (L4-4) represents one or a mixture of two or more selected from groups having the following general formulas (L4-4-1) to (L4-4-4).

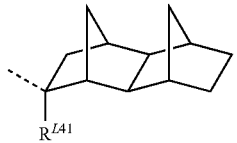
(L4-4-1)

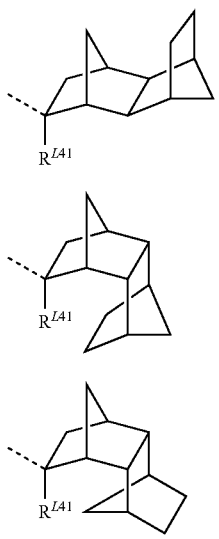

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

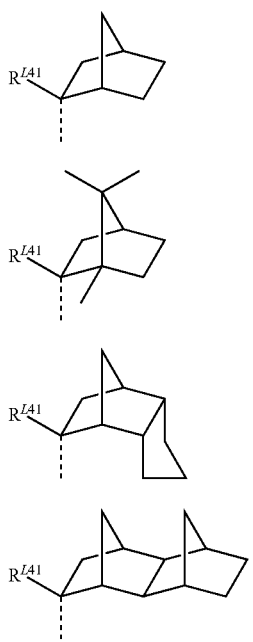

Illustrative examples of the acid labile group of formula (L4) are given below.

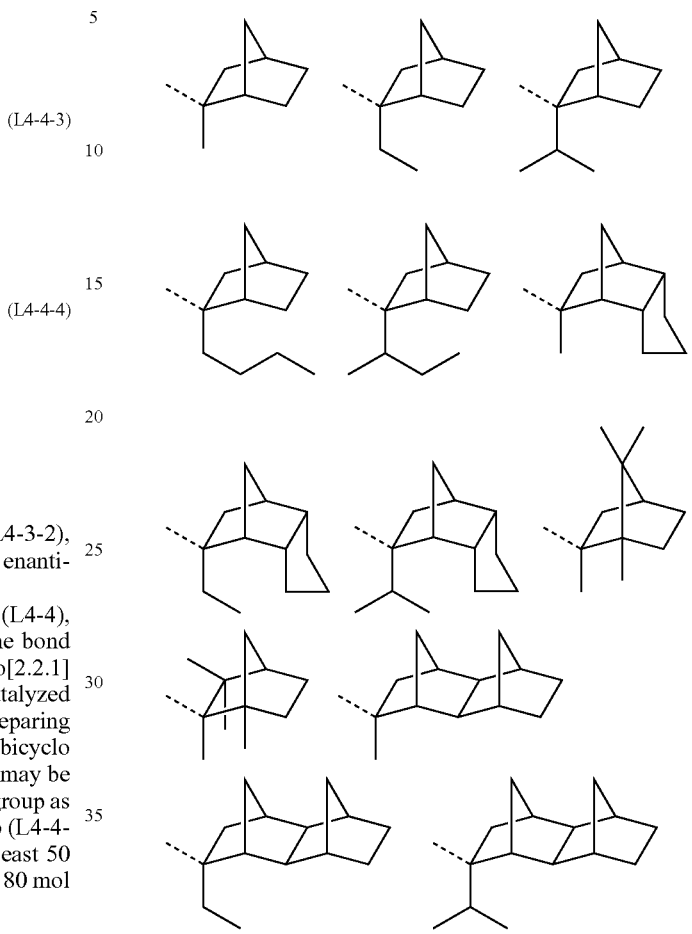

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{LO4}$.

Illustrative examples of the recurring units of formula (2) are given below, but not limited thereto.

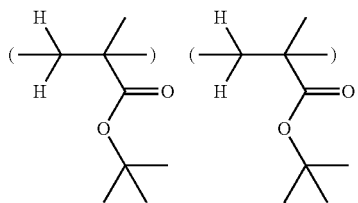

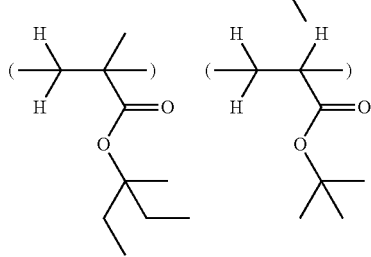

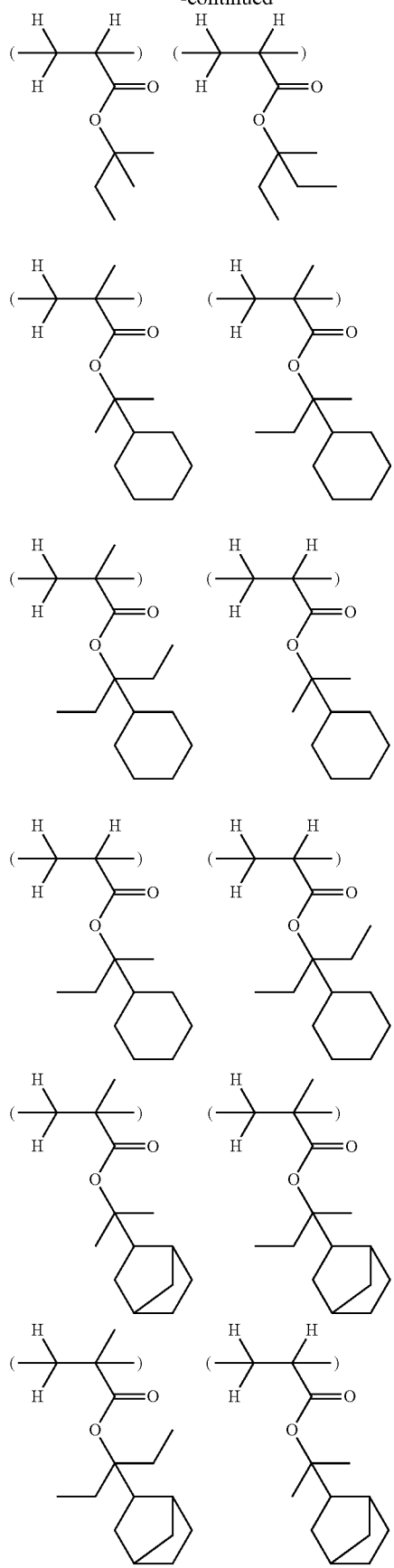
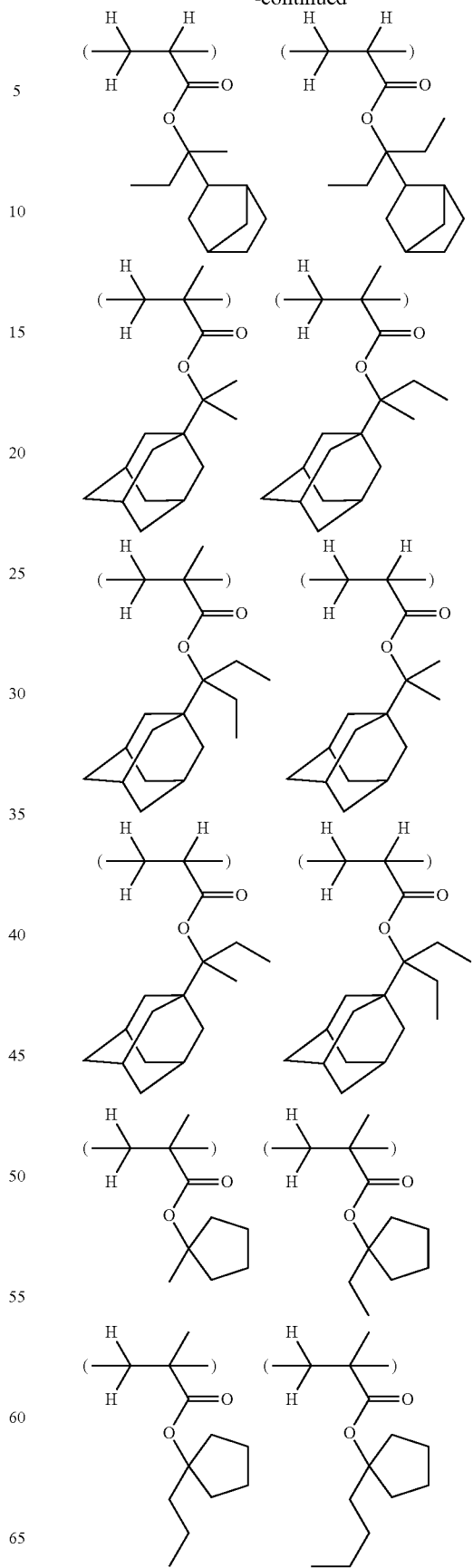

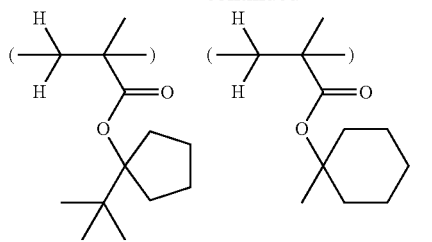
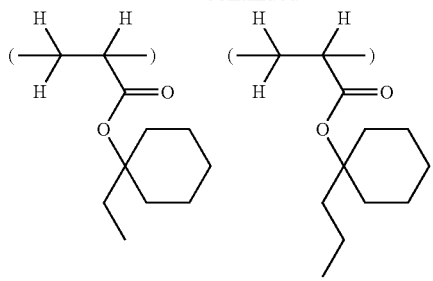
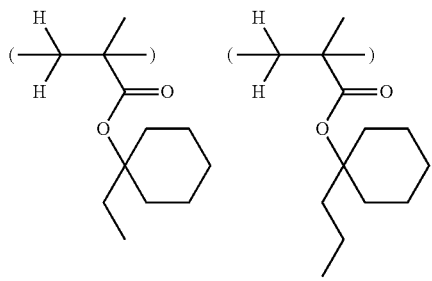
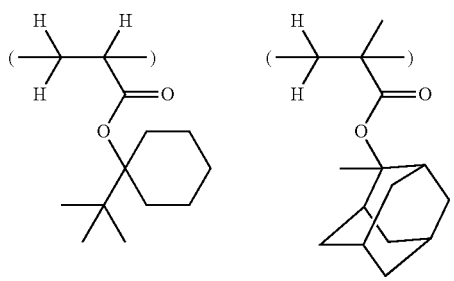
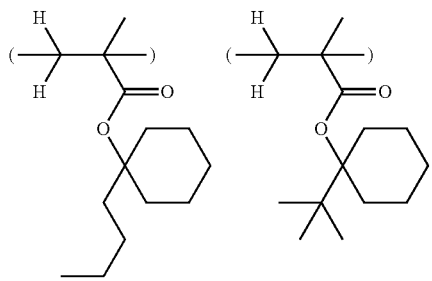
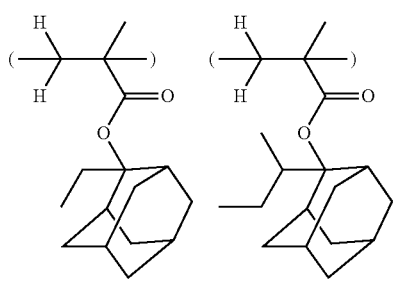
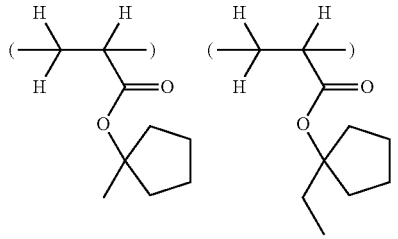
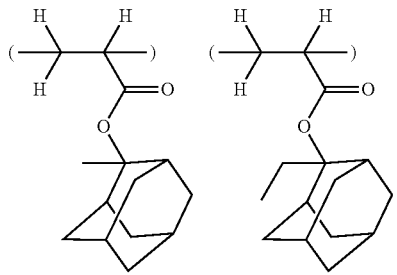
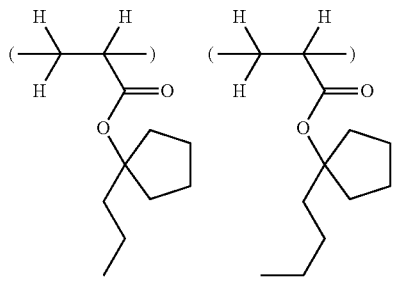
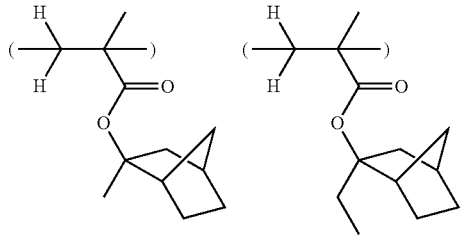
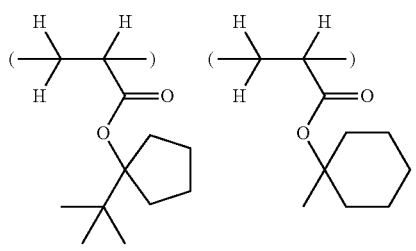
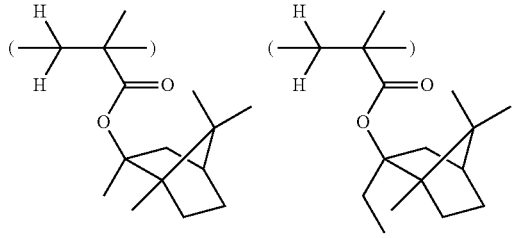

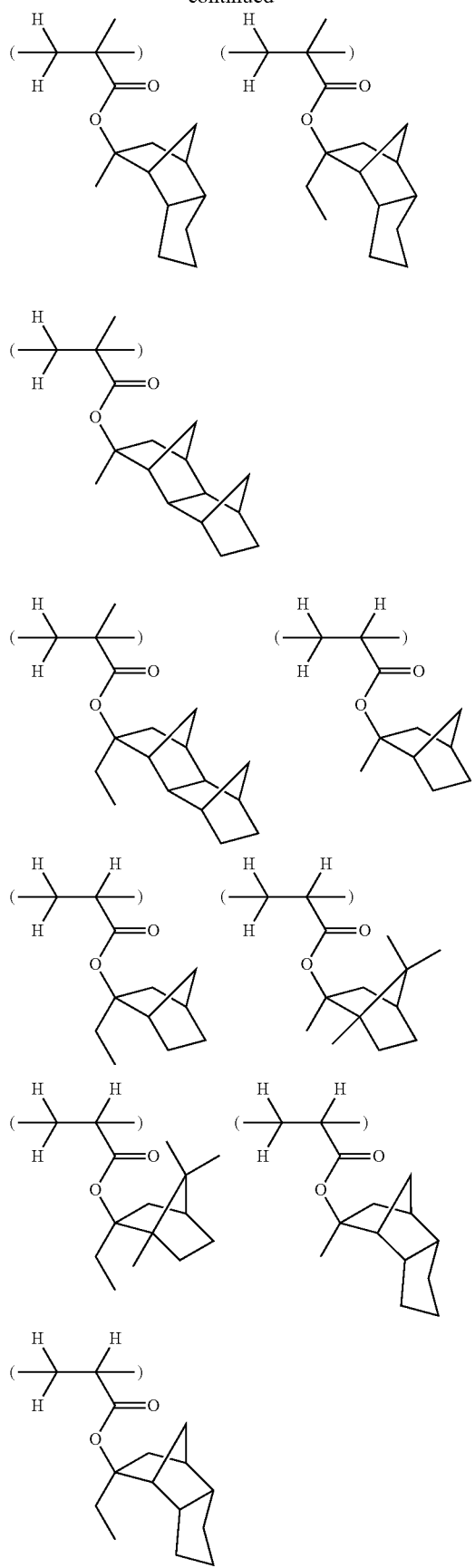
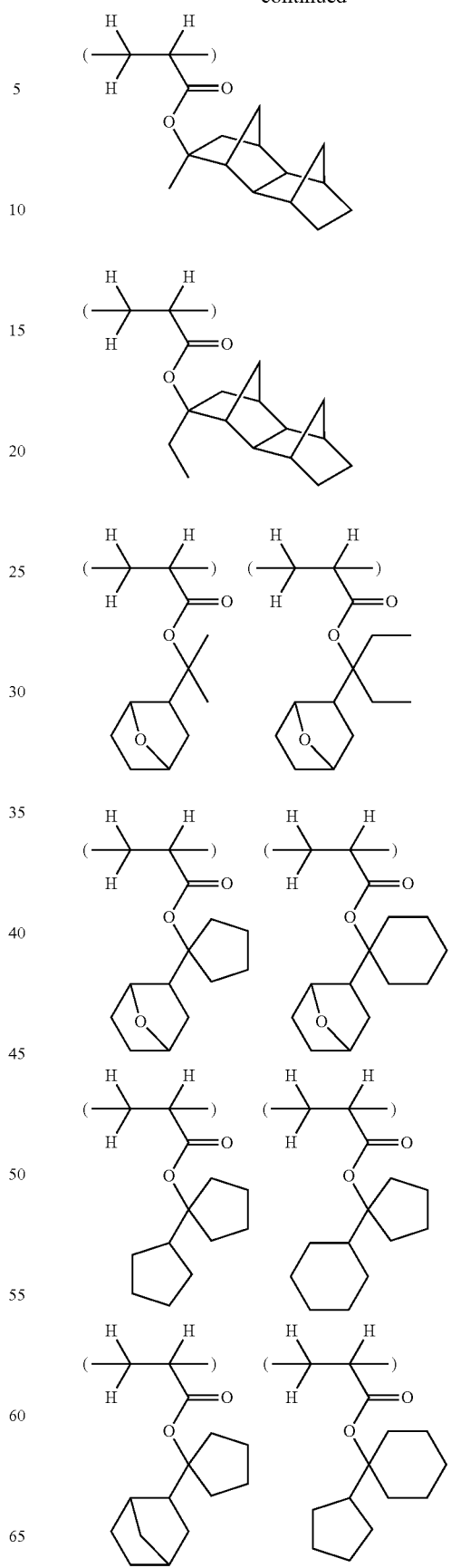

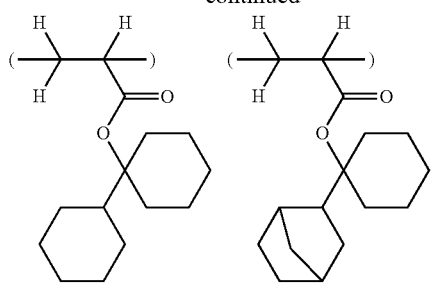
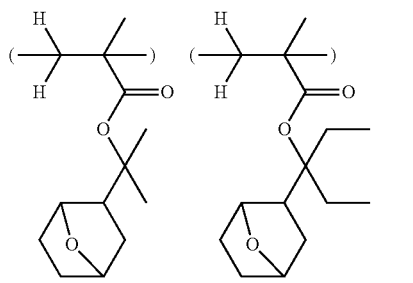
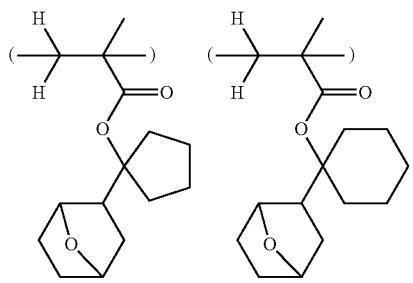
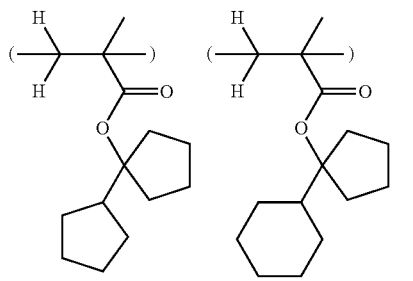
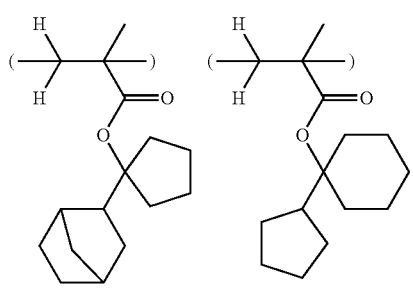
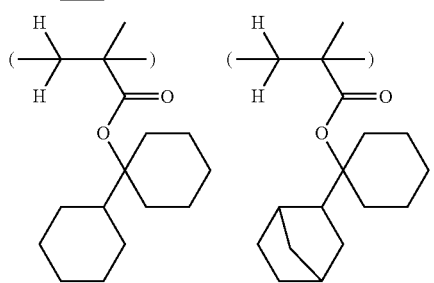
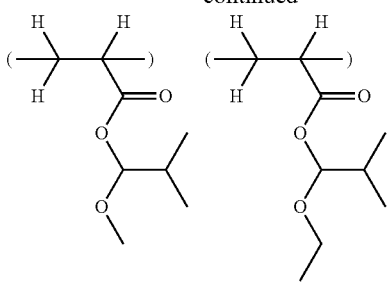
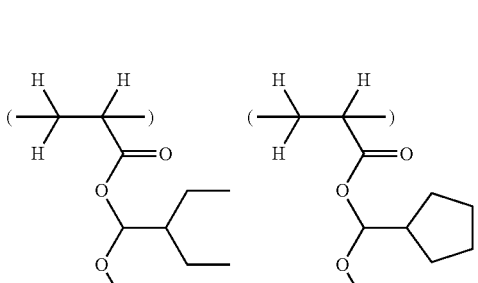
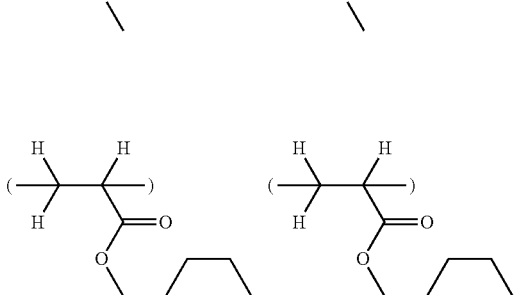
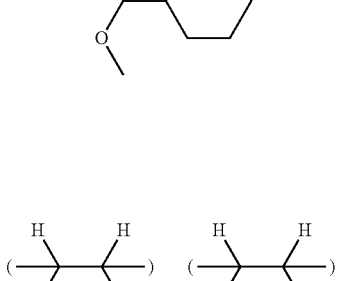
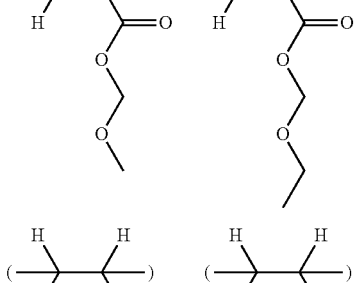
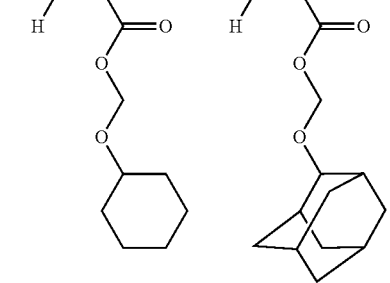

-continued
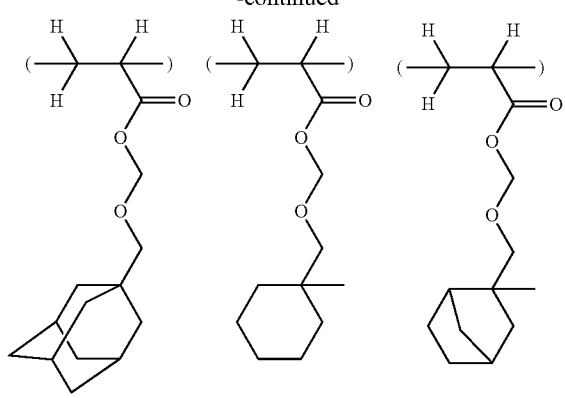
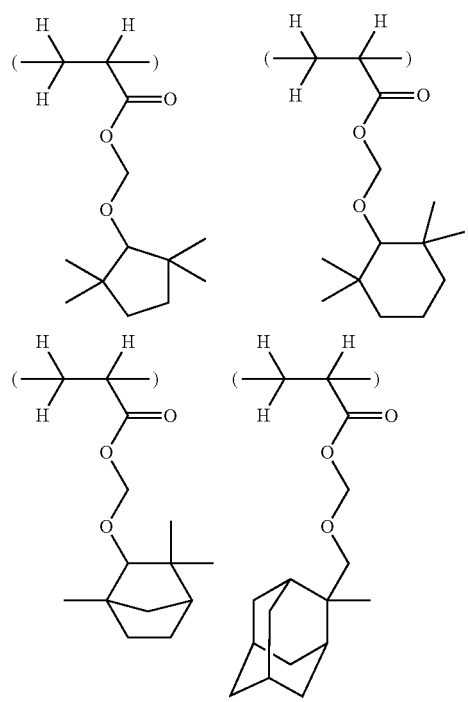
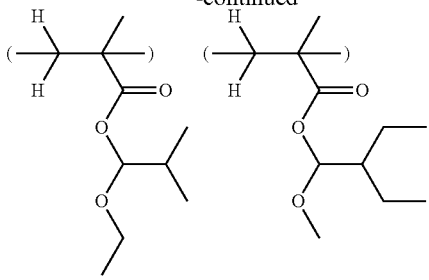
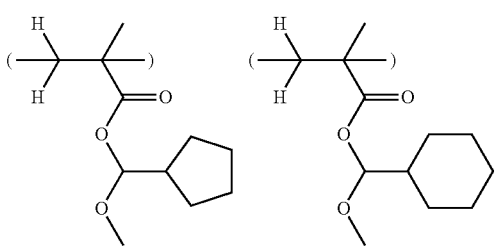
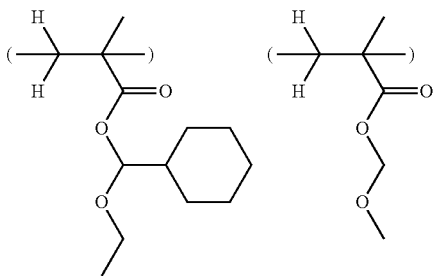
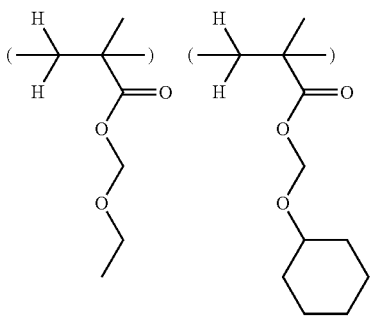
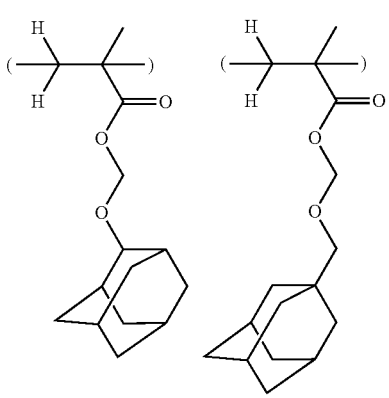

-continued

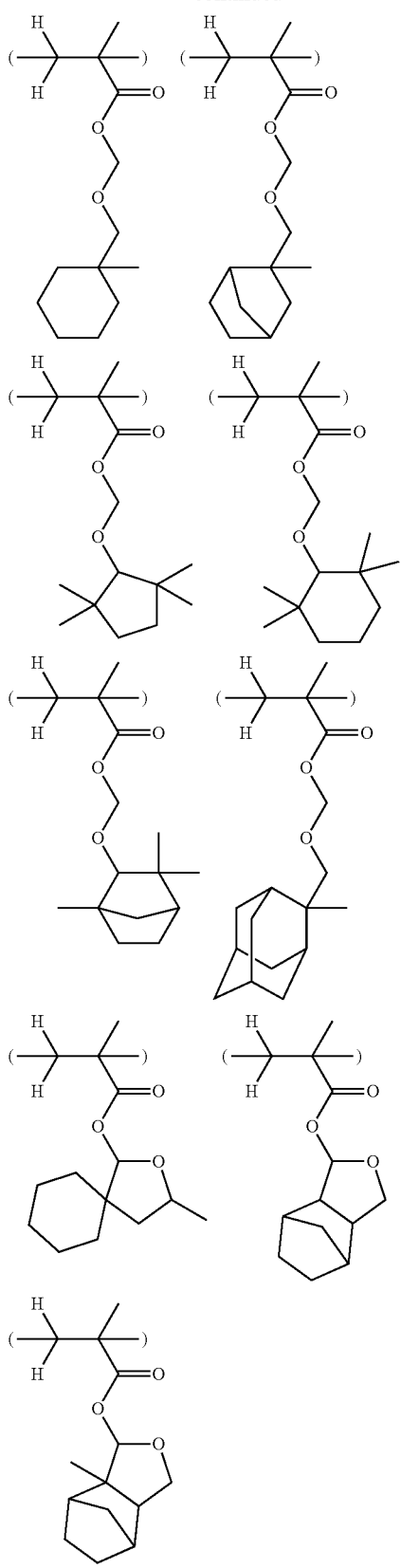

While the foregoing examples correspond to those units wherein Z is a single bond, Z which is other than a single bond may be combined with similar acid labile groups. Examples of units wherein Z is other than a single bond are substantially the same as illustrated above.

In formula (3), YL is hydrogen, or a polar group having one or more structures selected from the group consisting of hydroxyl, cyano, carbonyl, carboxyl, ether bond, ester bond, sulfonic acid ester link, carbonate, lactone ring, sultone ring, and carboxylic anhydride.

Illustrative, non-limiting examples of the recurring units having formula (3) are shown below.

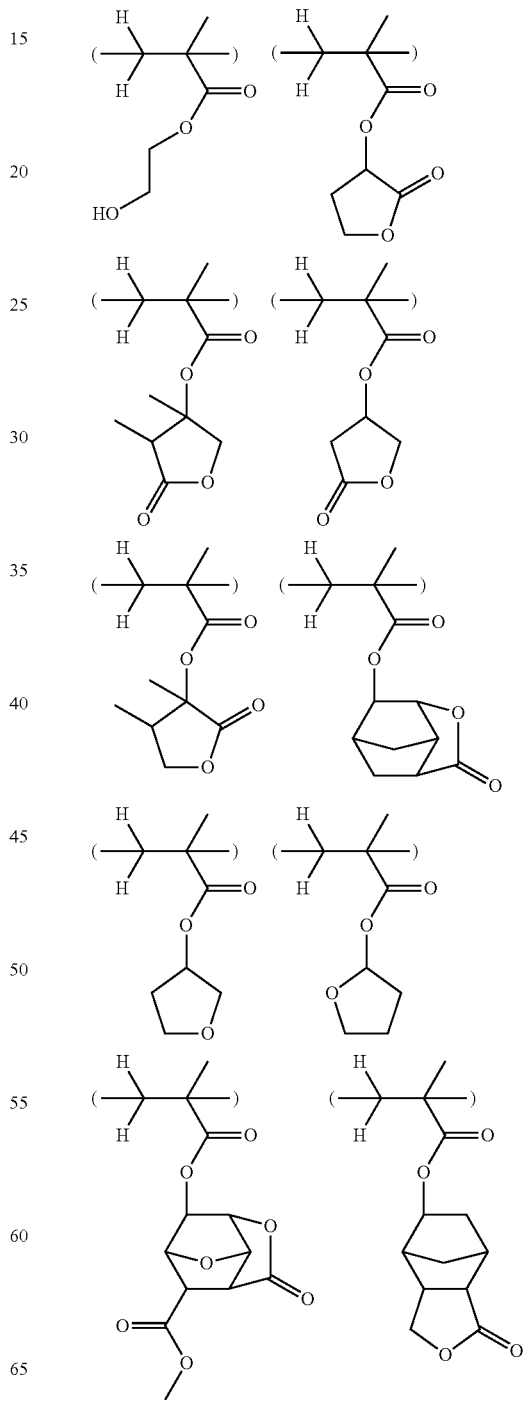

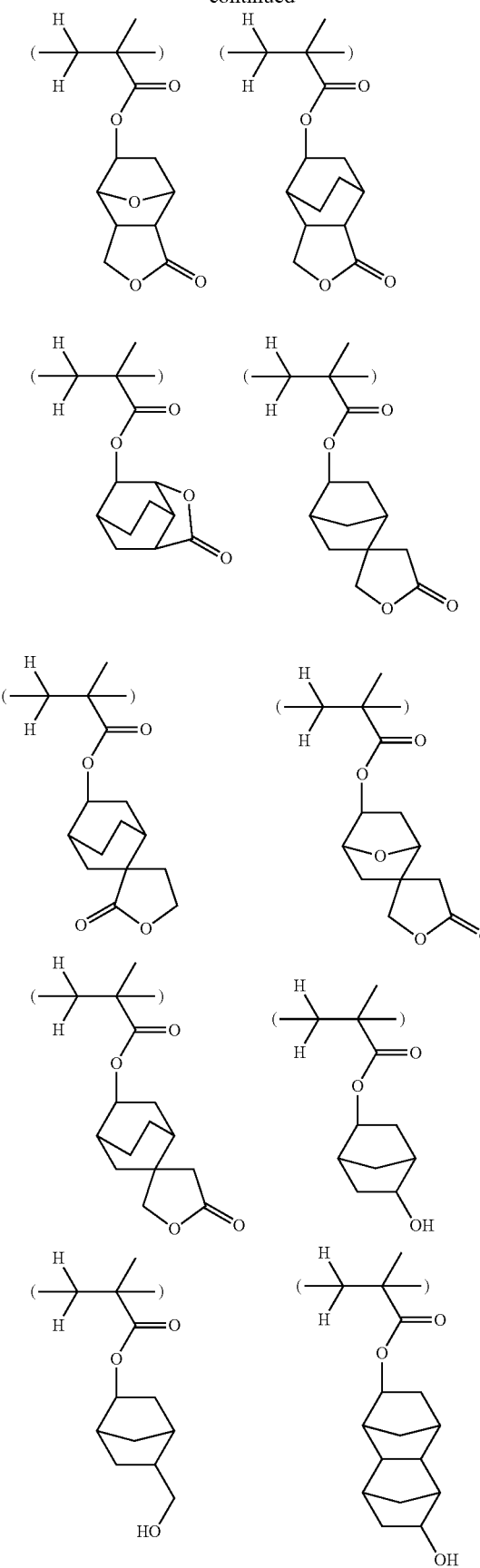
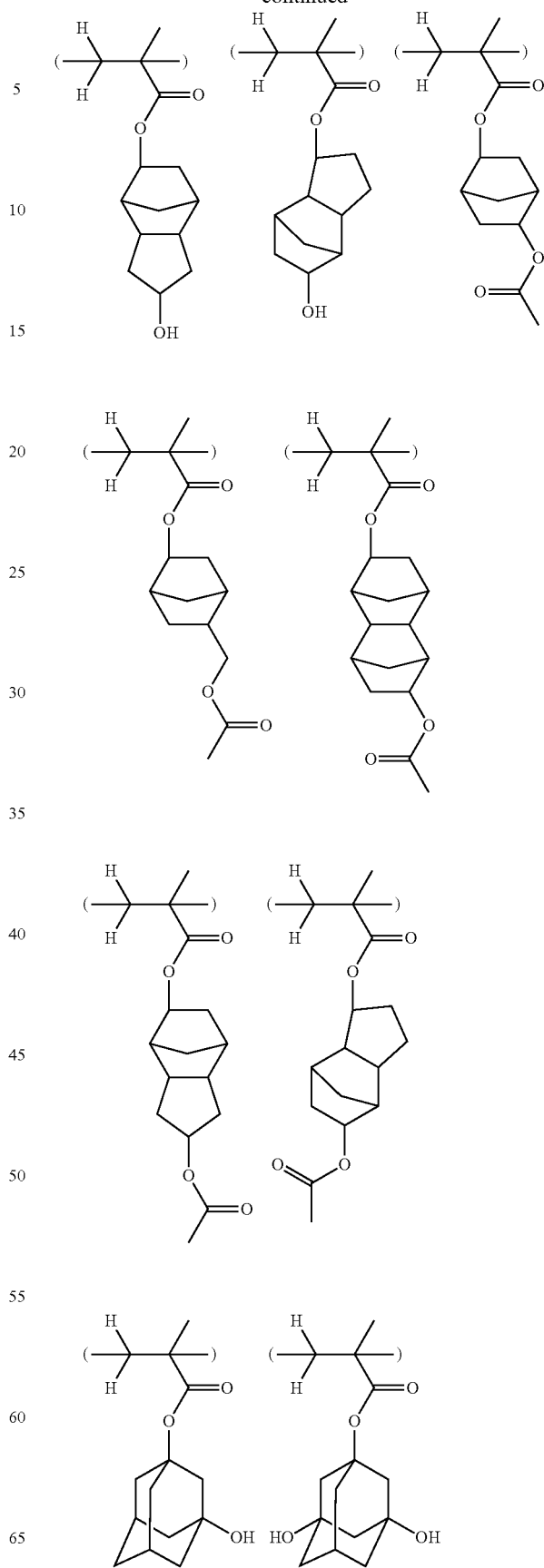

-continued
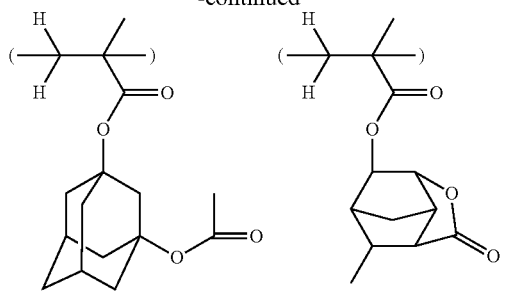
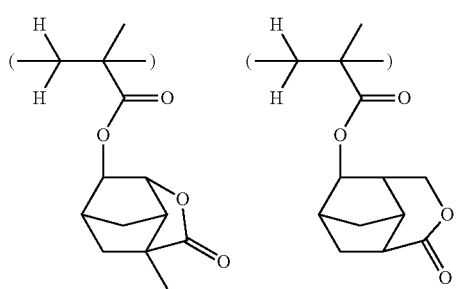
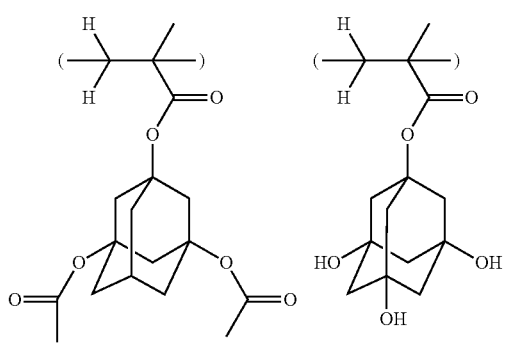
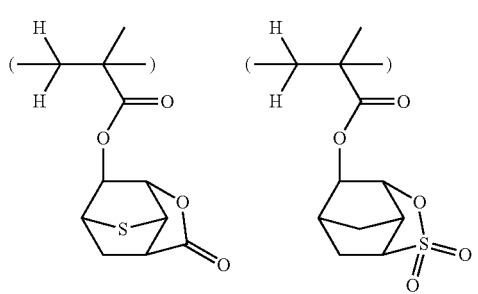
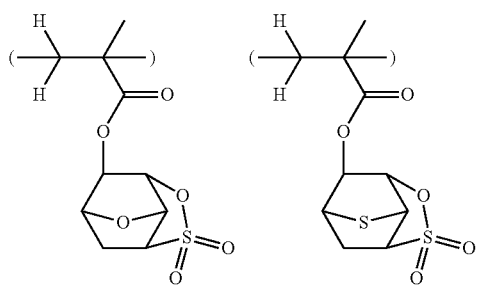
-continued
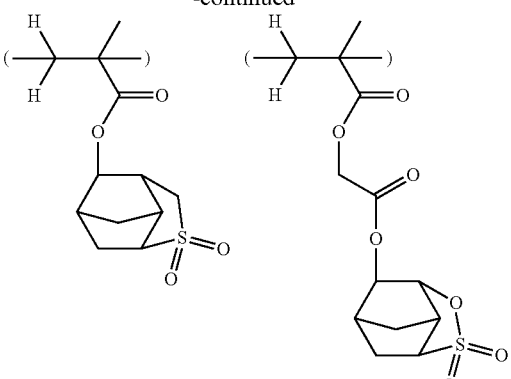
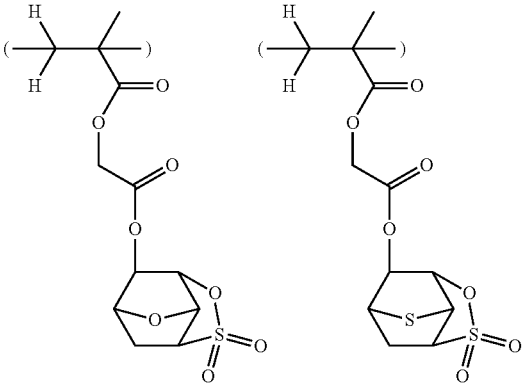
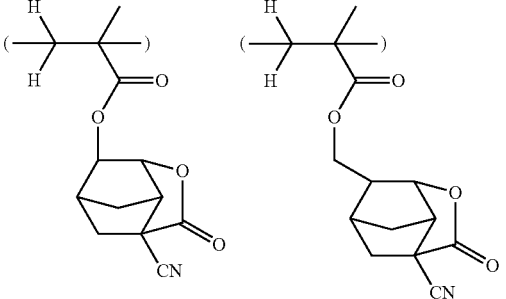
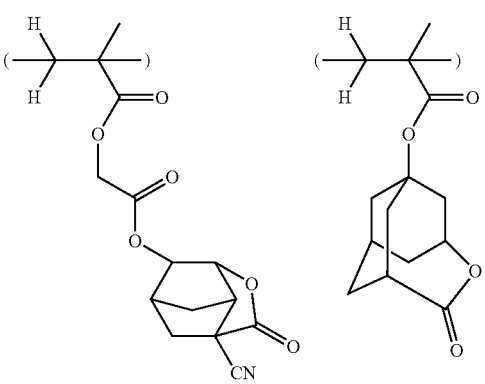

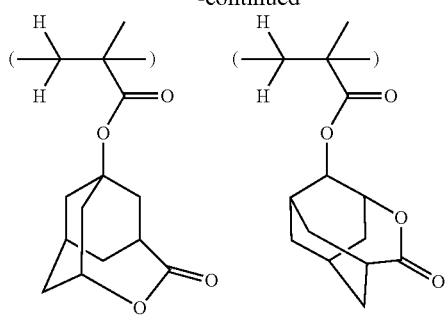
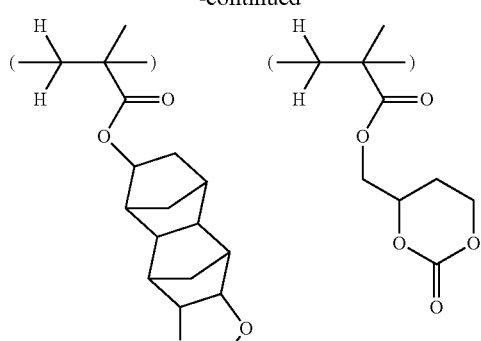
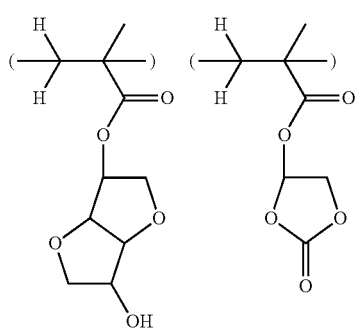
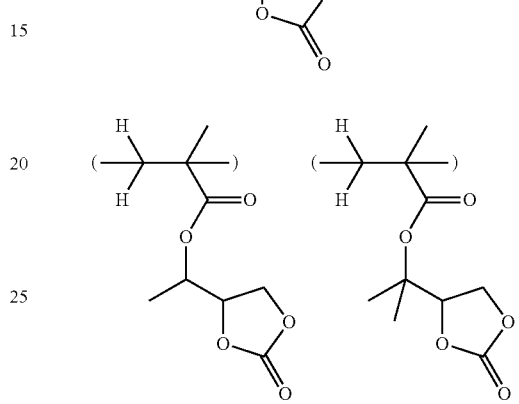
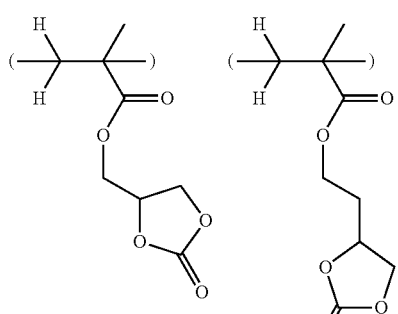
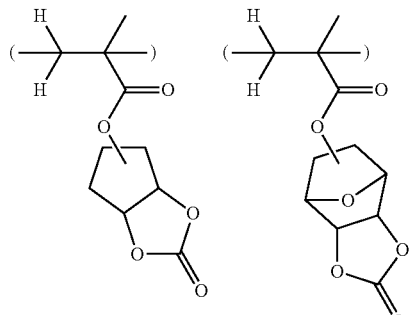
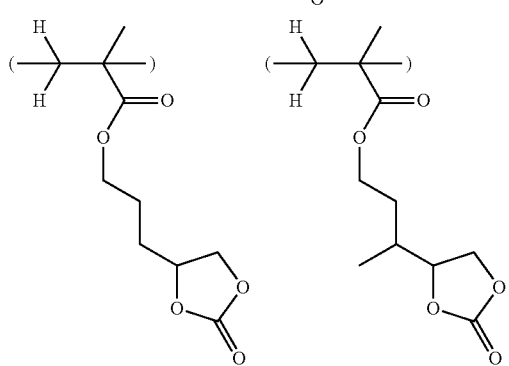
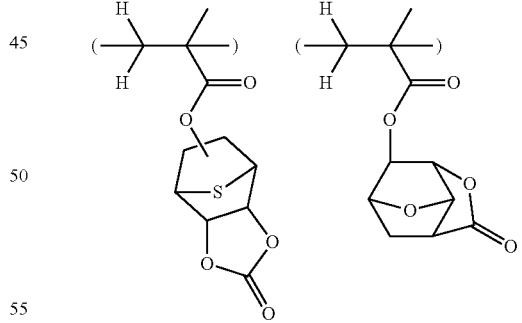
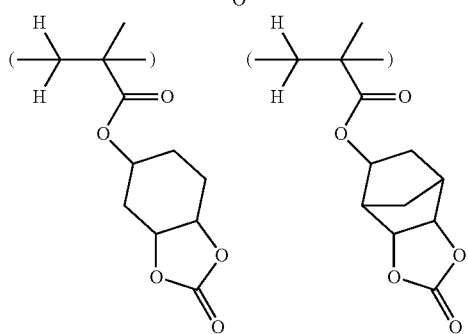
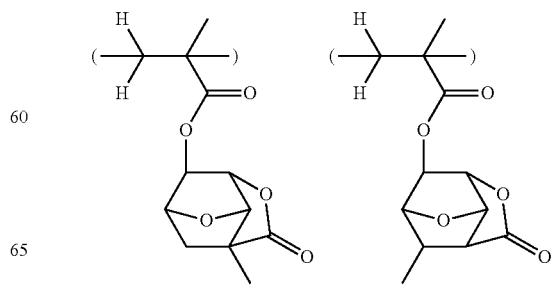

-continued
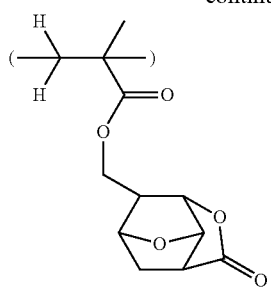
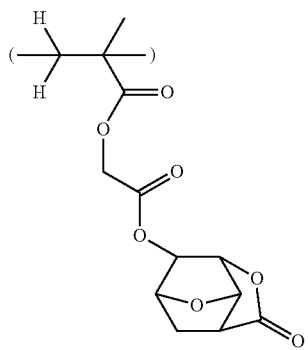
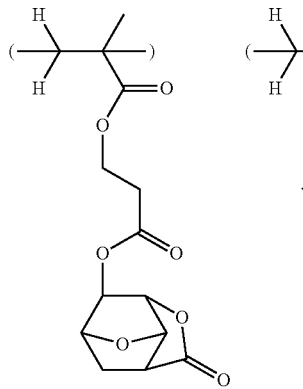
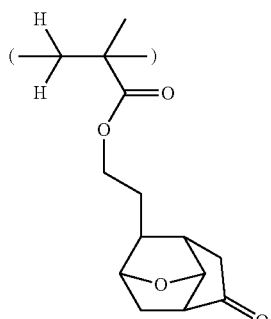
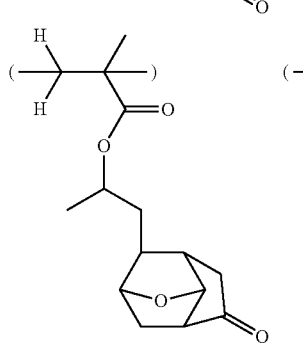
-continued
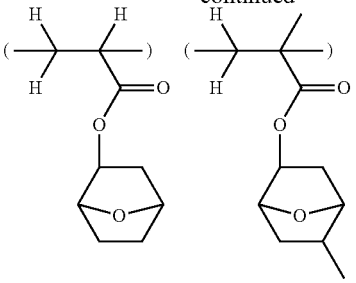
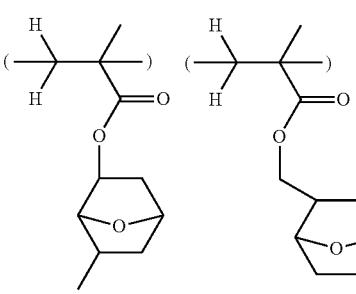
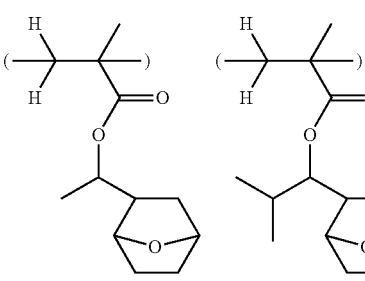
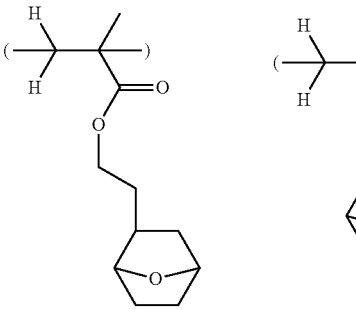
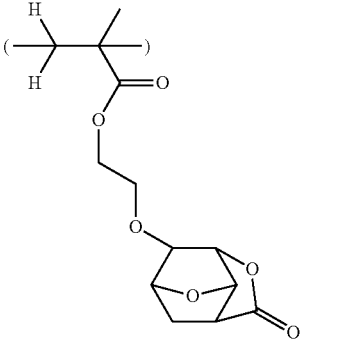

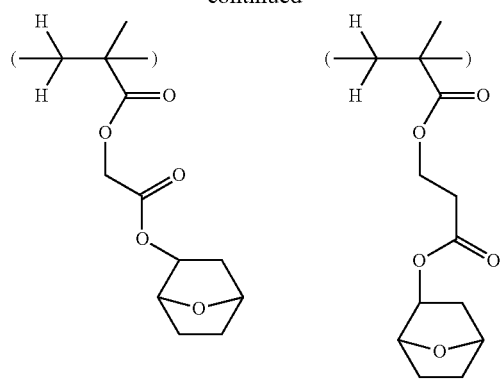
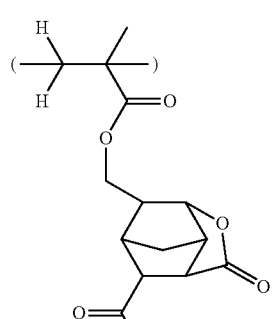
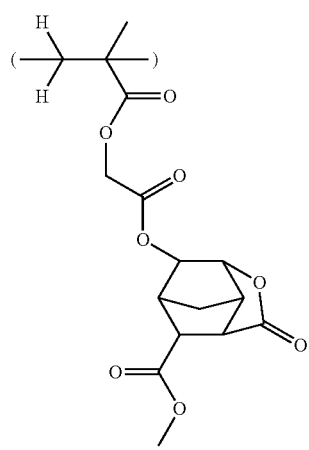 [SMILES: CCC(C)(C)C(=O)OCC(=O)OC1C2CC3C1OC(=O)C3C2C(=O)OC]
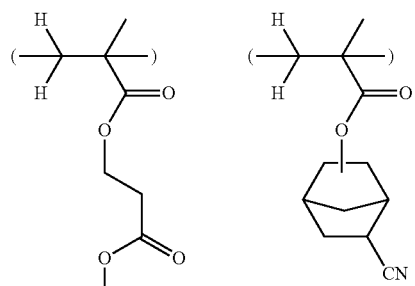
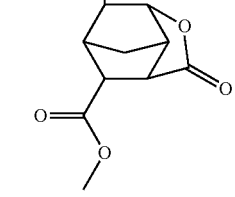
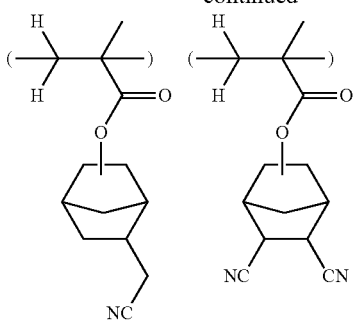
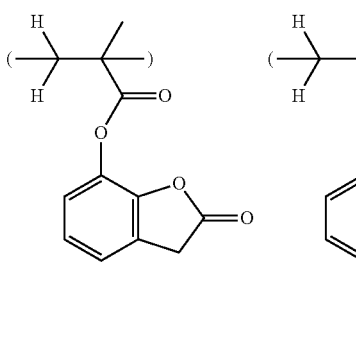
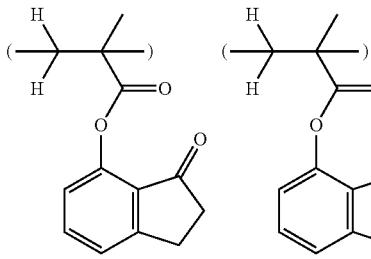
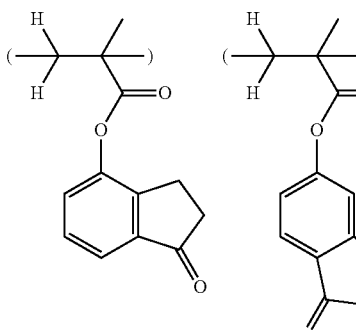
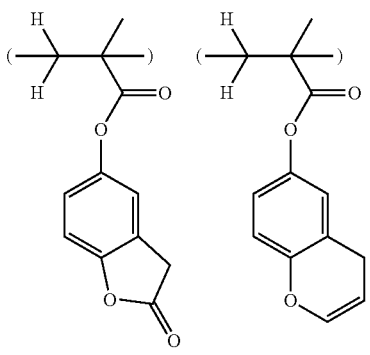

-continued
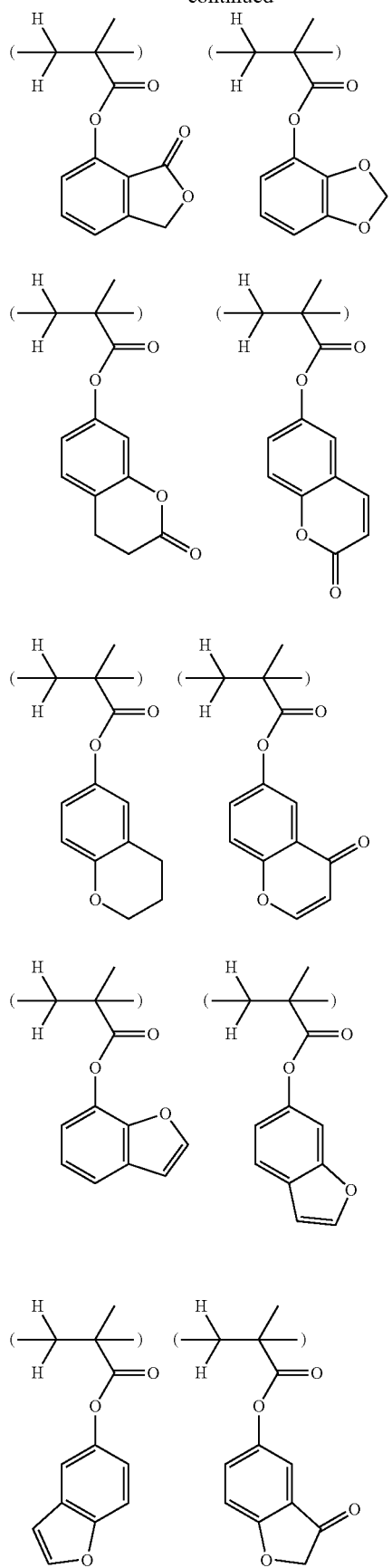
-continued
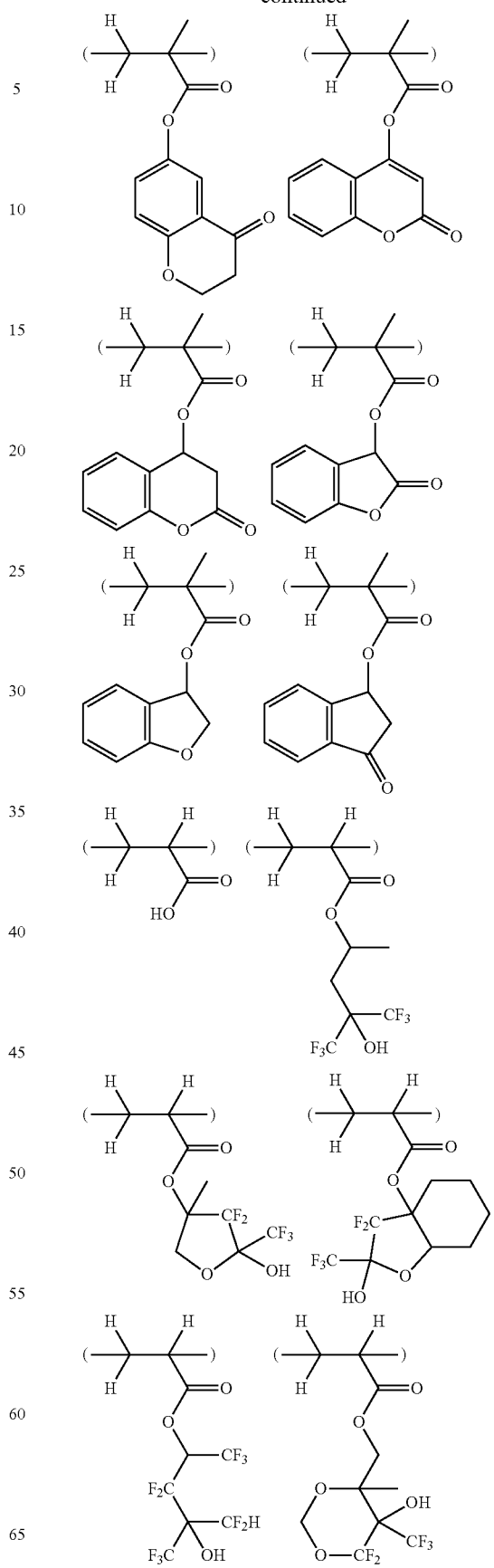

51
-continued
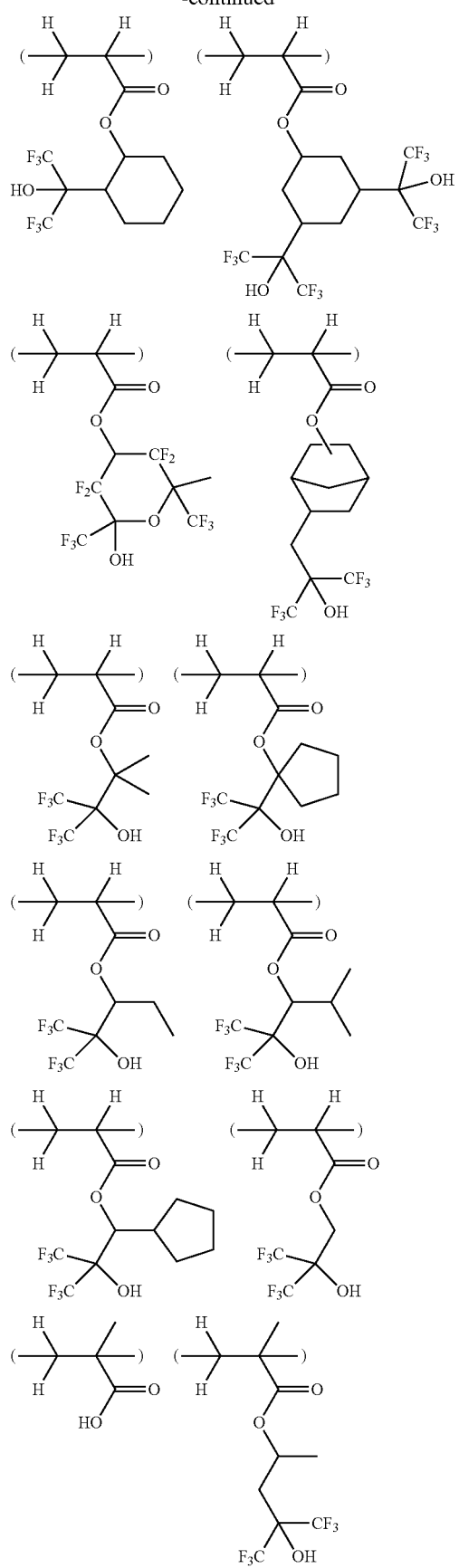
52
-continued
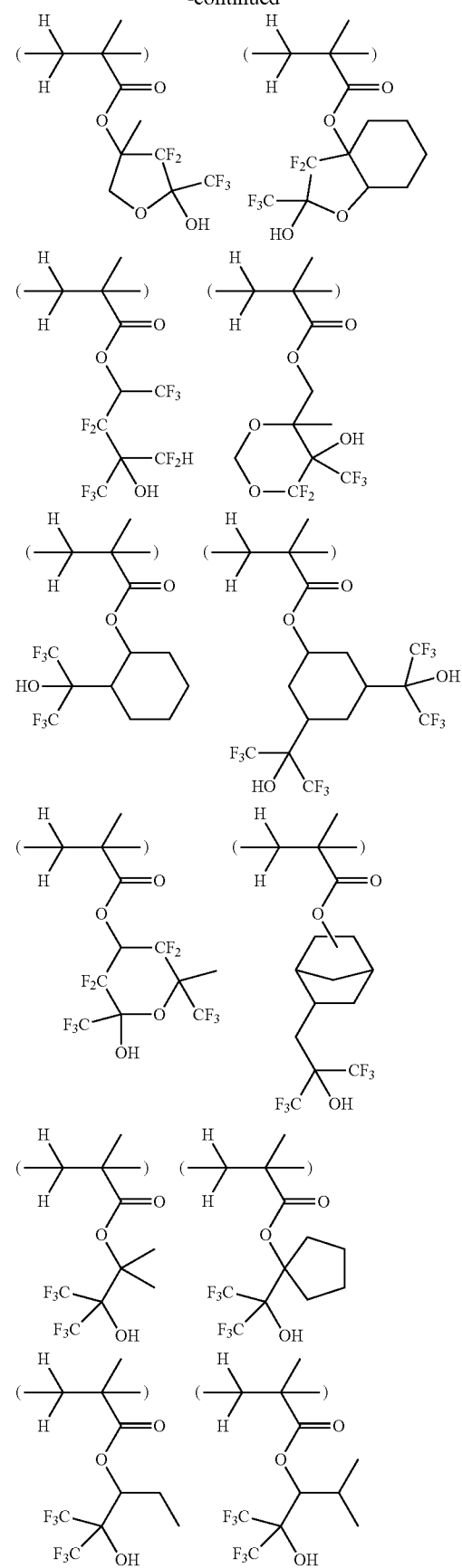

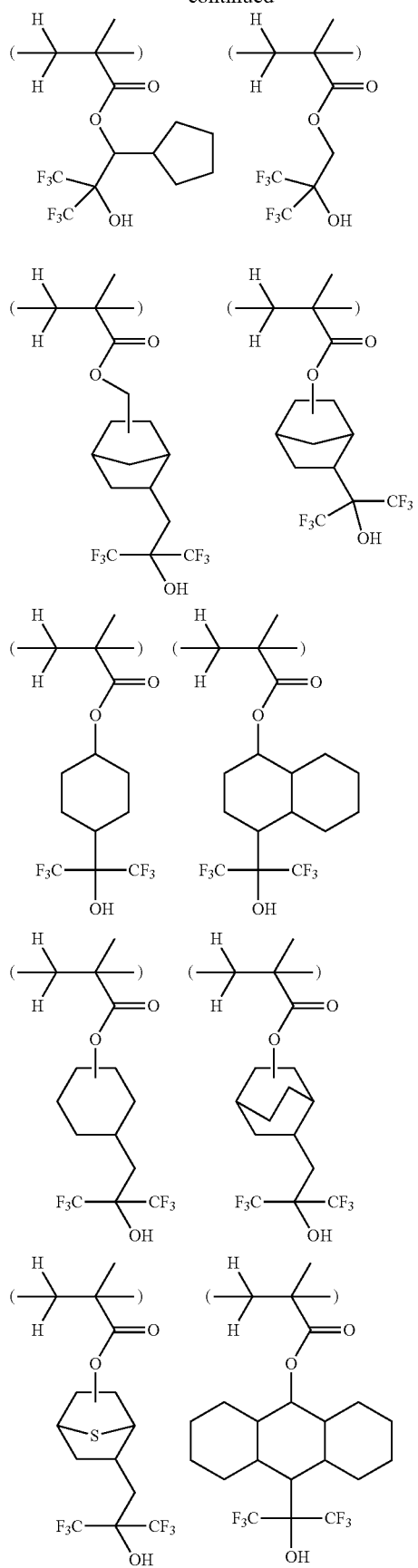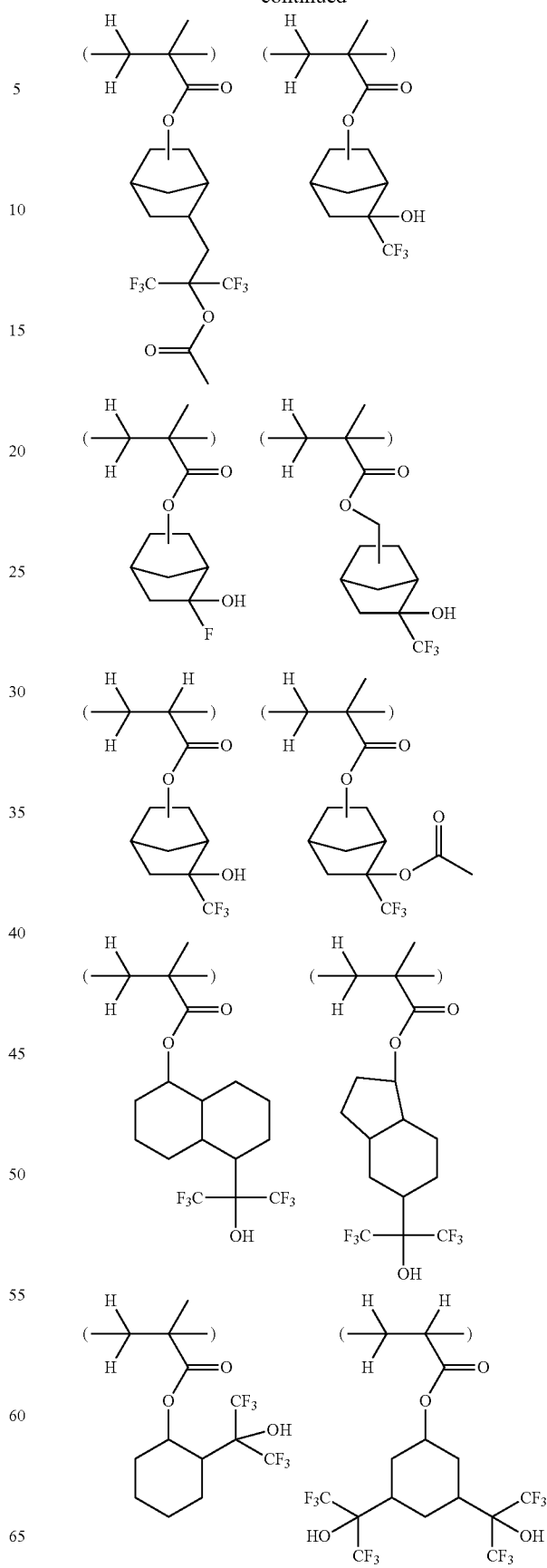

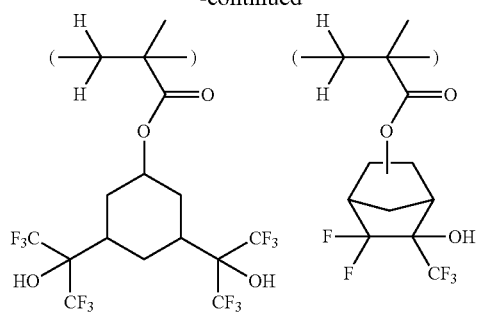
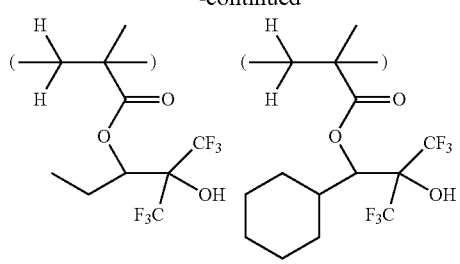
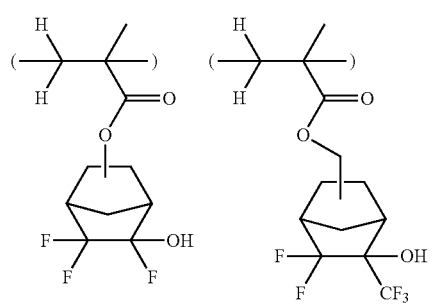
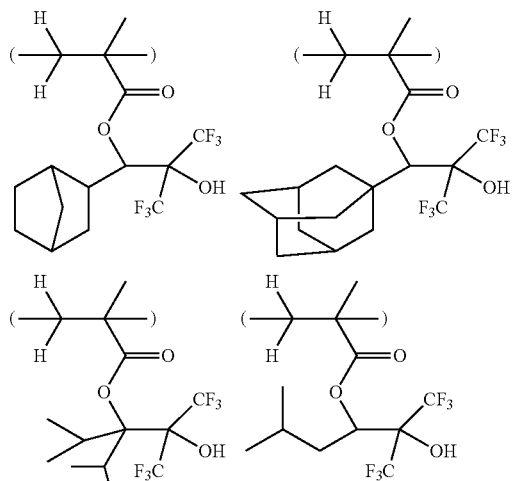
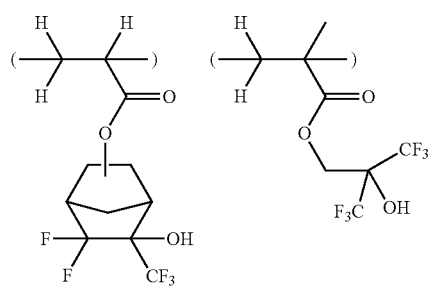
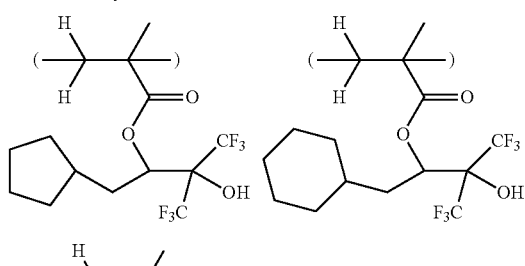
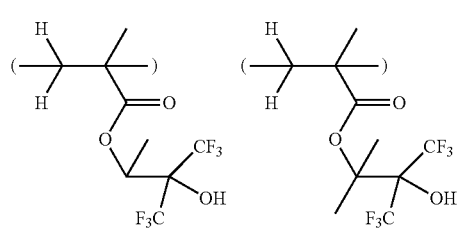
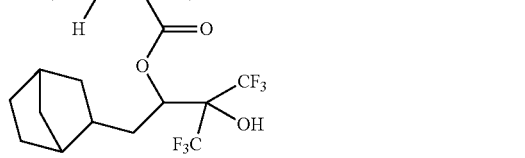
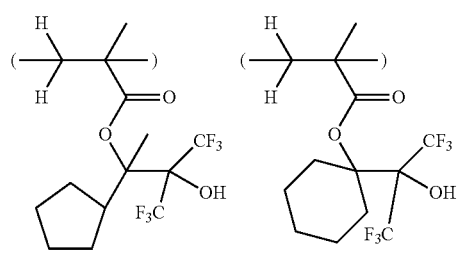
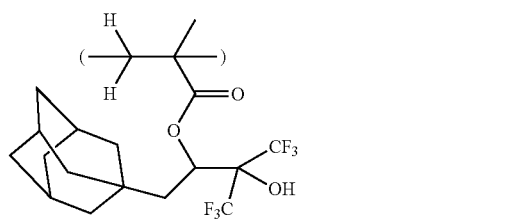
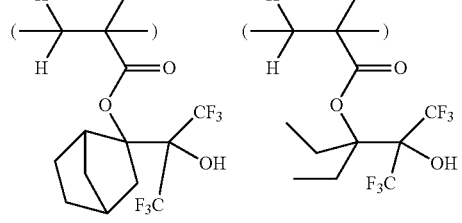
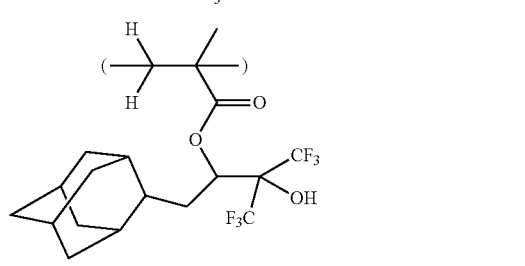

-continued
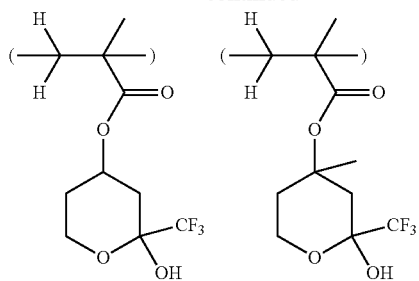
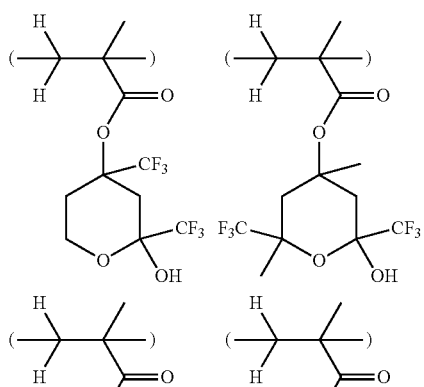
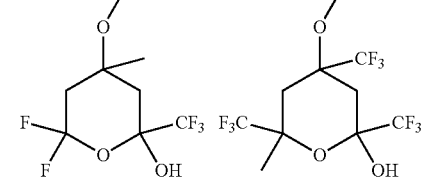
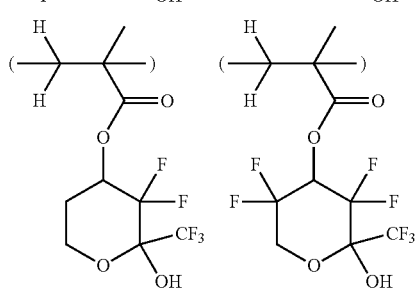
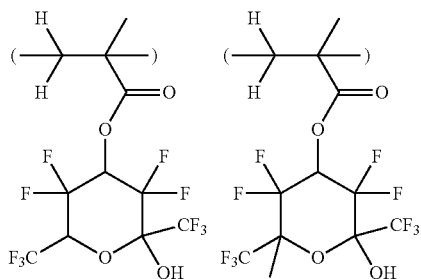
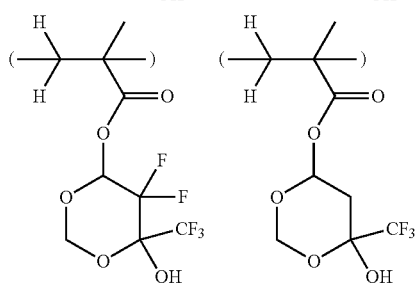
-continued
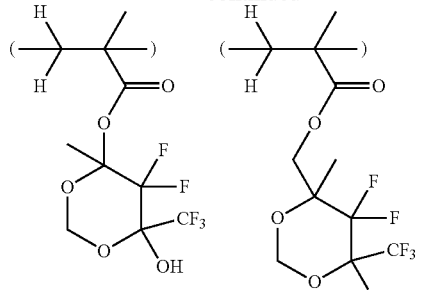
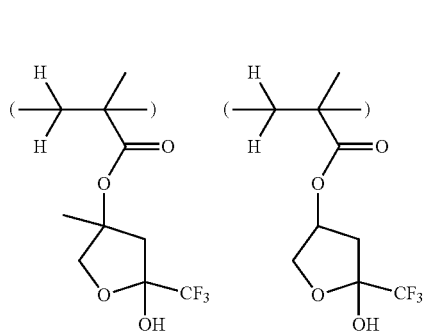
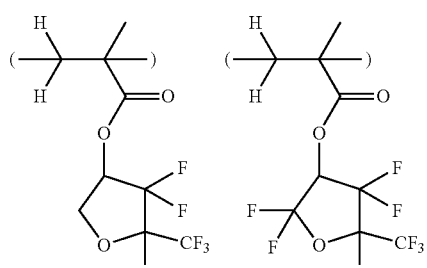
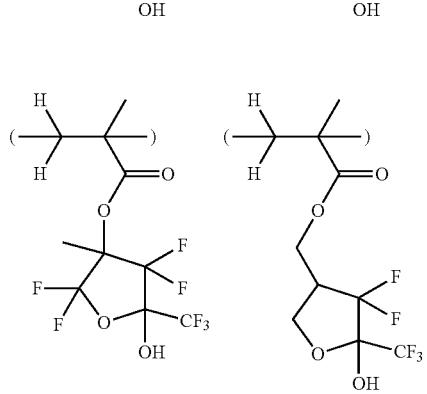
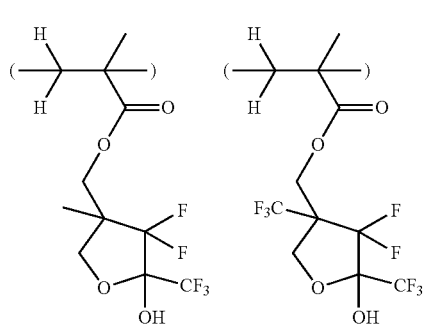

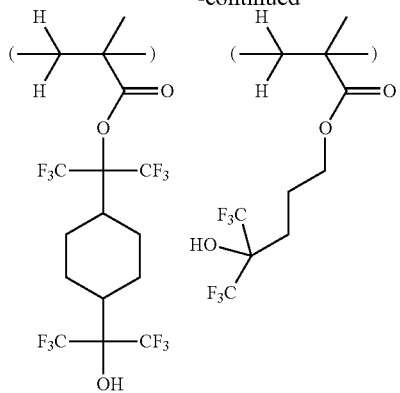
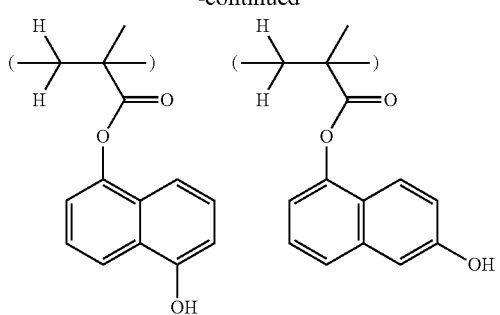
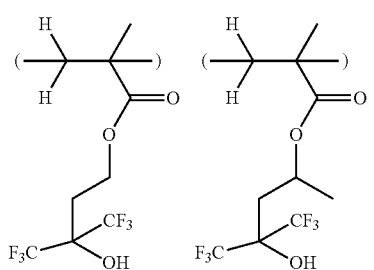
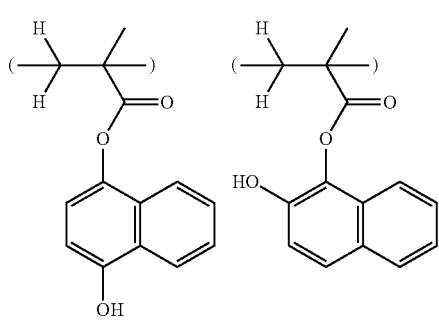
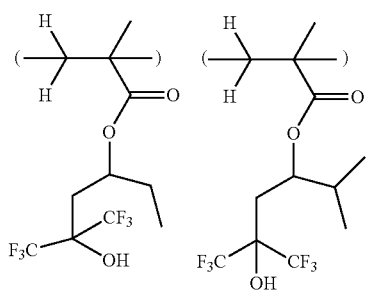
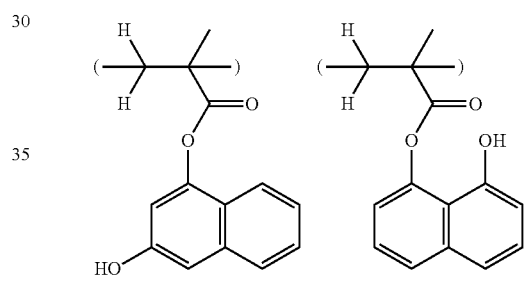
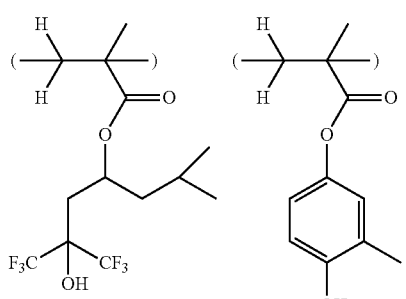
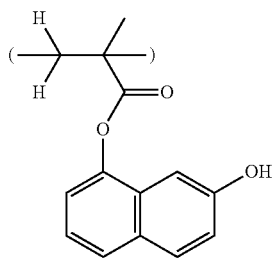
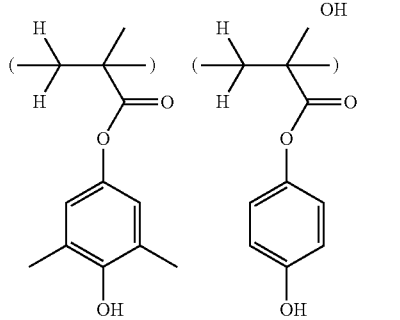
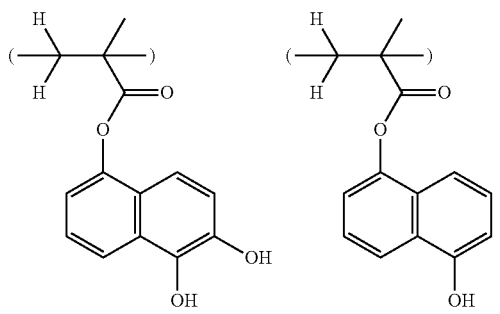

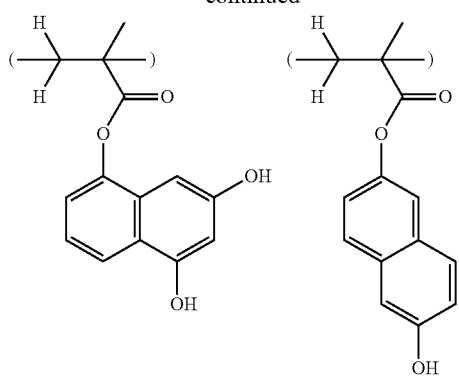
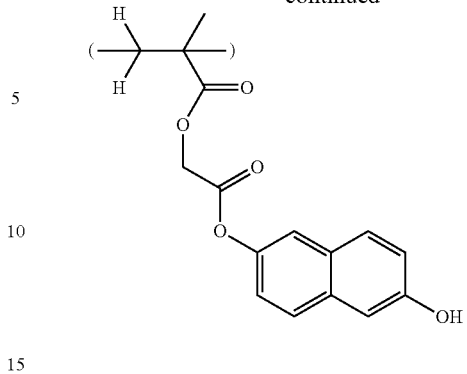
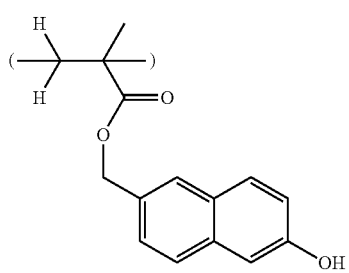
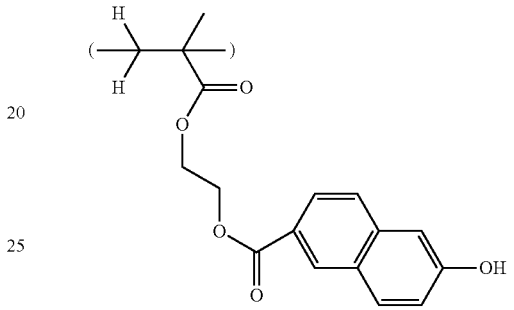
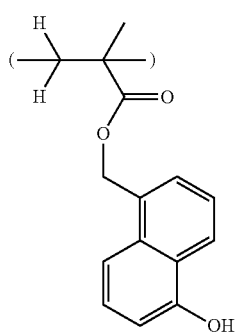
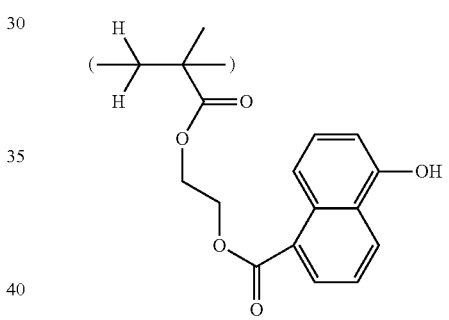
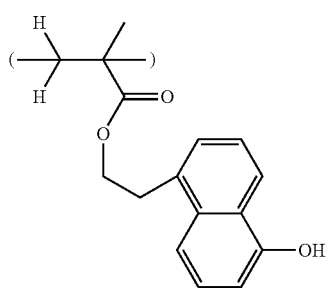
Of the recurring units having formula (3), those units having a lactone ring as the polar group are most preferred.
In addition to the recurring units having formulae (2) and (3), the polymer may further comprise recurring units having the general formula (d1) or (d2).
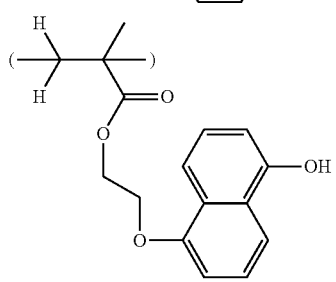
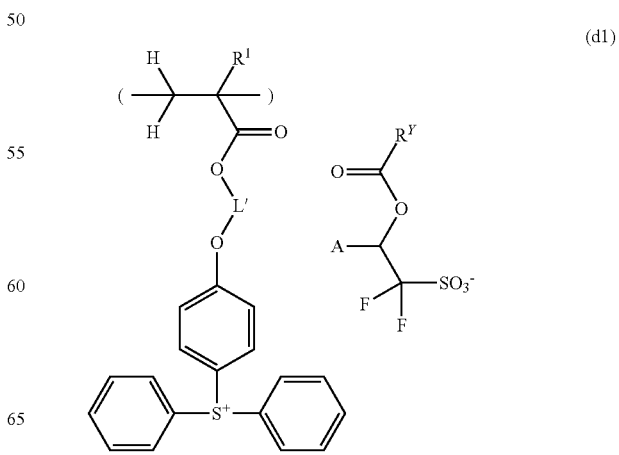

-continued

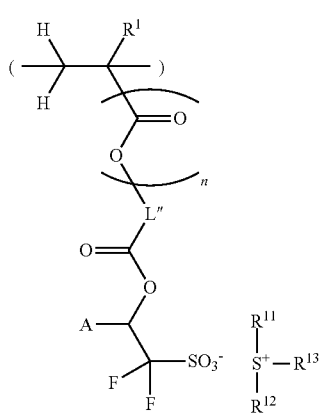
(d2)

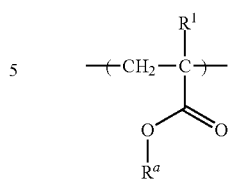
(10a)

Herein $R^1$ is as defined above. $R^a$ is a straight, branched or cyclic $C_1$-$C_{20}$ monovalent hydrocarbon group which may be substituted with or separated by a heteroatom, with the proviso that the monovalent hydrocarbon group of $R^a$ has 1 to 4 substituent groups of the general formula (10b):

Herein $R^1$, $R^{11}$, $R^{12}$, and $R^{13}$ are as defined above. L' is a $C_2$-$C_5$ alkylene group. $R^Y$ is a $C_1$-$C_{20}$ linear or $C_3$-$C_{20}$ branched or cyclic monovalent hydrocarbon group which may be substituted with or separated by a heteroatom. A is hydrogen or trifluoromethyl. L" is a single bond or a $C_1$-$C_{20}$ linear or $C_3$-$C_{20}$ branched or cyclic divalent hydrocarbon group which may be substituted with or separated by a heteroatom. The subscript n is 0 or 1, with the proviso that n must be 0 when L" is a single bond.

In formula (d1), $R^1$ is as defined and exemplified above. L' is a $C_2$-$C_5$ alkylene group, preferably ethylene, propylene or butylene. A is hydrogen or trifluoromethyl, preferably trifluoromethyl. $R^Y$ is a $C_1$-$C_{20}$ linear or $C_3$-$C_{20}$ branched or cyclic monovalent hydrocarbon group which may be substituted with or separated by a heteroatom.

The anion moiety in formula (d1) is exemplified by those structures illustrated in JP-A 2010-113209 and JP-A 2007-145797.

In formula (d2), $R^1$, $R^{11}$, $R^{12}$, $R^{13}$ and A are as defined and exemplified above. L" is a single bond or a $C_1$-$C_{20}$ linear or $C_3$-$C_{20}$ branched or cyclic divalent hydrocarbon group which may be substituted with or separated by a heteroatom. The subscript n is 0 or 1, with the proviso that n must be 0 when L" is a single bond.

The anion moiety in formula (d2) wherein A is hydrogen is exemplified by those structures illustrated in JP-A 2010-116550. The anion moiety in formula (d2) wherein A is trifluoromethyl is exemplified by those structures illustrated in JP-A 2010-077404.

While the polymer as the base resin in the resist composition is characterized by comprising recurring units of formulae (2) and (3) and optionally recurring units of formula (d1) or (d2), it may have further copolymerized therein recurring units of the structure having a hydroxyl group protected with an acid labile group. The recurring unit of the structure having a hydroxyl group protected with an acid labile group is not particularly limited as long as it has one or more protected hydroxyl-bearing structure such that the protective group may be decomposed to generate a hydroxyl group under the action of acid. Inter alia, recurring units of the structure having the general formula (10a) are preferred.

(10b)

wherein $R^b$ is an acid labile group.

Examples of the recurring unit of formula (10a) are shown below, but not limited thereto.

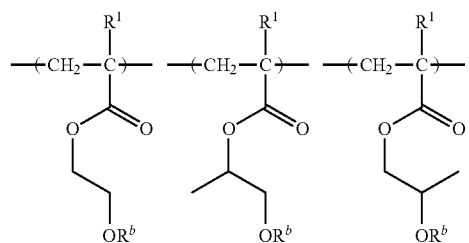

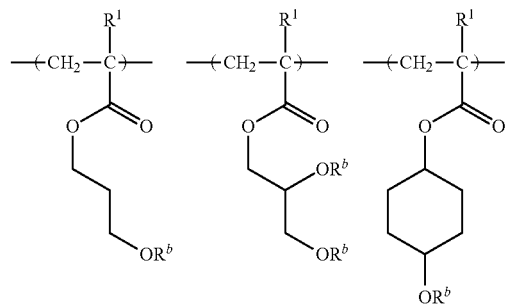

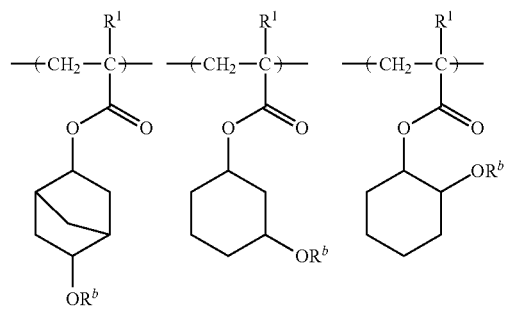

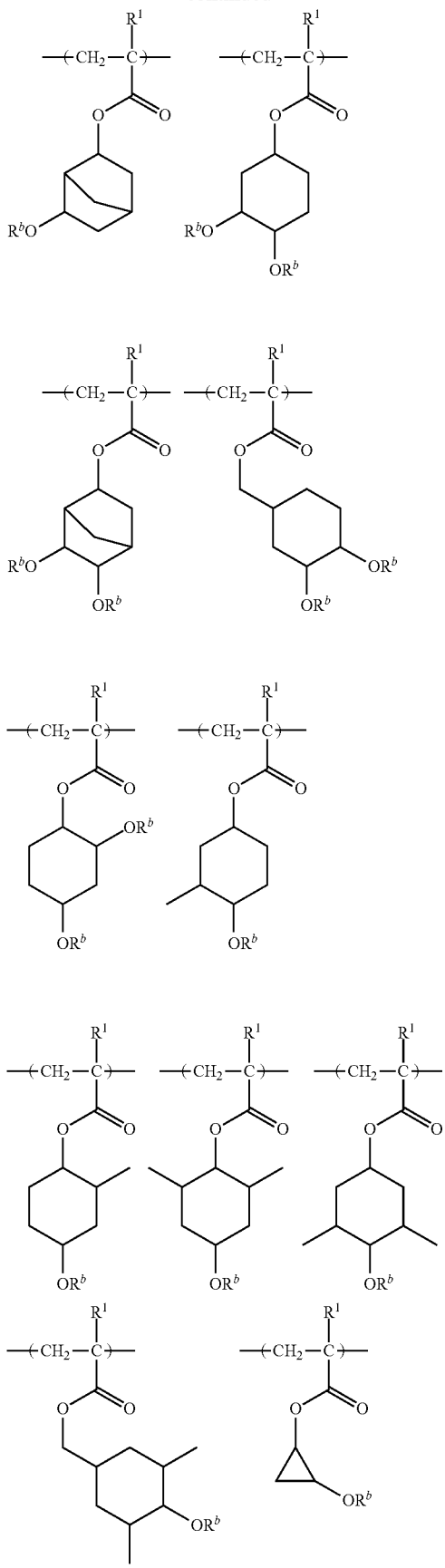
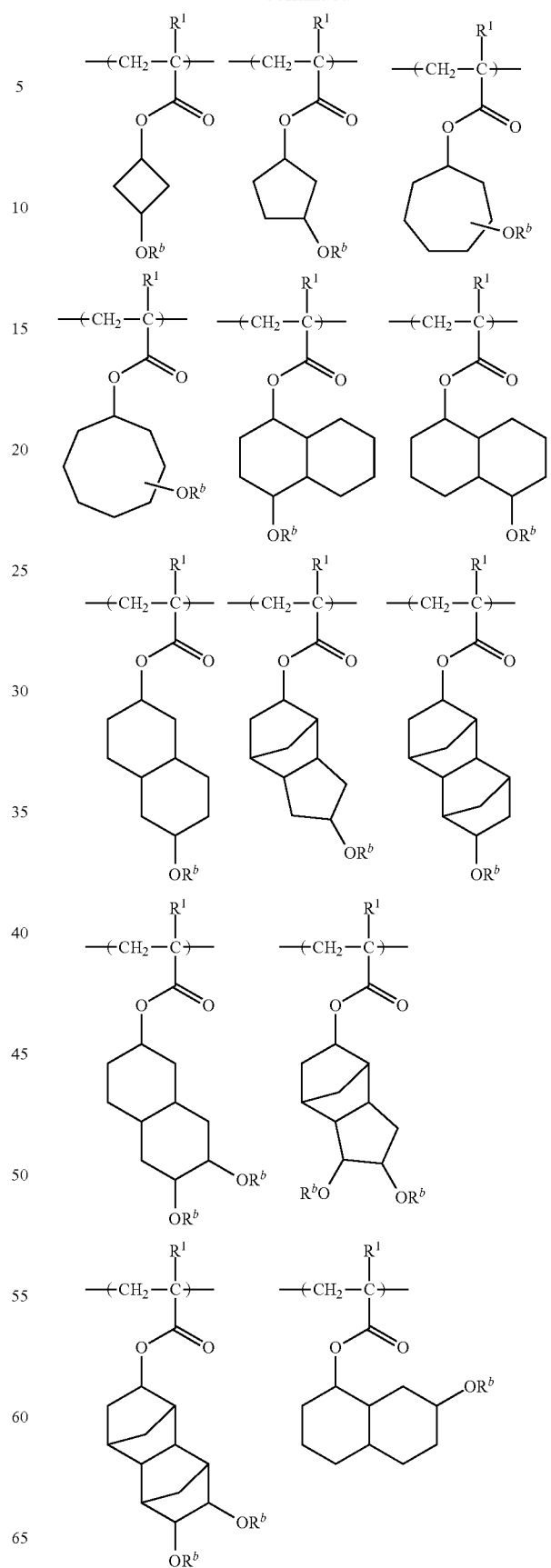

-continued
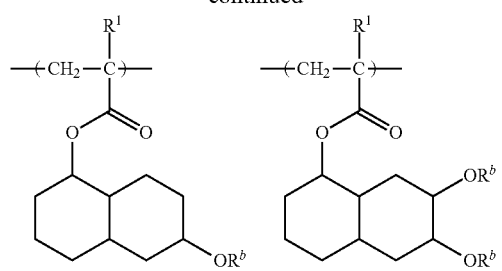
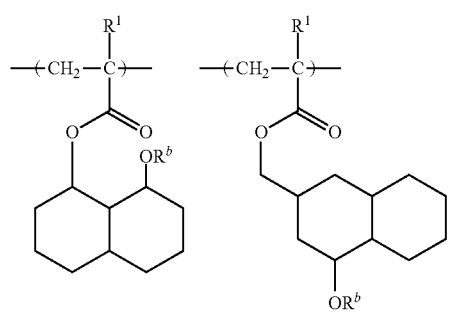
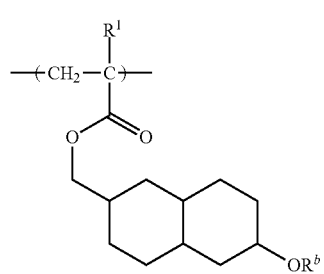
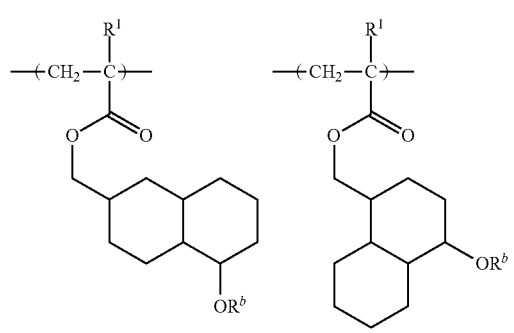
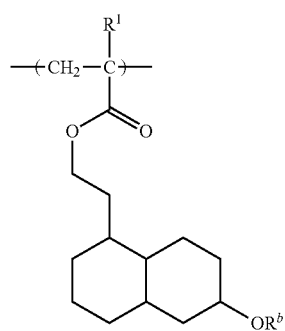
-continued
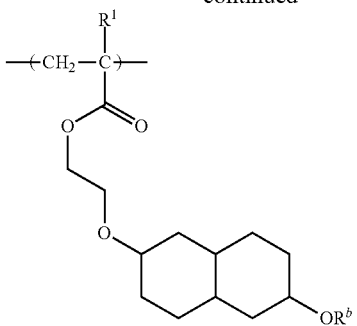
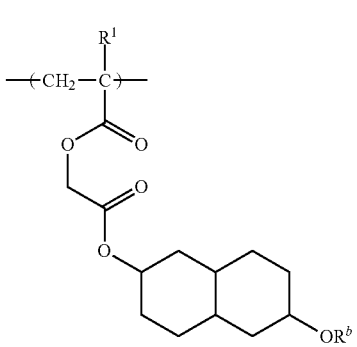
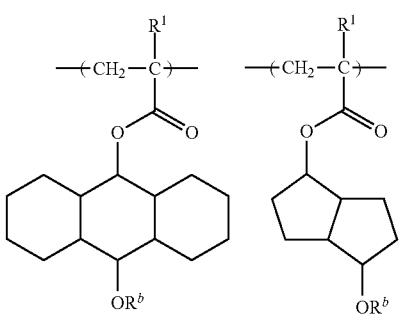
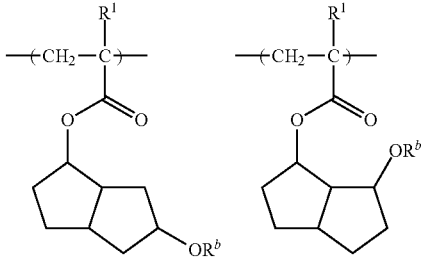
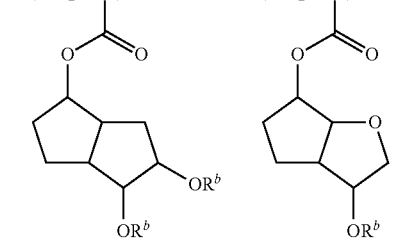

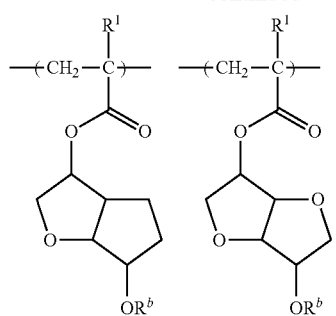
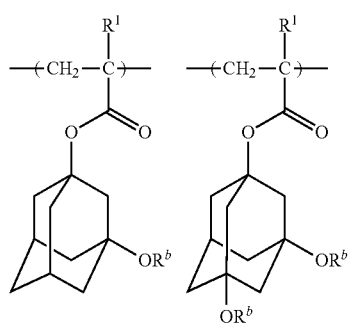
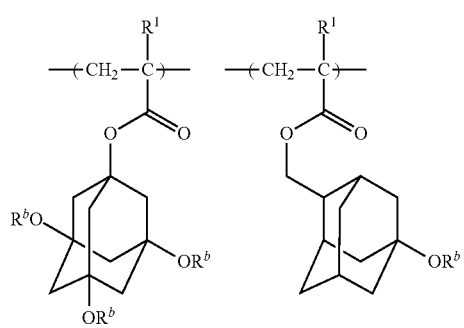
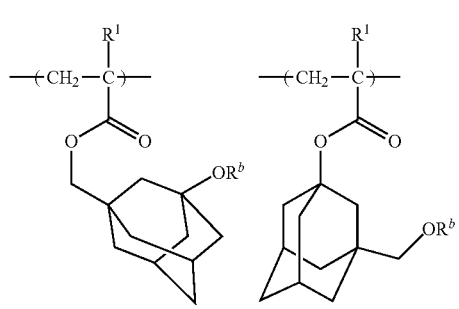
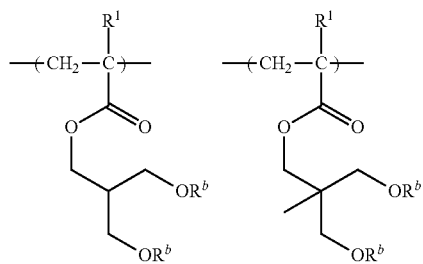
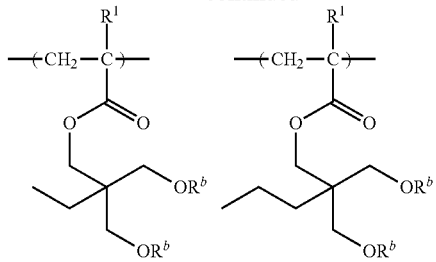
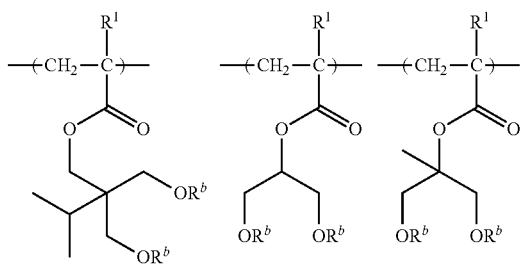
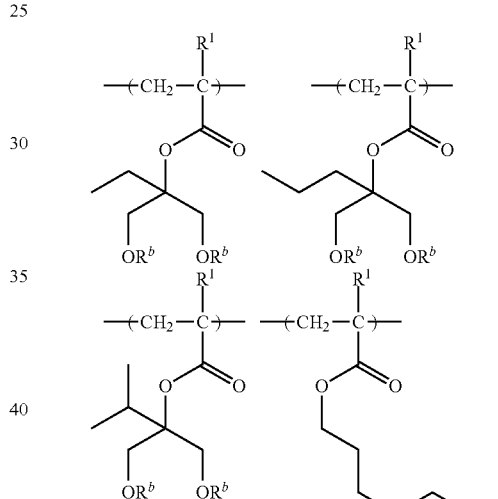
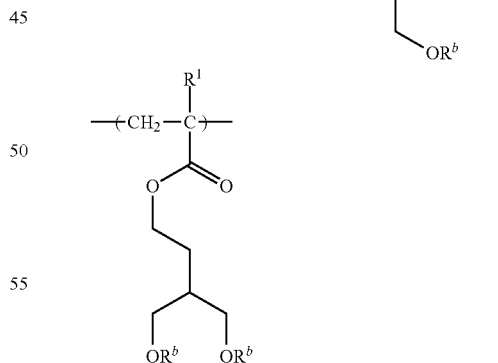

Herein $R^1$ is as defined above, and $R^b$ is as defined for the acid labile group XA.

The structure of the acid labile group $R^b$ in formula (10b) is not particularly limited as long as it is deprotected to generate a hydroxyl group under the action of acid. Typical acid labile groups are groups of acetal or ketal structure and alkoxycarbonyl groups, with their examples being shown below.

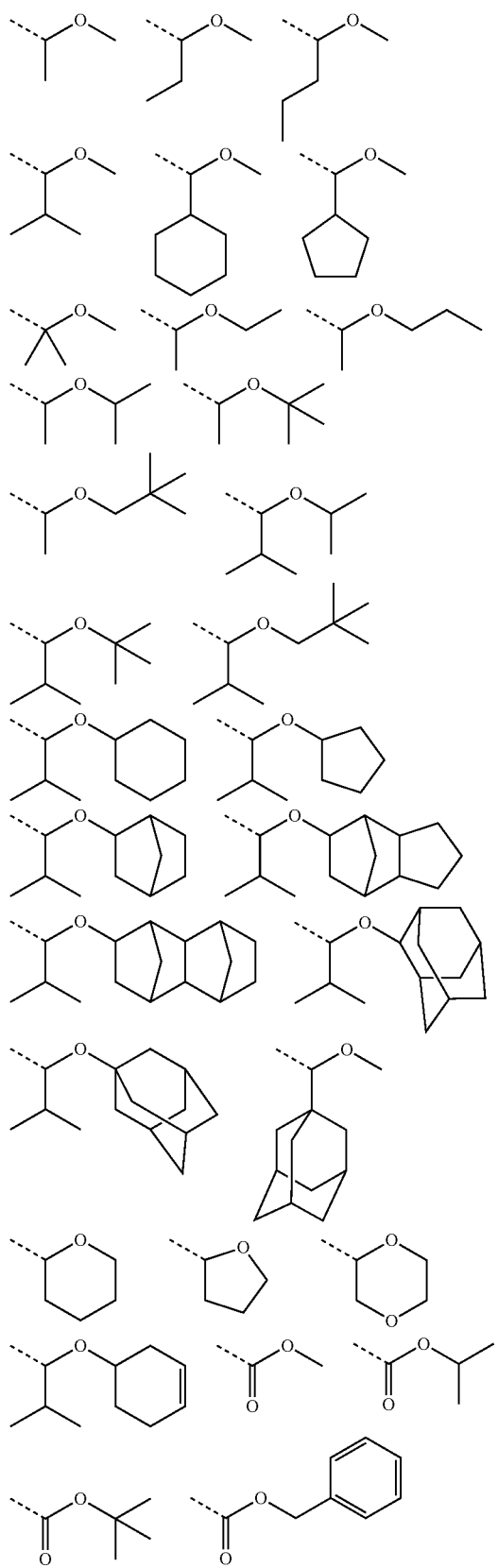
Of the acid labile group $R^b$ in formula (10b), preferred are alkoxymethyl groups having the general formula (10c):
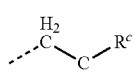
(10c)
wherein $R^c$ is a monovalent hydrocarbon group such as a straight, branched or cyclic $C_1$-$C_{15}$ alkyl group.
Examples of the acid labile group of formula (10c) are shown below, but not limited thereto.
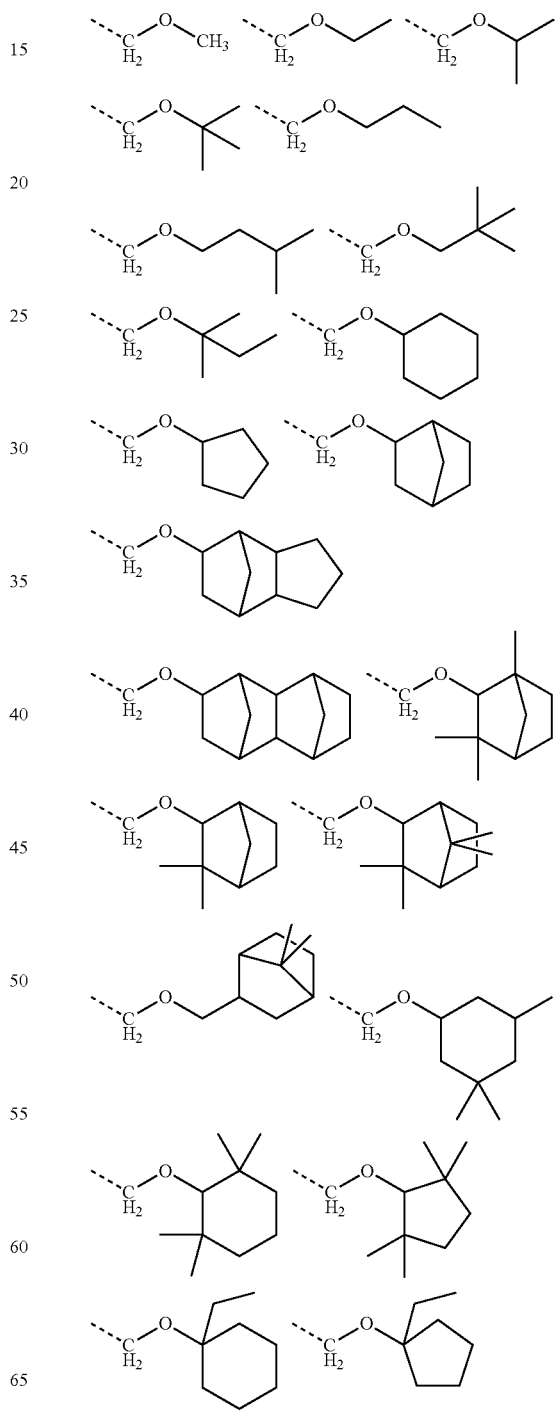

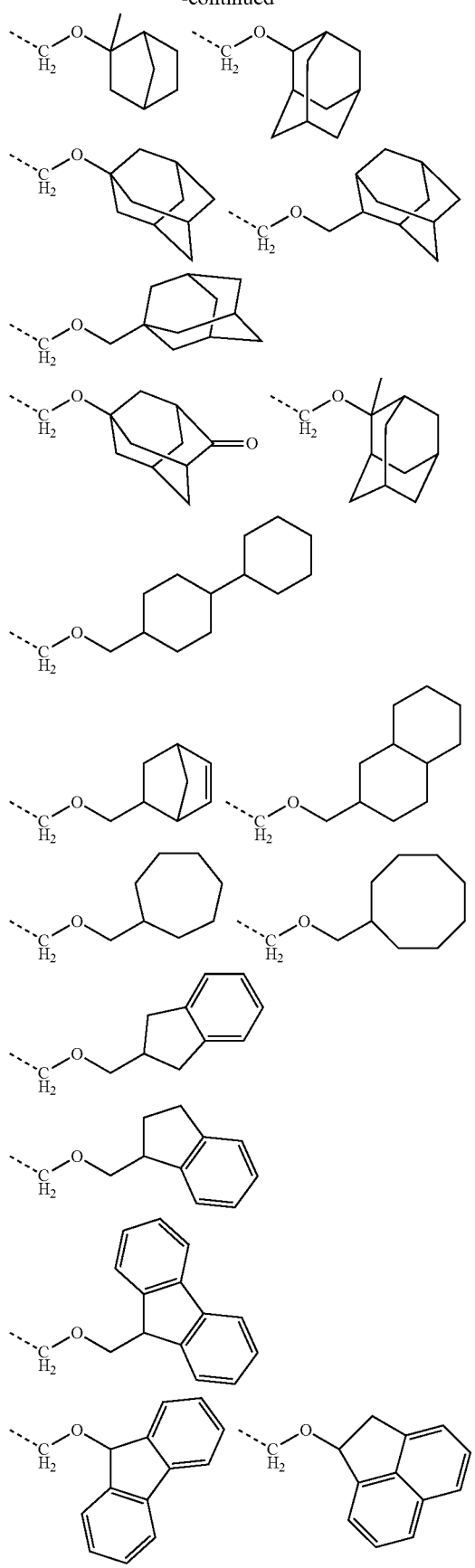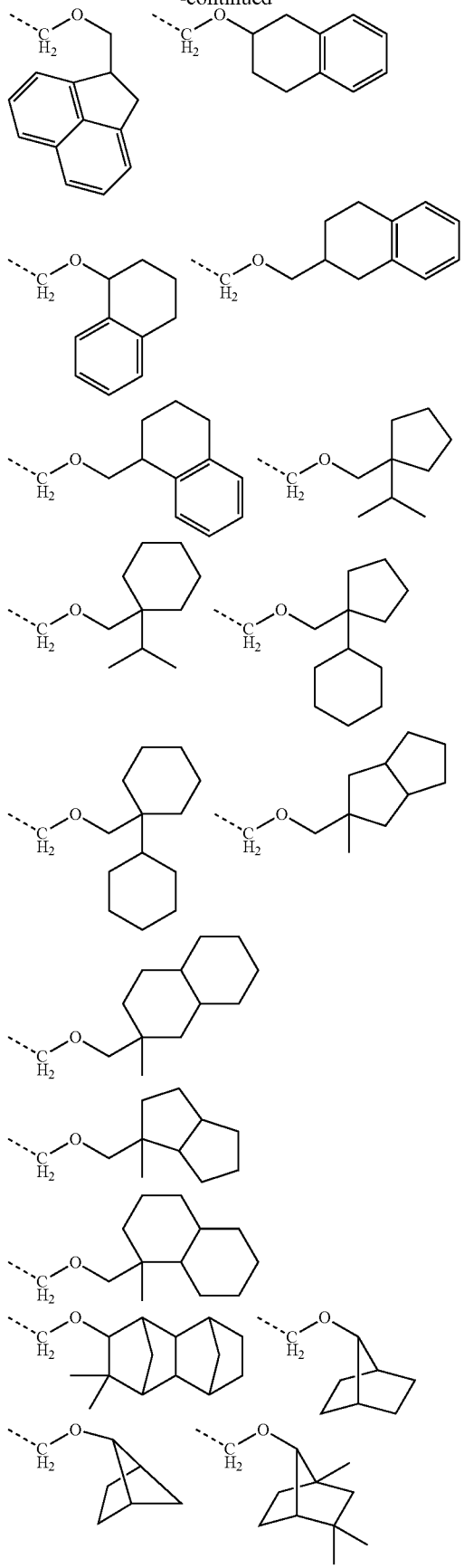

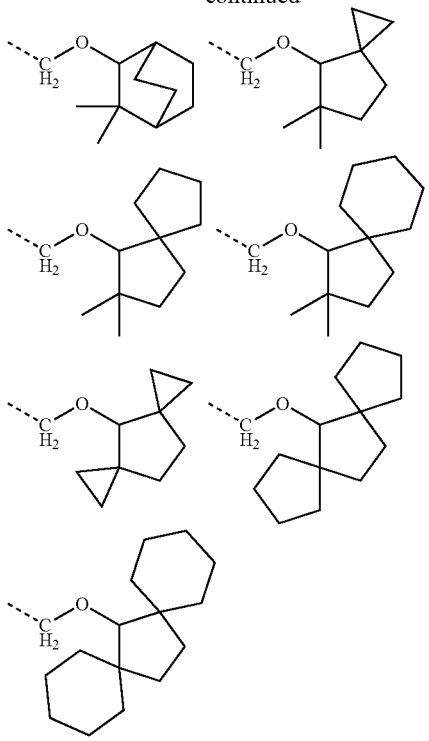

In addition to the foregoing units, the polymer may further comprise recurring units derived from other monomers, for example, substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[6.2.1.1$^{3,6}$.0$^{2,7}$]dodecene derivatives, unsaturated acid anhydrides such as itaconic anhydride, and other monomers. Also, hydrogenated ROMP polymers as described in JP-A 2003-066612 may be used.

The polymer generally has a weight average molecular weight (Mw) of 1,000 to 500,000, and preferably 3,000 to 100,000, as measured by gel permeation chromatography (GPC) versus polystyrene standards. Outside the range, there may result an extreme drop of etch resistance, and a drop of resolution due to difficulty to gain a dissolution rate difference before and after exposure.

The general method of synthesizing the polymer is, for example, by dissolving one or more unsaturated bond-bearing monomers in an organic solvent, adding a radical initiator, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours. The acid labile group that has been incorporated in the monomer may be kept as such, or polymerization may be followed by protection or partial protection.

While the base resin (B) comprises recurring units derived from monomers, the molar fractions of respective units preferably fall in the following range (mol %), but are not limited thereto:

(I) 1 to 60 mol %, more preferably 5 to 50 mol %, even more preferably 10 to 50 mol % of constituent units of at least one type having formula (2),
(II) 40 to 99 mol %, more preferably 50 to 95 mol %, even more preferably 50 to 90 mol % of constituent units of at least one type having formula (3), and optionally,
(III) 0 to 30 mol %, more preferably 0 to 20 mol %, and even more preferably 0 to 10 mol % of constituent units of at least one type having formula (d1) or (d2), and optionally,
(IV) 0 to 80 mol %, more preferably 0 to 70 mol %, and even more preferably 0 to 50 mol % of constituent units of at least one type derived from another monomer(s).

(C) Second Photoacid Generator

While the PAG having formula (1a) or (1b) is essential for the inventive resist composition, the composition may further comprise another PAG (other than the PAG having formula (1a) or (1b)), preferably a second PAG having the general formula (4).

Herein $R^2$, $R^3$ and $R^4$ are as defined and exemplified above for $R^{11}$, $R^{12}$, and $R^{13}$, and $X^-$ is an anion having the general formula (5), (6), (7) or (8).

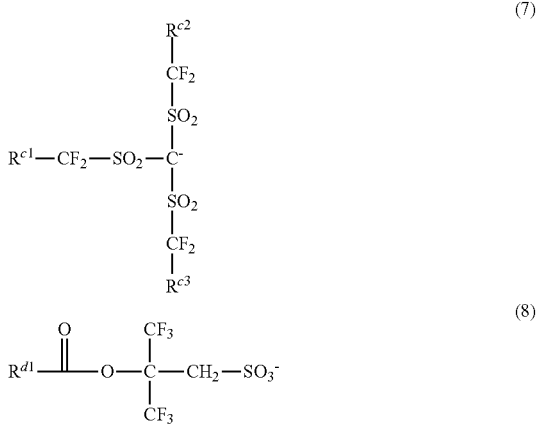

Herein $R^{a1}$, $R^{b1}$, $R^{b2}$, $R^{c1}$, $R^{c2}$, and $R^{c3}$ are each independently fluorine, or a $C_1$-$C_{40}$ straight or $C_3$-$C_{40}$ branched or cyclic monovalent hydrocarbon group which may be substituted with or separated by a heteroatom. $R^{b1}$ and $R^{b2}$, and $R^{c1}$ and $R^{c2}$ may bond together to form a ring with the carbon atoms to which they are attached and the carbon atom therebetween, if any. $R^{d1}$ is a $C_1$-$C_{40}$ straight or $C_3$-$C_{40}$ branched or cyclic monovalent hydrocarbon group which may be substituted with or separated by a heteroatom.

In formula (5), $R^{a1}$ is fluorine, or a $C_1$-$C_{40}$ straight or $C_3$-$C_{40}$ branched or cyclic monovalent hydrocarbon group which may be substituted with or separated by a heteroatom.

Of the anions having formula (5), preferred is a structure having the general formula (5'):

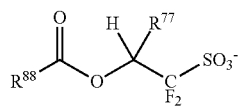
(5')

wherein $R^{77}$ is hydrogen or trifluoromethyl, and $R^{88}$ is a $C_1$-$C_{30}$ straight or $C_3$-$C_{30}$ branched or cyclic monovalent hydrocarbon group which may be substituted with or separated by a heteroatom.

In formula (5'), $R^{77}$ is hydrogen or trifluoromethyl, preferably trifluoromethyl. $R^{88}$ is a $C_1$-$C_{30}$ straight or $C_3$-$C_{30}$ branched or cyclic monovalent hydrocarbon group which may be substituted with or separated by a heteroatom. The heteroatom in $R^{88}$ is preferably selected from among oxygen, nitrogen, sulfur, and halogen, with oxygen being more preferred. Of the monovalent hydrocarbon groups $R^{88}$, those groups of 6 to 30 carbon atoms are preferred for achieving a high resolution in fine-size pattern formation. Examples of the group $R^{88}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having formula (5'), reference should be made to JP-A 2007-145797, 2008-106045, 2009-007327, and 2009-258695.

Also useful are the sulfonium salts described in JP-A 2010-215608, 2012-041320, 2012-106986, and 2012-153644.

Preferred examples of the relevant PAG are given below.

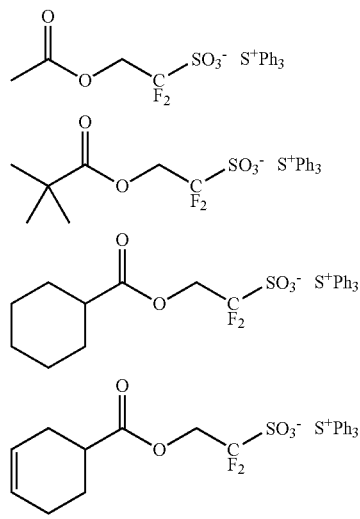

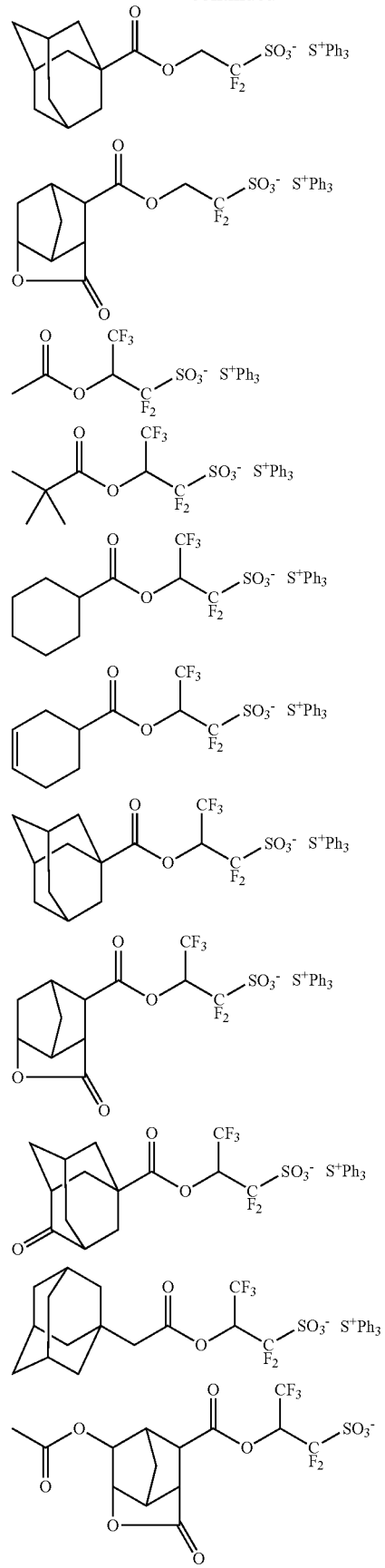

79
-continued
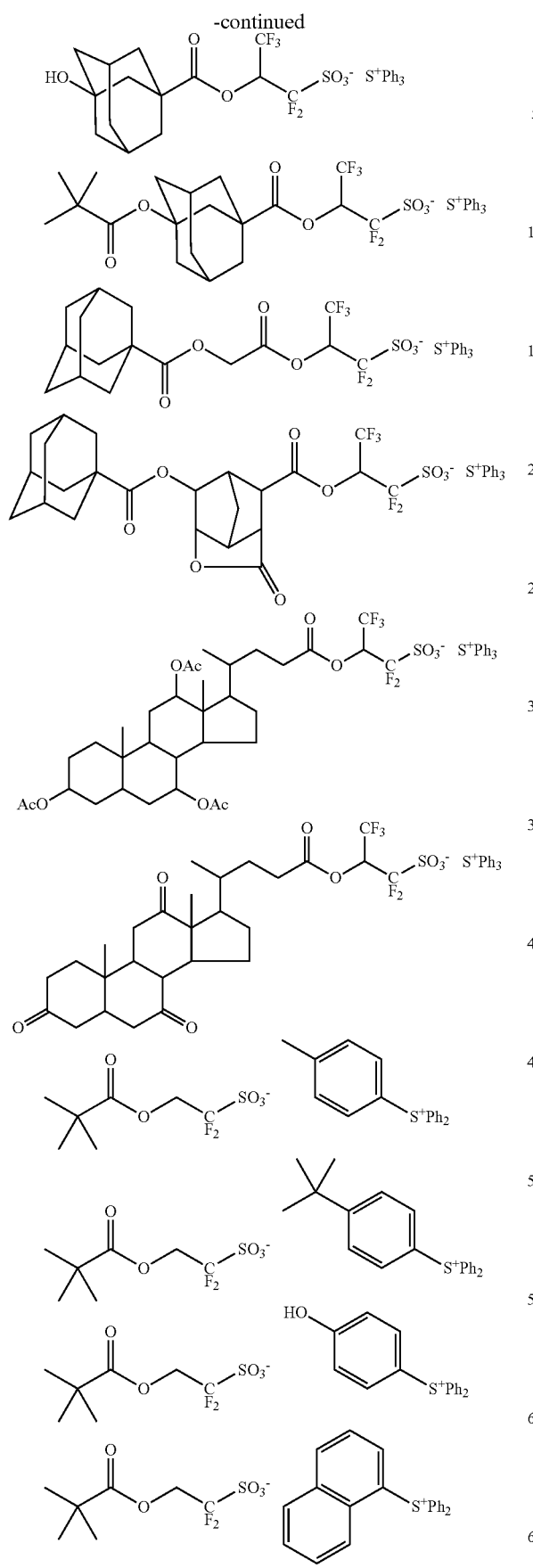
80
-continued
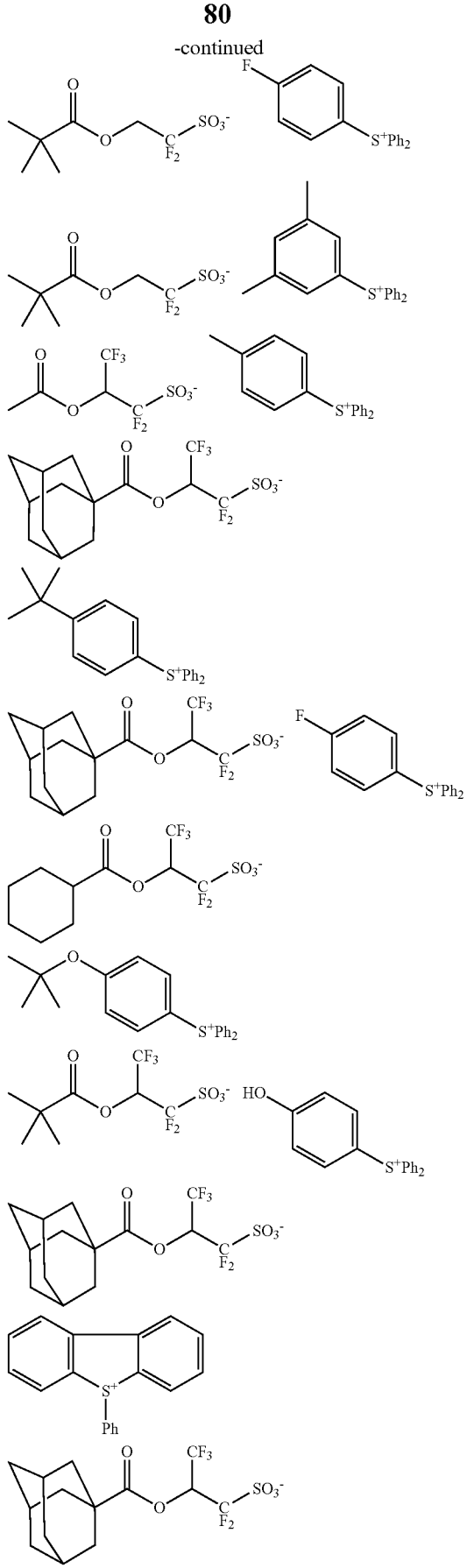

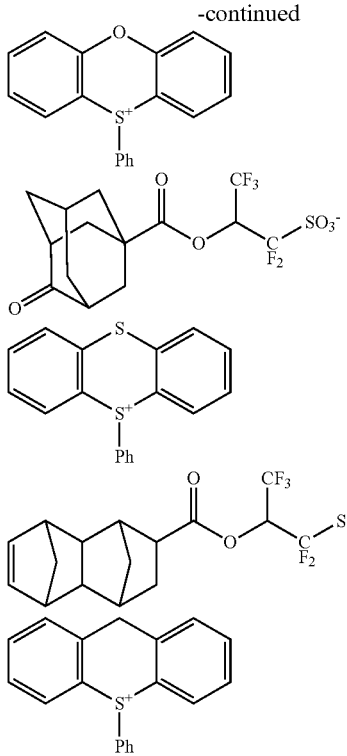

domethyl, trifluoromethyl, (2-methoxyethoxy)methyl, acetoxymethyl, 2-carboxy-1-cyclohexyl, 2-oxopropyl, 4-oxo-1-adamantyl, and 3-oxocyclohexyl.

With respect to the synthesis of the sulfonium salt having the anion of formula (8), reference should be made to JP-A 2010-215608.

Preferred examples of the relevant PAG are given below.

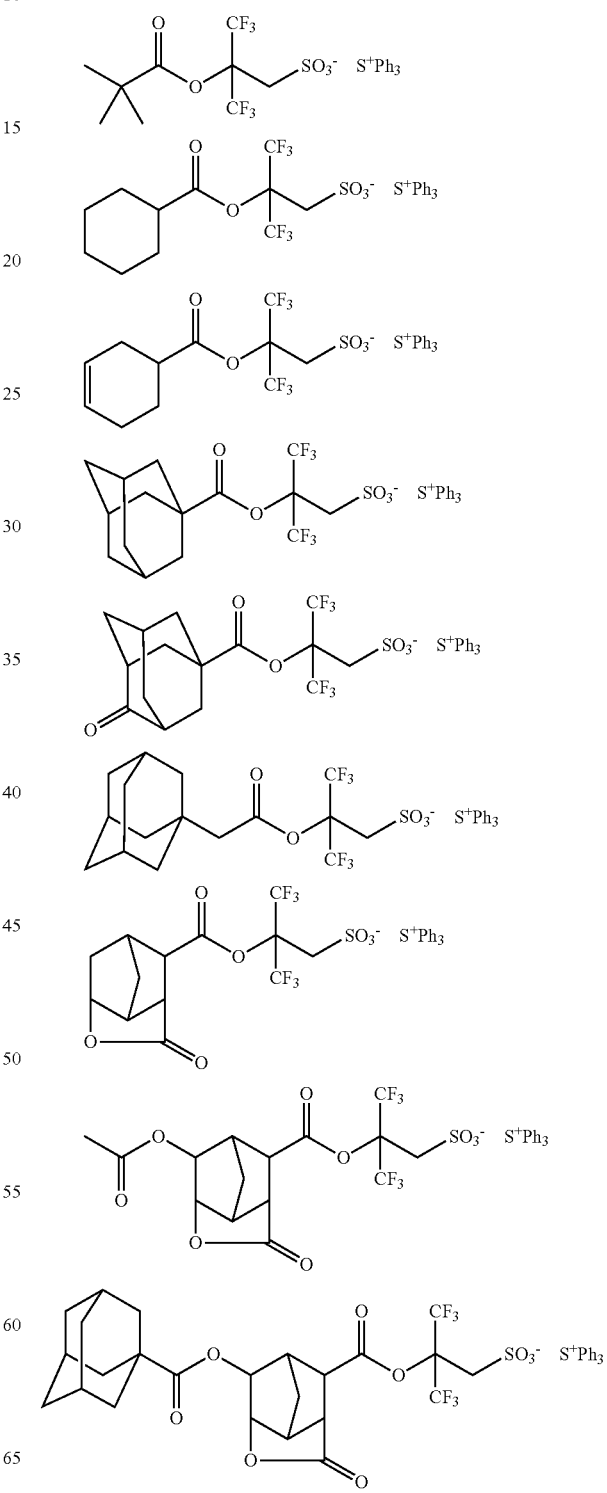

In formula (6), $R^{b1}$ and $R^{b2}$ are each independently fluorine or a $C_1$-$C_{40}$ straight or $C_3$-$C_{40}$ branched or cyclic monovalent hydrocarbon group which may be substituted with or separated by a heteroatom. Suitable groups are as exemplified above for $R^{a1}$. Inter alia, fluorine or $C_1$-$C_4$ straight fluoroalkyl groups are preferred. $R^{b1}$ and $R^{b2}$ may bond together to form a ring with the linkage (—$CF_2$—$SO_2$—$N^-$—$SO_2$—$CF_2$—) to which they are attached, and preferably a combination of $R^{b1}$ and $R^{b2}$ is fluoroethylene or fluoropropylene to form a ring structure.

In formula (7), $R^{c1}$, $R^{c2}$ and $R^{c3}$ are each independently fluorine or a $C_1$-$C_{40}$ straight or $C_3$-$C_{40}$ branched or cyclic monovalent hydrocarbon group which may be substituted with or separated by a heteroatom. Suitable groups are as exemplified above for $R^{a1}$. Inter alia, fluorine or $C_1$-$C_4$ straight fluoroalkyl groups are preferred. $R^{c1}$ and $R^{c2}$ may bond together to form a ring with the linkage (—$CF_2$—$SO_2$—$C^-$—$SO_2$—$CF_2$—) to which they are attached, and preferably a combination of $R^{c1}$ and $R^{c2}$ is fluoroethylene or fluoropropylene to form a ring structure.

In formula (8), $R^{d1}$ is a $C_1$-$C_{40}$ straight or $C_3$-$C_{40}$ branched or cyclic monovalent hydrocarbon group which may be substituted with or separated by a heteroatom. The heteroatom in $R^{d1}$ is preferably selected from among oxygen, nitrogen, sulfur, and halogen, with oxygen being more preferred. Of the monovalent hydrocarbon groups $R^{d1}$, those groups of 6 to 30 carbon atoms are preferred for achieving a high resolution in fine-size pattern formation. Examples of the group $R^{d1}$ include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetami-

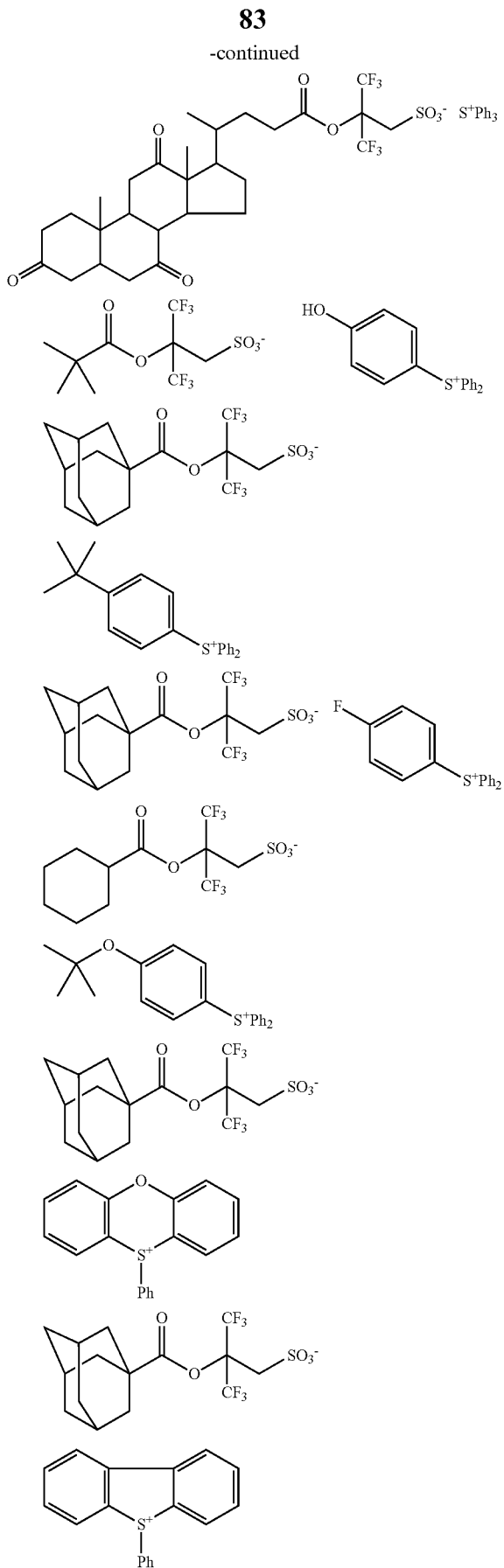
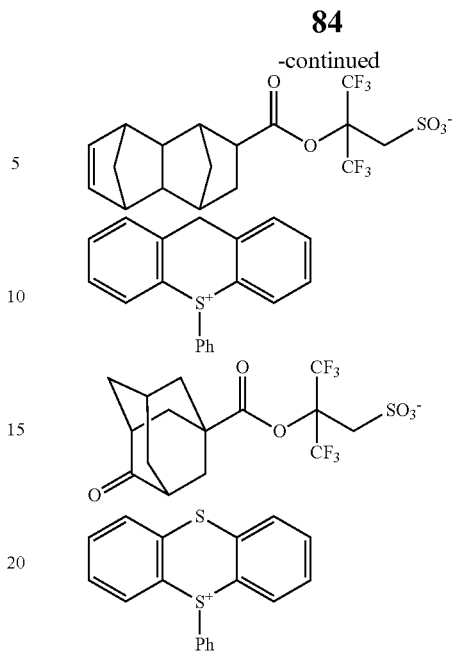

The compound having the anion of formula (8) has a sufficient acid strength to cleave acid labile groups in the polymer because it is free of fluorine at α-position of sulfo group, but has two trifluoromethyl groups at β-position. Thus the compound is a useful PAG.

Of the second PAGs, those compounds of formula (5') and those compounds having the structure of formula (8) are most preferred because of slow acid diffusion and high solubility in the resist solvent.

An appropriate amount of the second PAG (C) added is 0 to 40 parts by weight, and when used, 0.1 to 40 parts, more preferably 0.1 to 20 parts by weight per 100 parts by weight of the base resin. An excessive amount may bring about a drop of resolution, and leave foreign particles after resist development or during separation.

(D) Quencher

The quencher (D) may be added to the resist composition. As used herein, the "quencher" refers to a compound capable of suppressing the rate of diffusion when the acid generated by the PAG diffuses within the resist film. Suitable quenchers include primary, secondary and tertiary amine compounds, specifically amine compounds having a hydroxyl, ether, ester, lactone, cyano or sulfonate group, as described in JP-A 2008-111103, paragraphs [0146] to [0164] (U.S. Pat. No. 7,537,880), and compounds having primary or secondary amine protected as a carbamate group, as described in JP 3790649.

The quencher may be used alone or in admixture of two or more. An appropriate amount of the quencher is 0.001 to 12 parts, preferably 0.01 to 8 parts by weight, per 100 parts by weight of the base resin. The inclusion of quencher facilitates adjustment of resist sensitivity and holds down the rate of acid diffusion within the resist film, resulting in better resolution. In addition, it suppresses changes in sensitivity following exposure and reduces substrate and environment dependence, as well as improving the exposure latitude and the pattern profile. The inclusion of quencher is also effective for improving adhesion to the substrate.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid as described in JP 3991462 may be used as the quencher, provided that the counter anion is a conjugated base of weak acid. As used herein, the weak acid indicates an acidity insufficient to deprotect an acid labile group from an acid labile group-containing unit in the base resin. The above onium salt functions as a quencher when used in combination with an onium salt type photoacid generator having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a photoacid generator capable of generating a strong acid is an onium salt, an exchange from the strong acid generated upon exposure to high-energy radiation to a weak acid as above can take place, but it never happens that the weak acid generated upon exposure to high-energy radiation collides with the unreacted onium salt capable of generating a strong acid to induce a salt exchange. This is because of a likelihood of an onium cation forming an ion pair with a stronger acid anion.

Also an onium salt having a nitrogen-containing substituent group may be used together. This compound functions as a quencher in the unexposed region, but as a so-called photo-degradable base in the exposed region because it loses the quencher function in the exposed region due to neutralization thereof with the acid generated by itself. Using a photo-degradable base, the contrast between exposed and unexposed regions can be further enhanced. With respect to the photo-degradable base, reference may be made to JP-A 2009-109595 and 2012-046501, for example.

(E) Organic Solvent

Component (E) may be any organic solvent as long as the polymer, PAG, quencher and other additives are soluble therein. Examples of the organic solvent are described in JP-A 2008-111103, paragraphs [0144] to [0145] (U.S. Pat. No. 7,537,880). Specifically, exemplary solvents include ketones such as cyclohexanone and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof. Where an acid labile group of acetal form is used, a high-boiling alcohol solvent such as diethylene glycol, propylene glycol, glycerol, 1,4-butanediol or 1,3-butanediol may be added for accelerating deprotection reaction of acetal. Of the above organic solvents, it is recommended to use 1-ethoxy-2-propanol, PGMEA, cyclohexanone, γ-butyrolactone, and mixtures thereof because the acid generator is most soluble therein.

An appropriate amount of the organic solvent used is 200 to 7,000 parts, more preferably 400 to 5,000 parts by weight per 100 parts by weight of the base resin.

(F) Surfactant

Component (F) is a surfactant which is insoluble or substantially insoluble in water and soluble in alkaline developer, and/or a surfactant which is insoluble or substantially insoluble in water and alkaline developer (hydrophobic resin). For the surfactant (F) which can be added to the resist composition, reference should be made to those compounds defined as component (S) in JP-A 2010-215608 and JP-A 2011-016746.

While many examples of the surfactant which is insoluble or substantially insoluble in water and alkaline developer are described in these patent documents, preferred examples are FC-4430, Surflon S-381, Surfynol E1004, KH-20 and KH-30, which may be used alone or in admixture. Partially fluorinated oxetane ring-opened polymers having the structural formula (surf-1) are also useful.

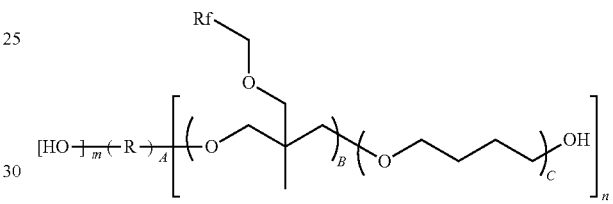

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

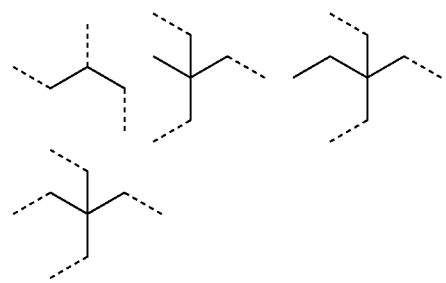

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. A is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist surface after spin coating for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water slippage. Suitable polymeric surfactants are shown below.

matic ring with the carbon atoms to which they are attached. In this event, $R^{117}$, $R^{118}$ and the carbon atoms to which they are attached together represent a trivalent organic group of 2 to 12 carbon atoms in total. $R^{119}$ is a single bond or a $C_1$-$C_4$ alkylene. $R^{120}$ is each independently a single bond, —O—, or —$CR^{114}R^{114}$—. $R^{121}$ is a straight or branched $C_1$-$C_4$ alkylene group, or may bond with $R^{115}$ within a common monomer to form a $C_3$-$C_6$ non-aromatic ring with the carbon atom to which they are attached. $R^{122}$ is 1,2-ethylene, 1,3-propylene, or 1,4-butylene. Rf is a linear perfluoroalkyl group of 3 to 6 carbon atoms, typically 3H-perfluoropropyl, 4H-perfluorobutyl, 5H-perfluoropentyl, or 6H-perfluorohexyl. $X^2$ is each independently —C(=O)—O—, —O—, or —C(=O)—$R^{123}$—C(=O)—O—. $R^{123}$ is a straight, branched or cyclic $C_1$-$C_{10}$ alkylene group. The subscripts are in the range: $0 \leq (a'-1) < 1$, $0 \leq (a'-2) < 1$, $0 \leq (a'-3) < 1$, $0 < (a'-1)+(a'-2)+(a'-3) < 1$, $0 \leq b' < 1$, $0 \leq c' < 1$, and $0 < (a'-1)+(a'-2)+(a'-3)+b'+c' \leq 1$.

Examples of these units are shown below.

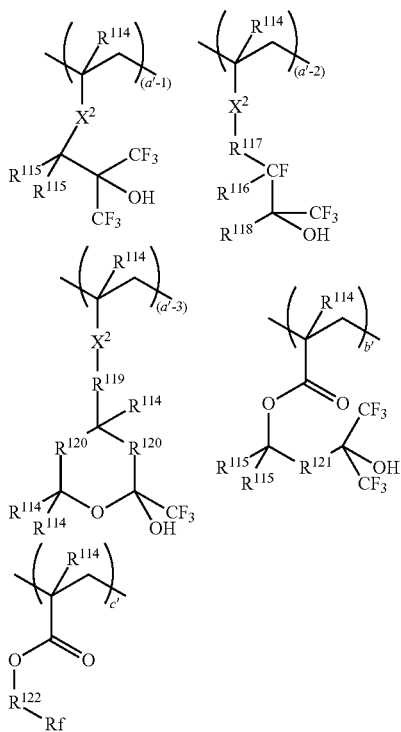

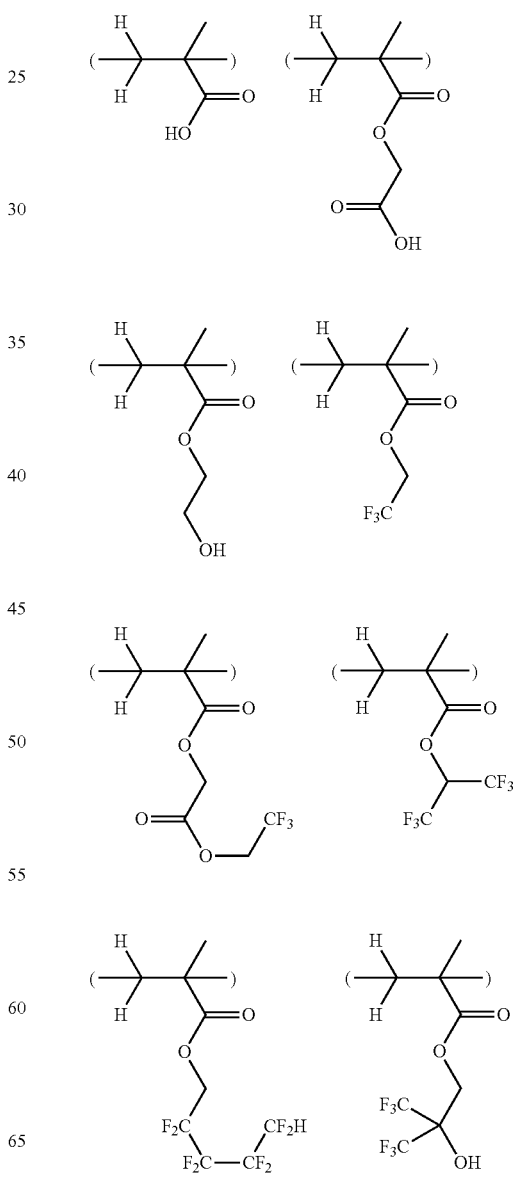

Herein $R^{114}$ is each independently hydrogen, fluorine, methyl or trifluoromethyl. $R^{115}$ is each independently hydrogen or a straight, branched or cyclic $C_1$-$C_{20}$ alkyl or fluoroalkyl group, or two $R^{115}$ in a common monomer may bond together to form a ring with the carbon atom to which they are attached, and in this event, they together represent a straight, branched or cyclic $C_2$-$C_{20}$ alkylene or fluoroalkylene group. $R^{116}$ is fluorine or hydrogen, or $R^{116}$ may bond with $R^{117}$ to form a non-aromatic ring of 3 to 10 carbon atoms in total with the carbon atom to which they are attached. $R^{117}$ is a straight, branched or cyclic $C_1$-$C_6$ alkylene group in which at least one hydrogen atom may be substituted by a fluorine atom. $R^{118}$ is a straight or branched $C_1$-$C_{10}$ alkyl group in which at least one hydrogen atom is substituted by a fluorine atom. Alternatively, $R^{117}$ and $R^{118}$ may bond together to form a non-aro-

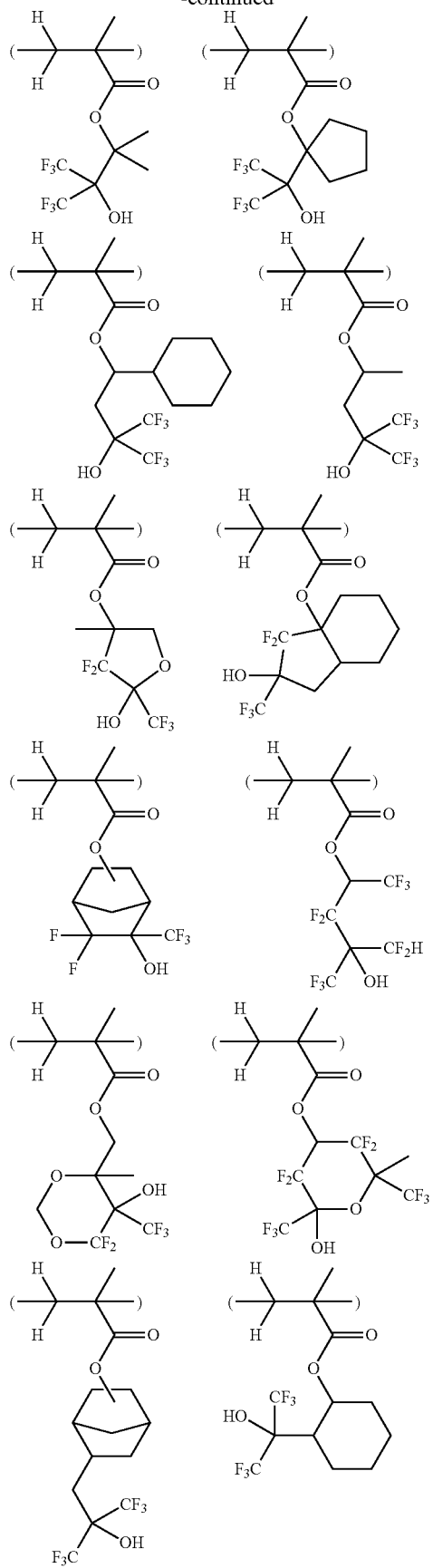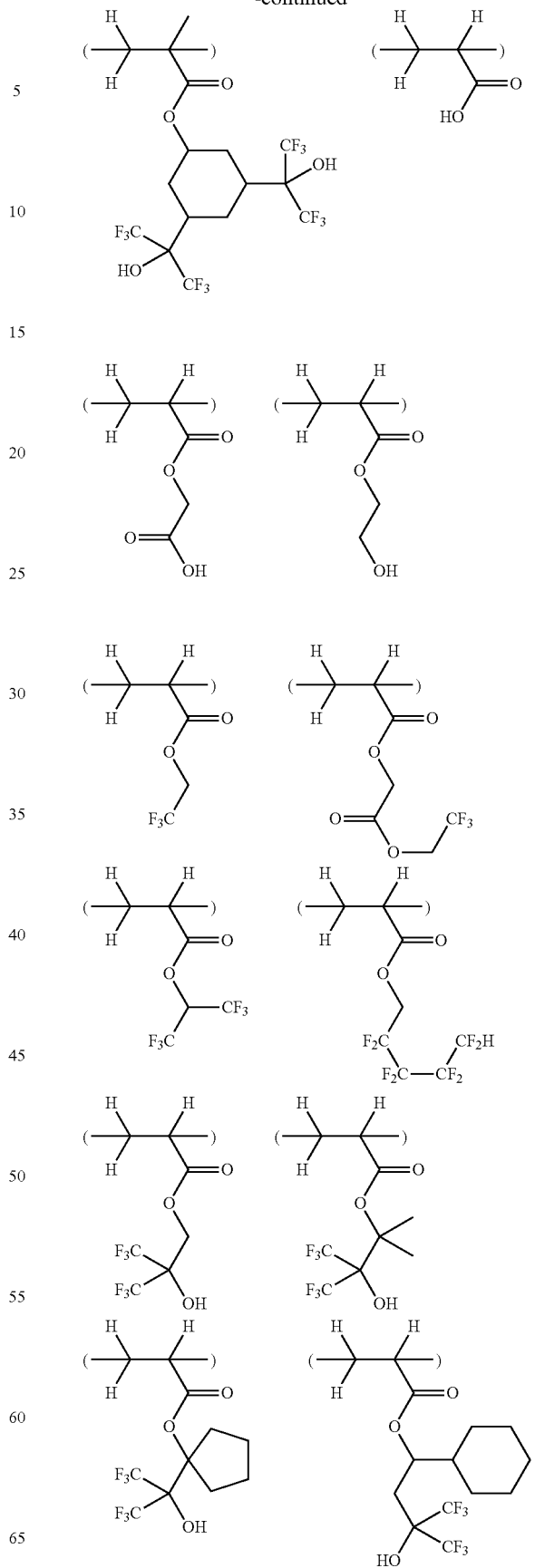

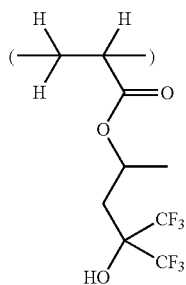 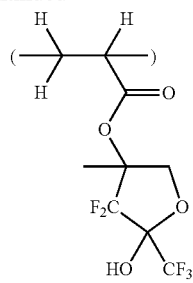

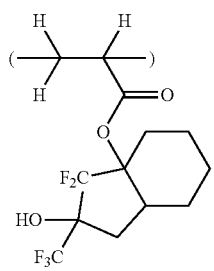 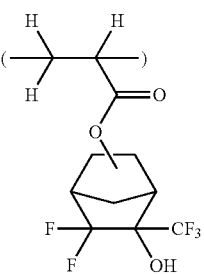

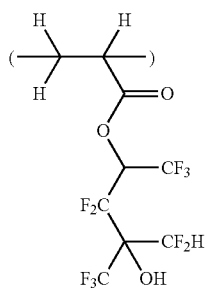 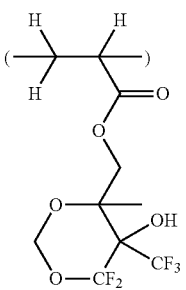

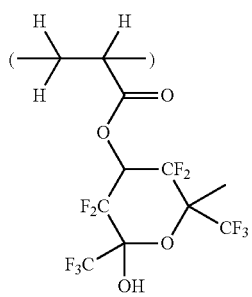 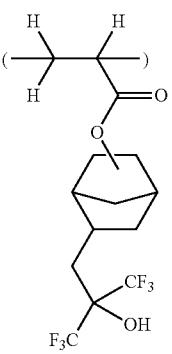

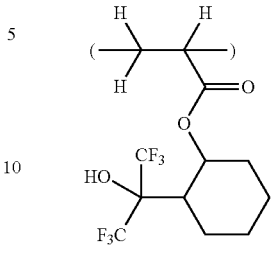 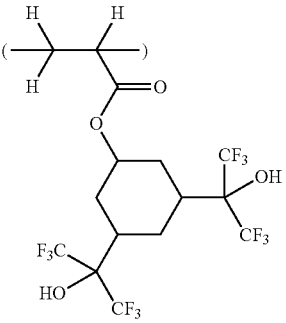

For the surfactant which is insoluble or substantially insoluble in water and soluble in alkaline developer, reference may be made to JP-A 2008-122932, 2010-134012, 2010-107695, 2009-276363, 2009-192784, 2009-191151, 2009-098638, 2010-250105, and 2011-042789.

The polymeric surfactant preferably has a Mw of 1,000 to 50,000, more preferably 2,000 to 20,000 as measured by GPC versus polystyrene standards. A surfactant with a Mw outside the range may be less effective for surface modification and cause development defects. The polymeric surfactant is preferably formulated in an amount of 0.001 to 20 parts, and more preferably 0.01 to 10 parts by weight per 100 parts by weight of the base resin. Reference should also be made to JP-A 2010-215608.

(G) Organic Acid Derivative and/or Fluorinated Alcohol

To the resist composition, a compound which is decomposed with an acid to generate another acid, that is, acid amplifier compound may be added. For these compounds, reference should be made to JP-A 2009-269953 and 2010-215608. In the resist composition, an appropriate amount of the acid amplifier compound is up to 2 parts, and especially up to 1 part by weight per 100 parts by weight of the base resin. Excessive amounts of the acid amplifier compound make diffusion control difficult, leading to degradation of resolution and pattern profile.

Optionally, an organic acid derivative or a compound having a Mw of up to 3,000 which changes its solubility in alkaline developer under the action of an acid, also referred to as dissolution inhibitor, may be added. Reference may be made to JP-A 2009-269953 and 2010-215608.

Process

A further embodiment of the invention is a pattern forming process using the resist composition defined above. A pattern may be formed from the resist composition using any well-known lithography process. The preferred process includes at least the steps of forming a resist film on a substrate, exposing it to high-energy radiation, and developing it in a developer.

First the resist composition is applied onto a substrate for integrated circuitry fabrication (e.g., Si, SiO$_2$, SiN, SiON, TiN, WSi, BPSG, SOG, organic antireflective film, etc.) or a substrate for mask circuitry fabrication (e.g., Cr, CrO, CrON, MoSi, etc.) by a suitable coating technique such as spin coating. The coating is prebaked on a hot plate at a temperature of 60 to 150° C. for 1 to 10 minutes, preferably 80 to 140° C. for 1 to 5 minutes. The resulting resist film is generally 0.05 to 2.0 μm thick. Through a photomask having a desired pattern disposed over the substrate, the resist film is then exposed to high-energy radiation such as KrF excimer laser, ArF excimer laser or EUV in an exposure dose preferably in the range of 1 to 200 mJ/cm$^2$, more preferably 10 to 100 mJ/cm$^2$. Alternatively, pattern formation may be performed by writing with an electron beam directly (not through a mask). Light exposure may be done by a conventional lithography process or in some cases, by an immersion lithography process of providing liquid impregnation, typically water, between the projection lens or mask and the resist film. In the case of immersion lithography, a protective film which is insoluble in water may be used. The resist film is then baked (PEB) on a hot plate at 60 to 150° C. for 1 to 5 minutes, and preferably at 80 to 140° C. for 1 to 3 minutes. Finally, development is carried out using as the developer an aqueous alkaline solution, such as a 0.1 to 5 wt %, preferably 2 to 3 wt %, aqueous solution of tetramethylammonium hydroxide (TMAH), this being done by a conventional method such as dip, puddle, or spray development for a period of 0.1 to 3 minutes, and preferably 0.5 to 2 minutes. In this way the desired pattern is formed on the substrate.

While the water-insoluble protective film which is used in the immersion lithography serves to prevent any components from being leached out of the resist film and to improve water slippage at the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

Any desired step may be added to the pattern forming process. For example, after a photoresist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

The technique enabling the ArF lithography to survive to the 32-nm node is a double patterning process. The double patterning process includes a trench process of processing an underlay to a 1:3 trench pattern by a first step of exposure and etching, shifting the position, and forming a 1:3 trench pattern by a second step of exposure for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

In the pattern forming process, an alkaline aqueous solution, typically an aqueous solution of 0.1 to 5 wt %, more typically 2 to 3 wt % of tetramethylammonium hydroxide (TMAH) is often used as the developer. The negative tone development technique wherein the unexposed region is developed and dissolved in an organic solvent is also applicable.

In the organic solvent development, the organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, isoamyl acetate, butenyl acetate, phenyl acetate, propyl formate, butyl formate, isobutyl formate, amyl formate, isoamyl formate, methyl valerate, methyl pentenoate, methyl crotonate, ethyl crotonate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

EXAMPLE

Examples and Comparative Examples are given below by way of illustration and not by way of limitation. All parts are by weight (pbw).

Synthesis Example 1

Synthesis of Photoacid Generator

Photoacid generators within the scope of the invention were synthesized according to the following formulation.

Synthesis Example 1-1

Synthesis of PAG-1

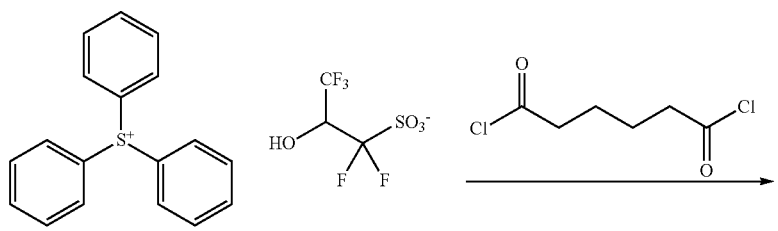

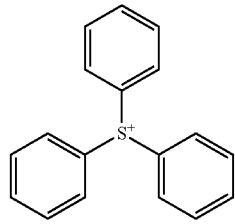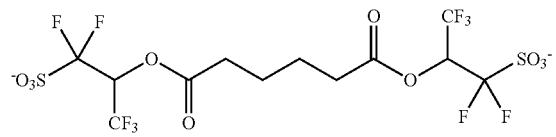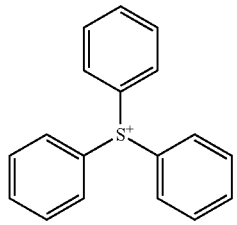

PAG-1

Under ice cooling, 0.8 g of adipic acid chloride was added dropwise to a mixture of 4.9 g of triphenylsulfonium 1,1,3,3,3-pentafluoro-2-hydroxypropane-1-sulfonate, synthesized according to the method of JP-A 2007-145804, 1.0 g of triethylamine, 0.2 g of N,N'-dimethyl-4-aminopyridine, and 20 g of methylene chloride. The contents were stirred at room temperature for 1 hour, after which dilute hydrochloric acid was added to quench the reaction. The organic layer was taken out, washed with water, and concentrated under reduced pressure by distilling off methylene chloride. Methyl isobutyl ketone was added to the concentrate, which was concentrated under reduced pressure again. Diethyl ether was added to the concentrate, from which the supernatant was removed, obtaining 3.8 g of the target compound (yield 77%).

Figure 2:
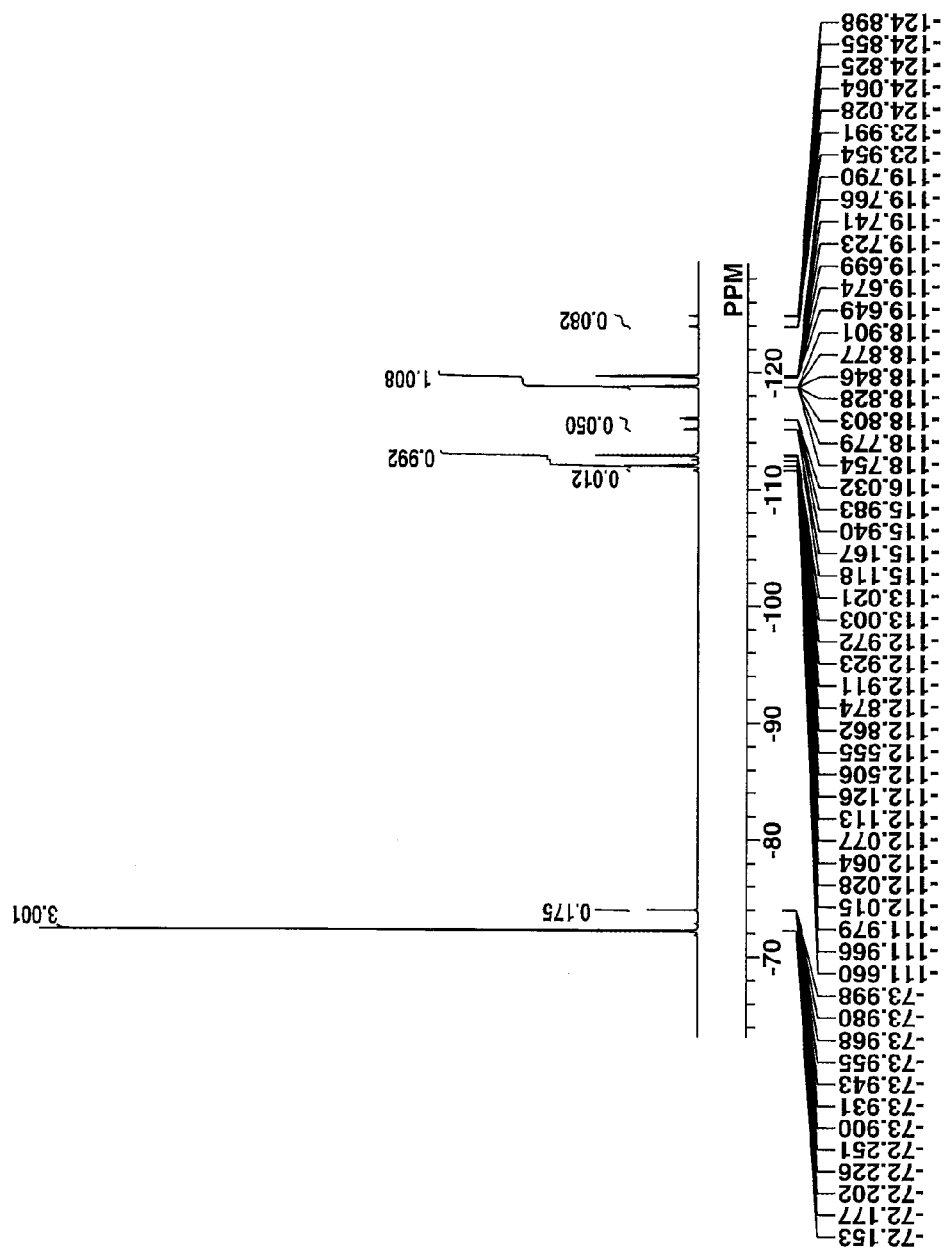
FIG. 2 is a diagram showing the $^{19}$F-NMR/DMSO-$d_6$ spectrum of PAG-1 in Synthesis Example 1-1.

The target compound was analyzed by spectroscopy. The data of time-of-flight mass spectrometry (TOFMS) are shown below. The NMR spectra, $^1$H-NMR and $^{19}$F-NMR in DMSO-$d_6$ are shown in FIGS. 1 and 2. On $^1$H-NMR analysis, minor amounts of residual solvents (diethyl ether, methyl isobutyl ketone, water) and the reactant, triphenylsulfonium 1,1,3,3,3-pentafluoro-2-hydroxypropane-1-sulfonate were observed.

TOFMS (MALDI)

Positive M$^+$263 (corresponding to $(C_6H_5)_3S^+$)

Negative M$^-$589 (corresponding to HO$_3$S—CF$_2$CH(CF$_3$)—(OCOC$_6$H$_4$—COO)—CH(CF$_3$)—CF$_2$—SO$_3^-$)

Synthesis Example 1-2

Synthesis of PAG-2

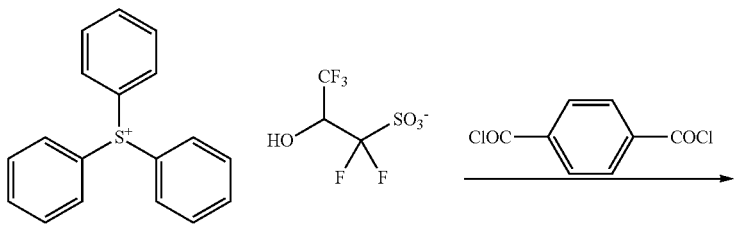

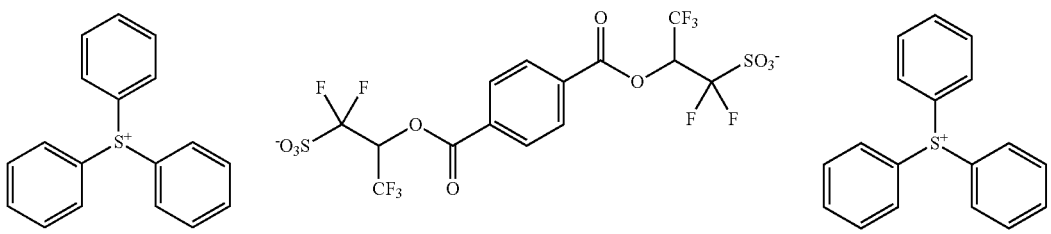

PAG-2

Under ice cooling, a mixture of 0.9 g of terephthalic acid chloride and 5 g of methylene chloride was added dropwise to a mixture of 4.9 g of triphenylsulfonium 1,1,3,3,3-pentafluoro-2-hydroxypropane-1-sulfonate, synthesized according to the method of JP-A 2007-145804, 1.0 g of triethylamine, 0.2 g of N,N'-dimethyl-4-aminopyridine, and 20 g of methylene chloride. The contents were stirred at room temperature for 1 hour, after which dilute hydrochloric acid was added to quench the reaction. The organic layer was taken out, washed with water, and concentrated under reduced pressure by distilling off methylene chloride. Methyl isobutyl ketone was added to the concentrate, which was concentrated under reduced pressure again. Diethyl ether was added to the concentrate, from which the supernatant was removed, obtaining 4.4 g of the target compound (yield 87%).

Figure 3:
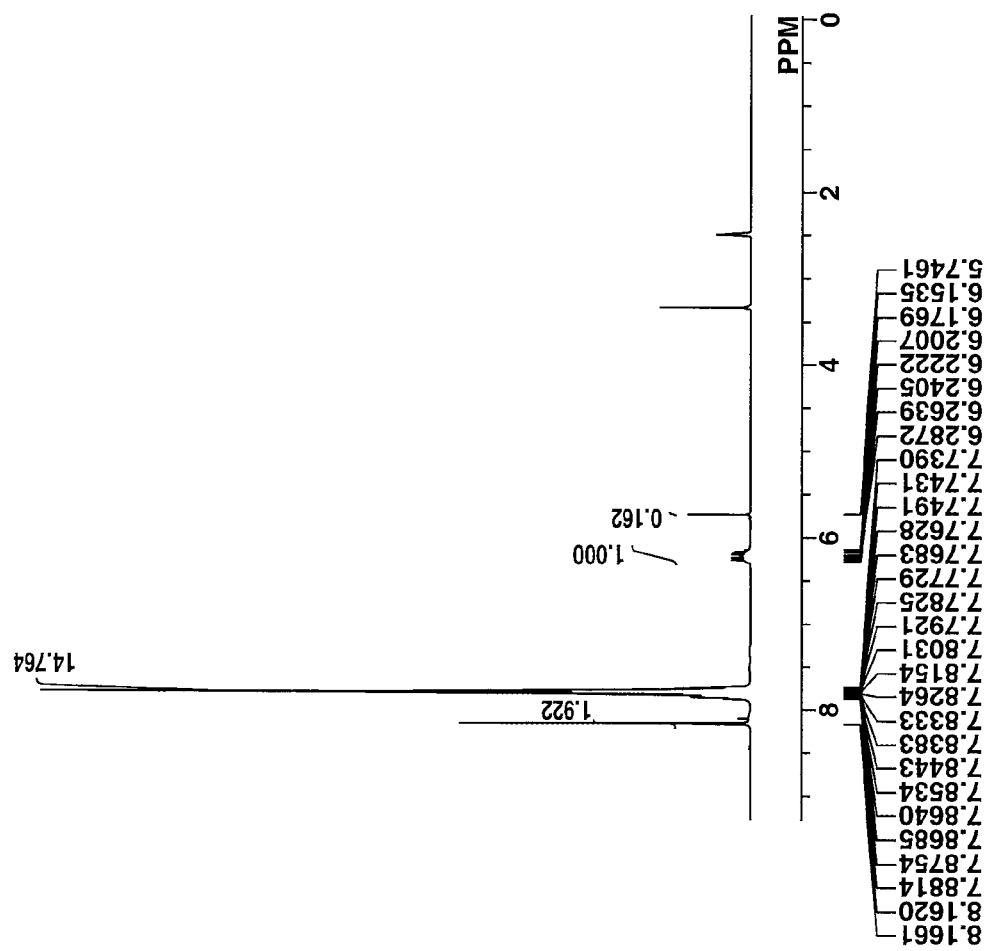
FIGS. 3 and 4 are diagrams showing the $^1$H-NMR/DMSO-$d_6$ and $^{19}$F-NMR/DMSO-$d_6$ spectra of PAG-2 in Synthesis Example 1-2, respectively.
Figure 4:
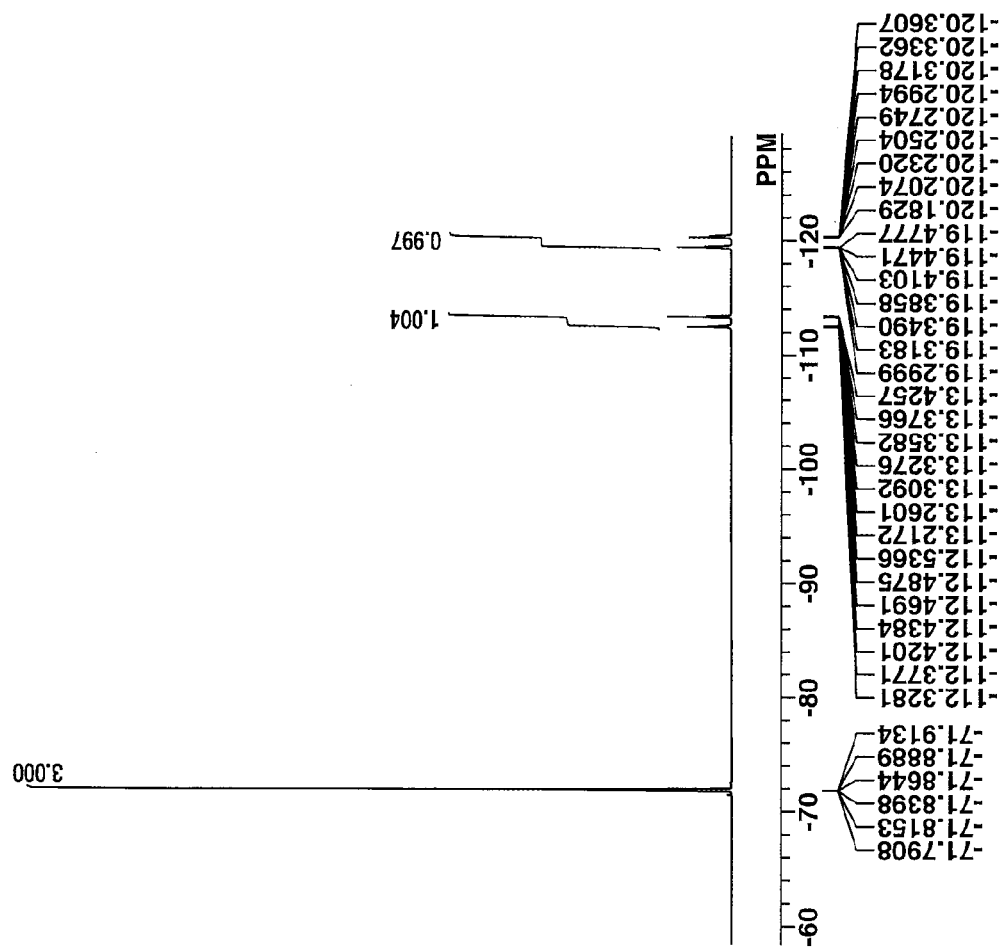

The target compound was analyzed by spectroscopy. The data of infrared (IR) absorption spectroscopy and time-of-flight mass spectrometry (TOFMS) are shown below. The NMR spectra, $^1$H-NMR and $^{19}$F-NMR in DMSO-$d_6$ are shown in FIGS. 3 and 4. On $^1$H-NMR analysis, minor amounts of residual solvents (methylene chloride, water) were observed.

IR Spectra (KBr, cm$^{-1}$)

3424, 1751, 1477, 1448, 1330, 1253, 1216, 1186, 1164, 1103, 1072, 995, 904, 748, 725, 684, 640, 576, 551, 503 cm$^{-1}$

TOFMS (MALDI)

Positive M$^+$263 (corresponding to $(C_6H_5)_3S^+$)

Negative M$^-$569 (corresponding to HO$_3$S—CF$_2$CH(CF$_3$)—(OCOC$_4$H$_8$—COO)—CH(CF$_3$)—CF$_2$—SO$_3^-$)

Synthesis Example 1-3

Synthesis of PAG-3 of triethylamine, 0.5 g of N,N'-dimethyl-4-aminopyridine, and 40 g of methylene chloride. The contents were stirred at room temperature for 1 hour, after which dilute hydrochloric acid was added to quench the reaction. The organic layer was taken out, washed with water, and concentrated under reduced pressure by distilling off methylene chloride. Methyl isobutyl ketone was added to the concentrate, which was concentrated under reduced pressure again. Diethyl ether was added to the concentrate, from which the supernatant was removed, obtaining 4.8 g of the target compound (yield 41%).

Figure 5:
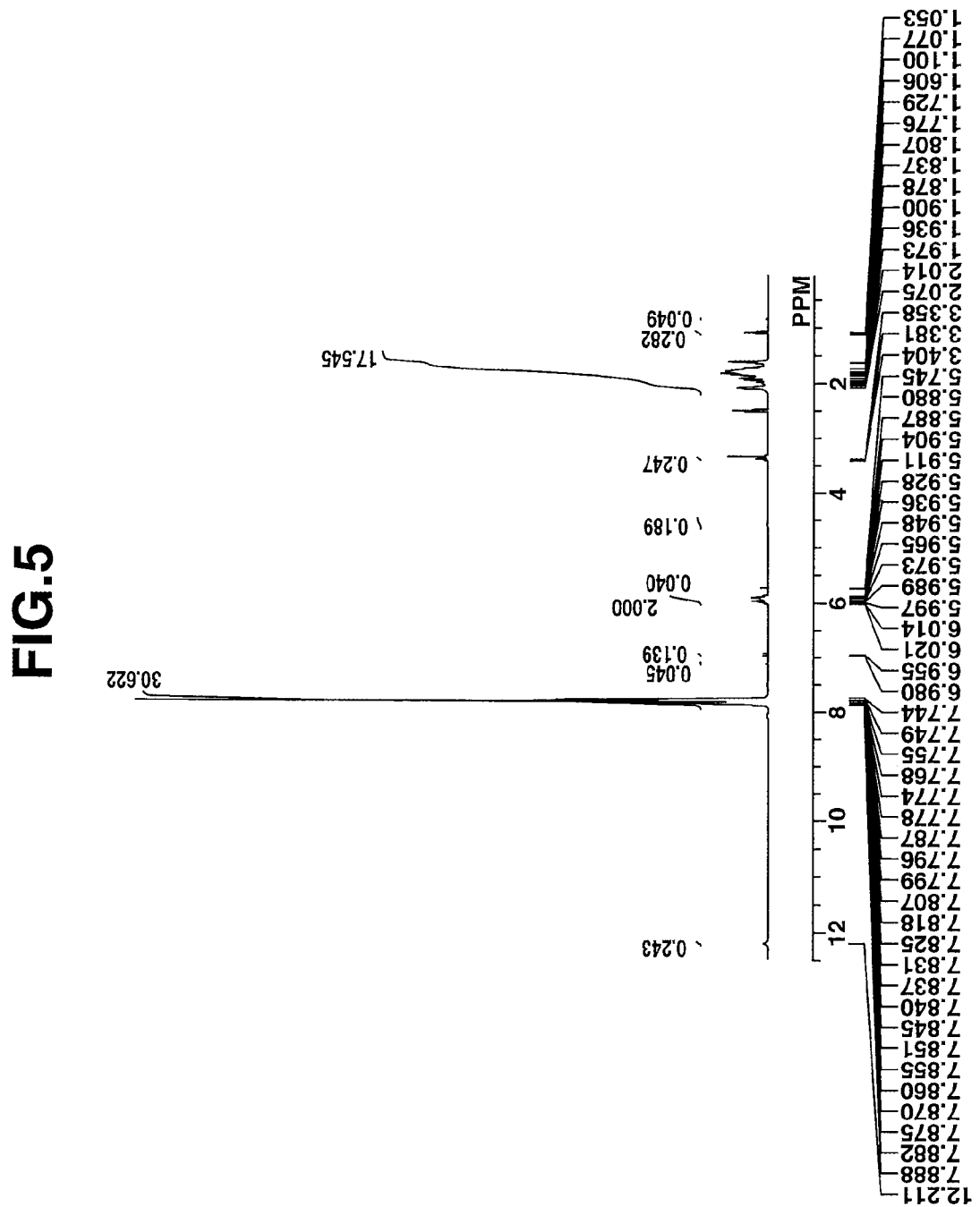
FIGS. 5 and 6 are diagrams showing the $^1$H-NMR/DMSO-$d_6$ and $^{19}$F-NMR/DMSO-$d_6$ spectra of PAG-3 in Synthesis Example 1-3, respectively.
Figure 6:
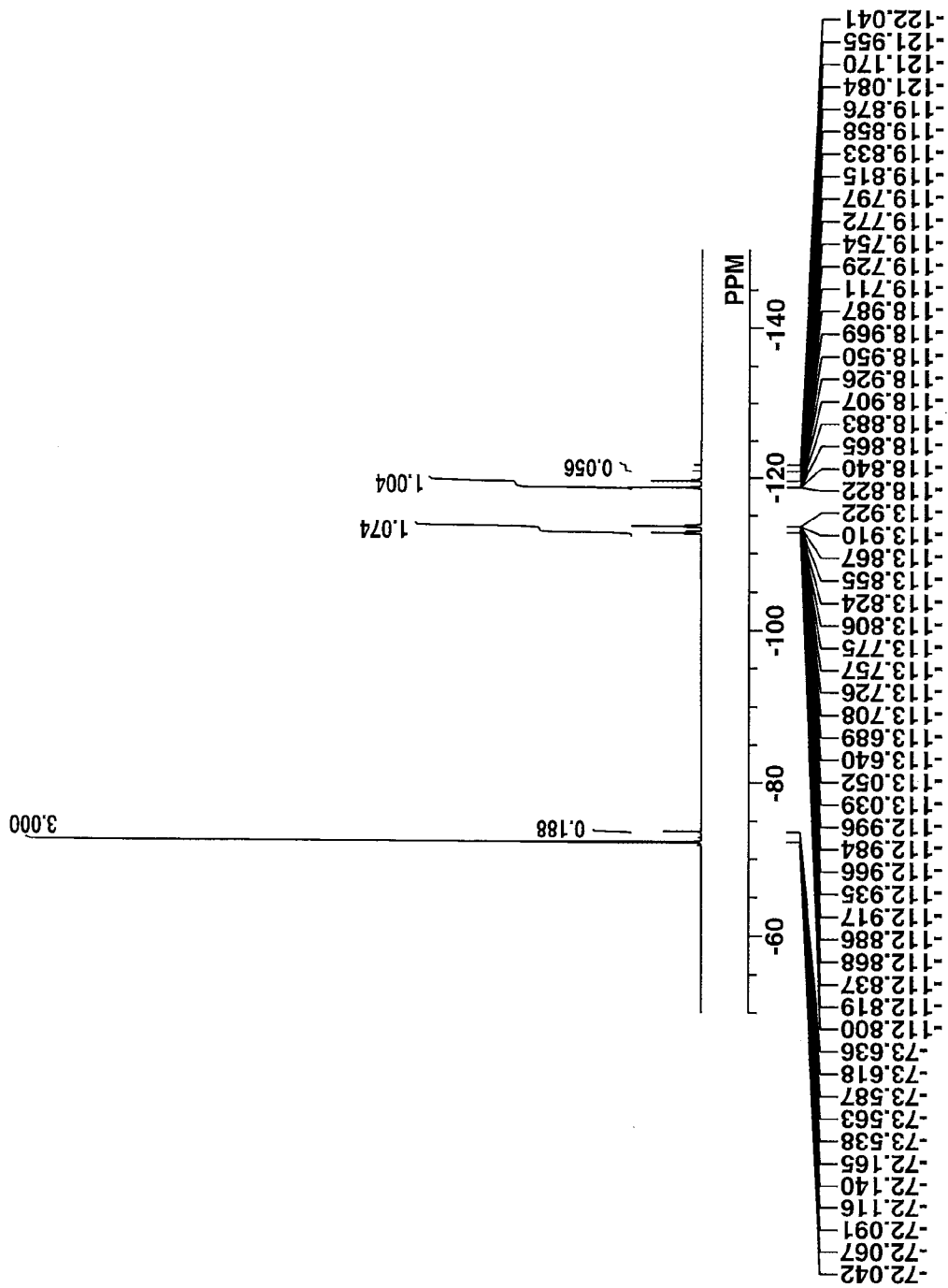

The target compound was analyzed by spectroscopy. The data of TOFMS are shown below. The NMR spectra, $^1$H-NMR and $^{19}$F-NMR in DMSO-$d_6$ are shown in FIGS. 5 and 6. On $^1$H-NMR analysis, minor amounts of residual solvents (diethyl ether, water), adamantanedicarboxylic acid and the reactant, triphenylsulfonium 1,1,3,3,3-pentafluoro-2-hydroxypropane-1-sulfonate were observed.

TOFMS (MALDI)

Positive M$^+$263 (corresponding to $(C_6H_5)_3S^+$)

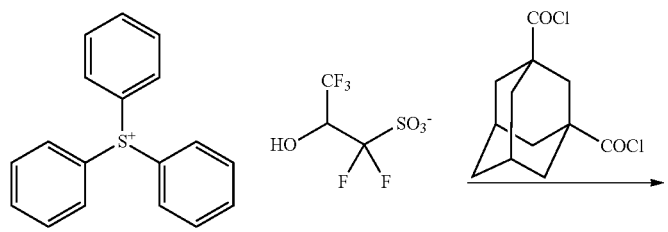

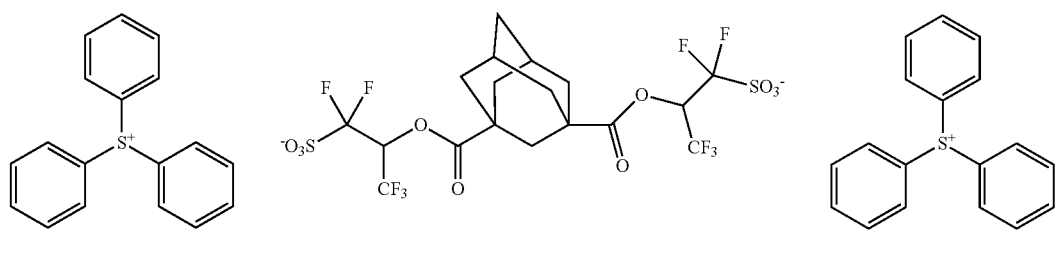

PAG-3

Under ice cooling, a mixture of 2.4 g of 1,3-adamantanedicarboxylic acid chloride and 5 g of methylene chloride was added dropwise to a mixture of 9.8 g of triphenylsulfonium 1,1,3,3,3-pentafluoro-2-hydroxypropane-1-sulfonate, synthesized according to the method of JP-A 2007-145804, 2.0 g Negative M$^-$647 (corresponding to HO$_3$S—CF$_2$CH(CF$_3$)—(OCOC$_{10}$H$_{14}$—COO)—CH(CF$_3$)—CF$_2$—SO$_3^-$)

Synthesis Example 1-4

Synthesis of PAG Intermediate 1

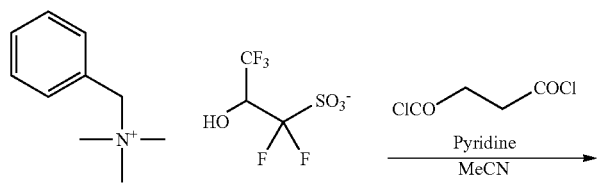

-continued

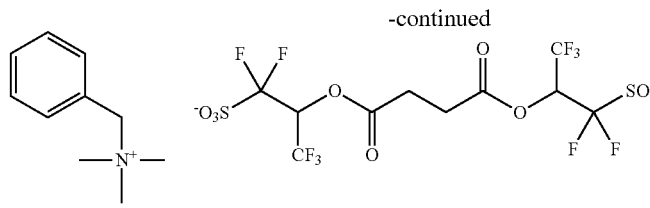

A 3-L four-necked flask was charged with 341 g of benzyltrimethylammonium 1,1,3,3,3-pentafluoro-2-hydroxypropane-1-sulfonate, synthesized according to the method of JP-A 2012-107151, 62 g of succinyl chloride, and 1,000 g of acetonitrile. Under ice cooling, 95 g of pyridine was added dropwise to the mixture. At the end of dropwise addition, the reaction solution was warmed and aged at room temperature for 18 hours. Dilute hydrochloric acid was added to quench the reaction. The reaction solution was concentrated on an evaporator, with acetonitrile being distilled off. Methylene chloride, 1,000 g, was added to the residue. Using 500 g of 2 wt % benzyltrimethylammonium chloride aqueous solution, separatory operation was carried out 4 times to adjust a cation to anion ratio. This was followed by water washing. The methylene chloride solution was concentrated, from which water was azeotroped off using 300 g of methyl isobutyl ketone. The residue was crystallized from 1,000 g of diisopropyl ether. The crystals were filtered and dried, obtaining 258 g of the target compound as gray crystals (yield 77%).

Synthesis Example 1-5

Synthesis of PAG-4

A mixture of 84 g of PAG intermediate 1 obtained in Synthesis Example 1-4, 90 g of triphenylsulfonium methylsulfate synthesized according to the well-known formulation, 400 g of methylene chloride, and 200 g of water was stirred at room temperature for 18 hours. This was followed by water washing, separatory operation, and concentration of the methylene chloride solution. 100 g of methyl isobutyl ketone was added to the concentrate, from which water was azeotroped off. Diisopropyl ether was added to the residue, from which the supernatant was removed. The residue was concentrated under reduced pressure, obtaining 117 g of the target compound (yield 98%).

Figure 7:
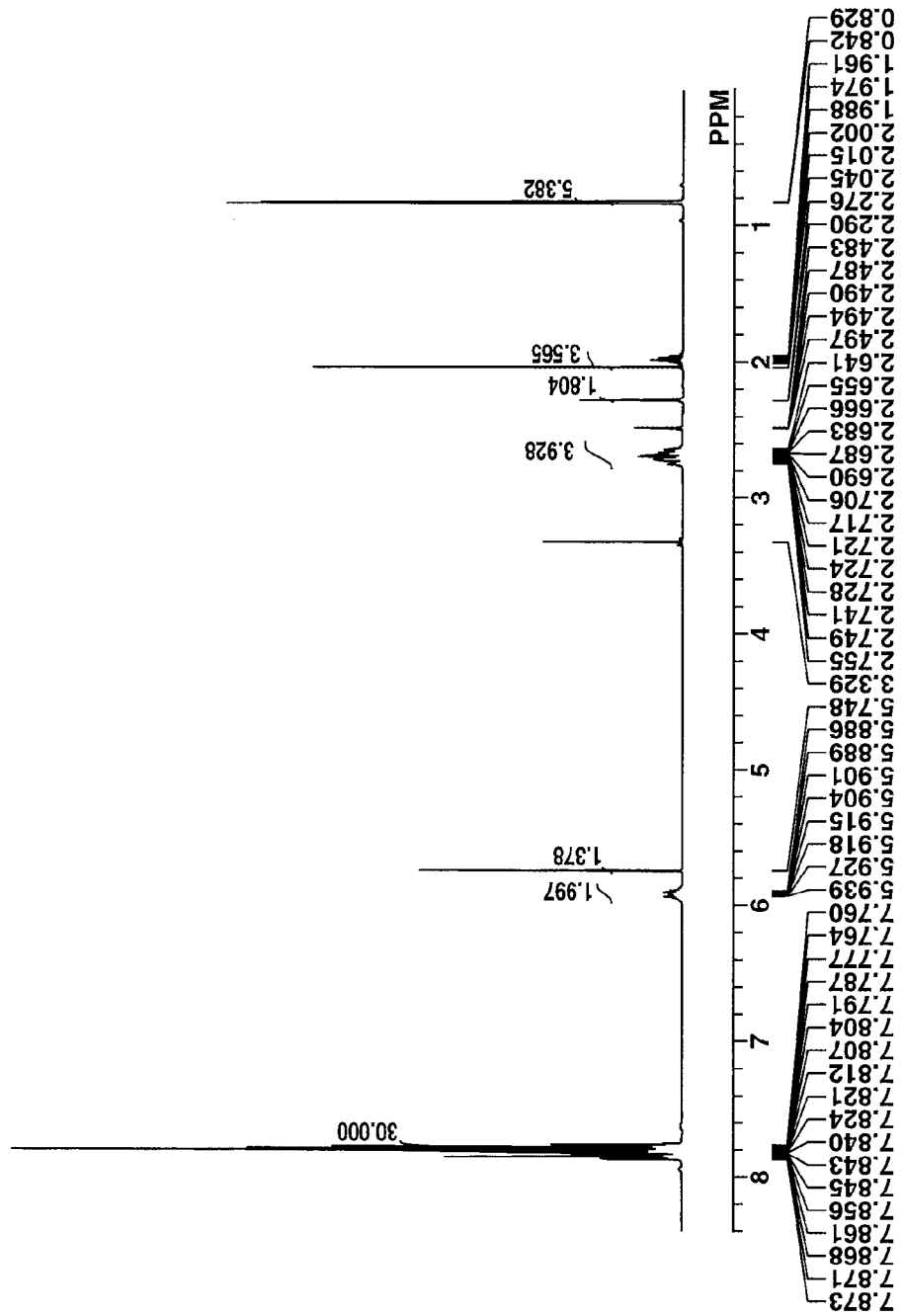
FIGS. 7 and 8 are diagrams showing the $^1$H-NMR/DMSO-$d_6$ and $^{19}$F-NMR/DMSO-$d_6$ spectra of PAG-4 in Synthesis Example 1-5, respectively.
Figure 8:
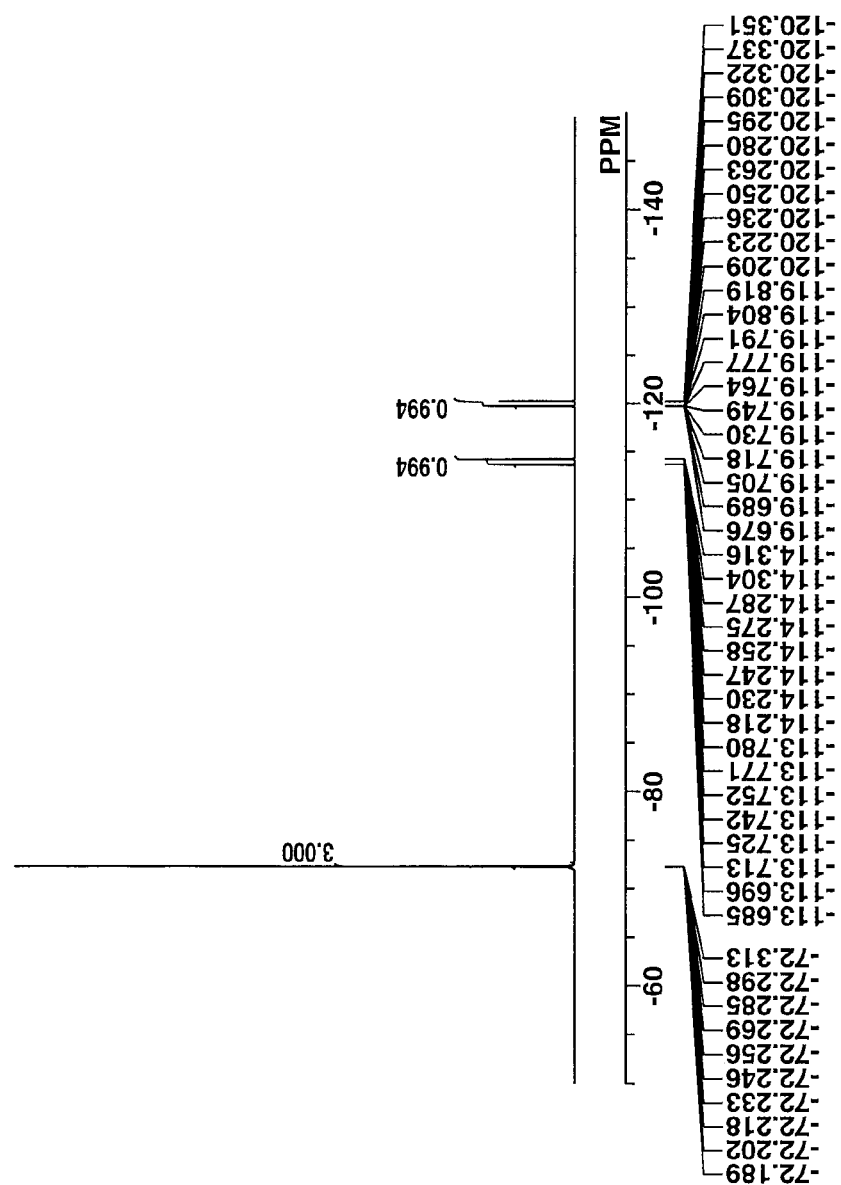

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 7 and 8. On $^1$H-NMR analysis, minor amounts of residual solvents (diisopropyl ether, methyl isobutyl ketone, water) were observed.

IR Spectra (D-ATR, cm$^{-1}$)
    3494, 3090, 3064, 2972, 1770, 1477, 1448, 1371, 1251, 1218, 1186, 1171, 1126, 1073, 995, 905, 841, 750, 645, 642, 575 cm$^{-1}$

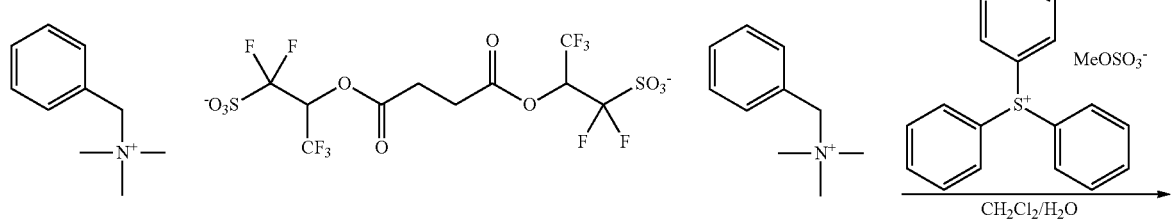

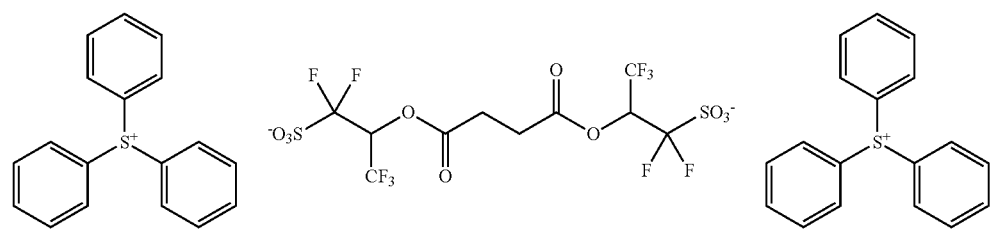

PAG-4

TOFMS (MALDI)
  Positive M$^+$263 (corresponding to (C$_6$H$_5$)$_3$S$^+$)
  Negative M$^-$541 (corresponding to HO$_3$S—CF$_2$CH(CF$_3$)—(OCOC$_2$H$_4$—COO)—CH(CF$_3$)—CF$_2$—SO$_3$$^-$)

Synthesis Example 1-6

Synthesis of PAG-5

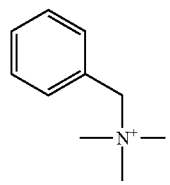 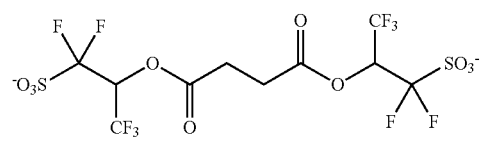 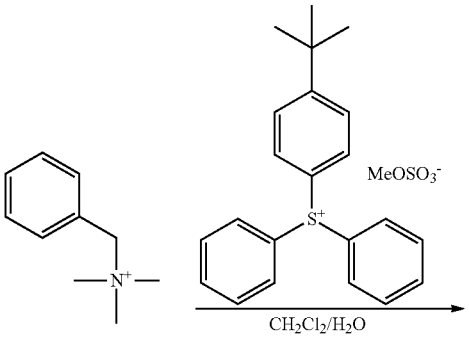

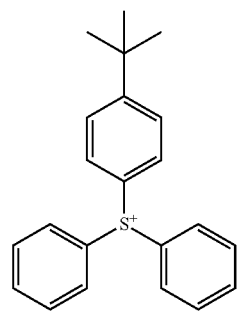 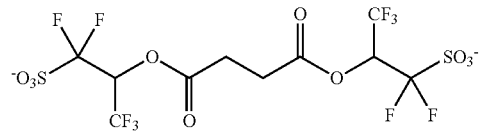 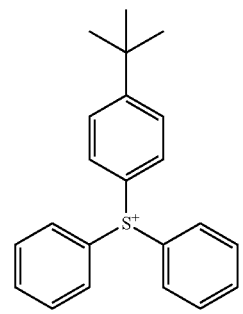

PAG-5

A mixture of 6 g of PAG intermediate 1 obtained in Synthesis Example 1-4, 85 g of an aqueous solution of 4-tert-butylphenyldiphenylsulfonium methylsulfate synthesized according to the well-known formulation, and 100 g of methylene chloride was stirred at room temperature for 15 hours. This was followed by water washing, separatory operation, and concentration of the methylene chloride solution. 50 g of methyl isobutyl ketone was added to the concentrate, from which water was azeotroped off. Diisopropyl ether was added to the residue, from which the supernatant was removed. The residue was concentrated under reduced pressure, obtaining 8.2 g of the target compound, PAG-5 (yield 96%).

Figure 9:
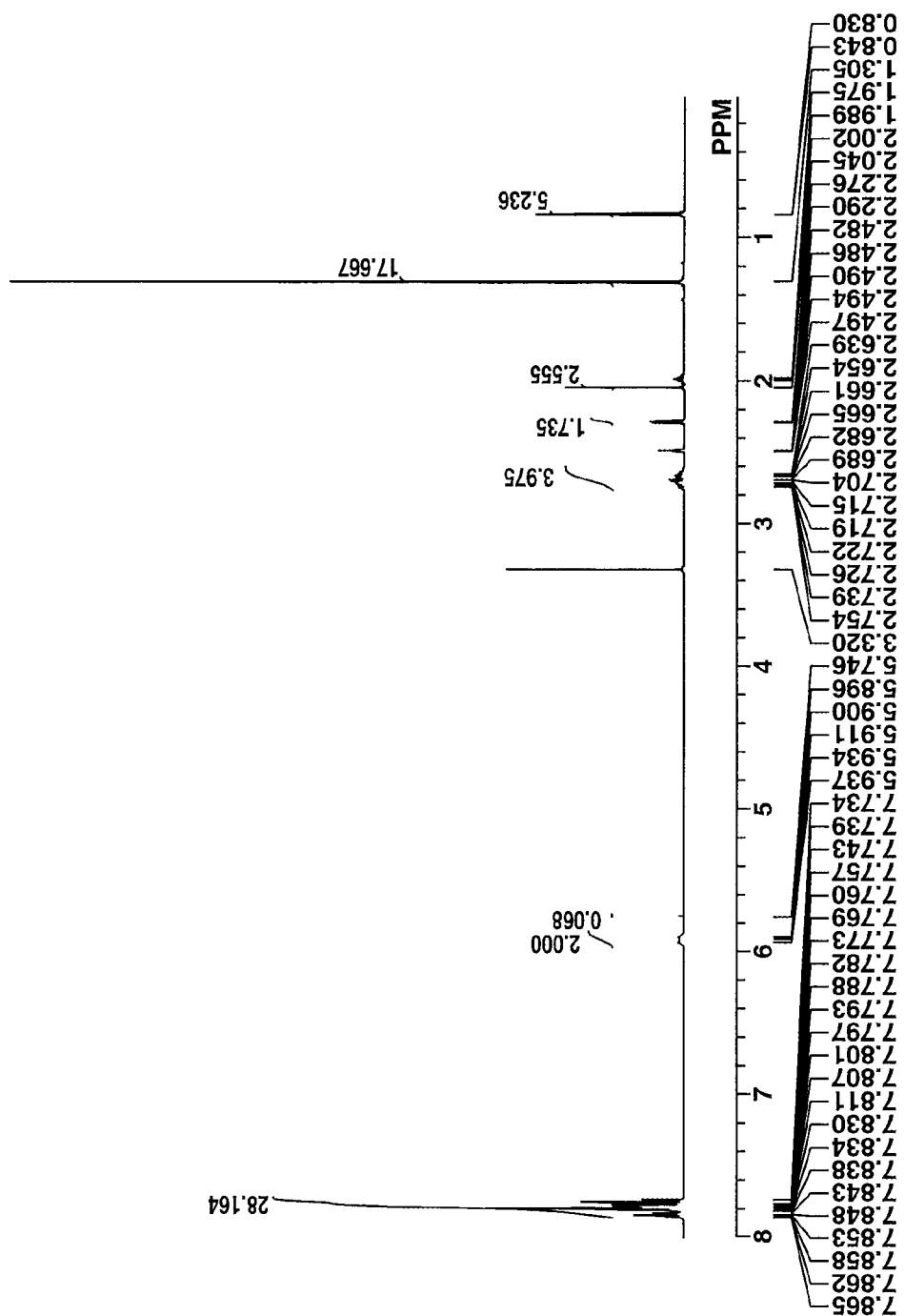
FIGS. 9 and 10 are diagrams showing the $^1$H-NMR/DMSO-$d_6$ and $^{19}$F-NMR/DMSO-$d_6$ spectra of PAG-5 in Synthesis Example 1-6, respectively.
Figure 10:
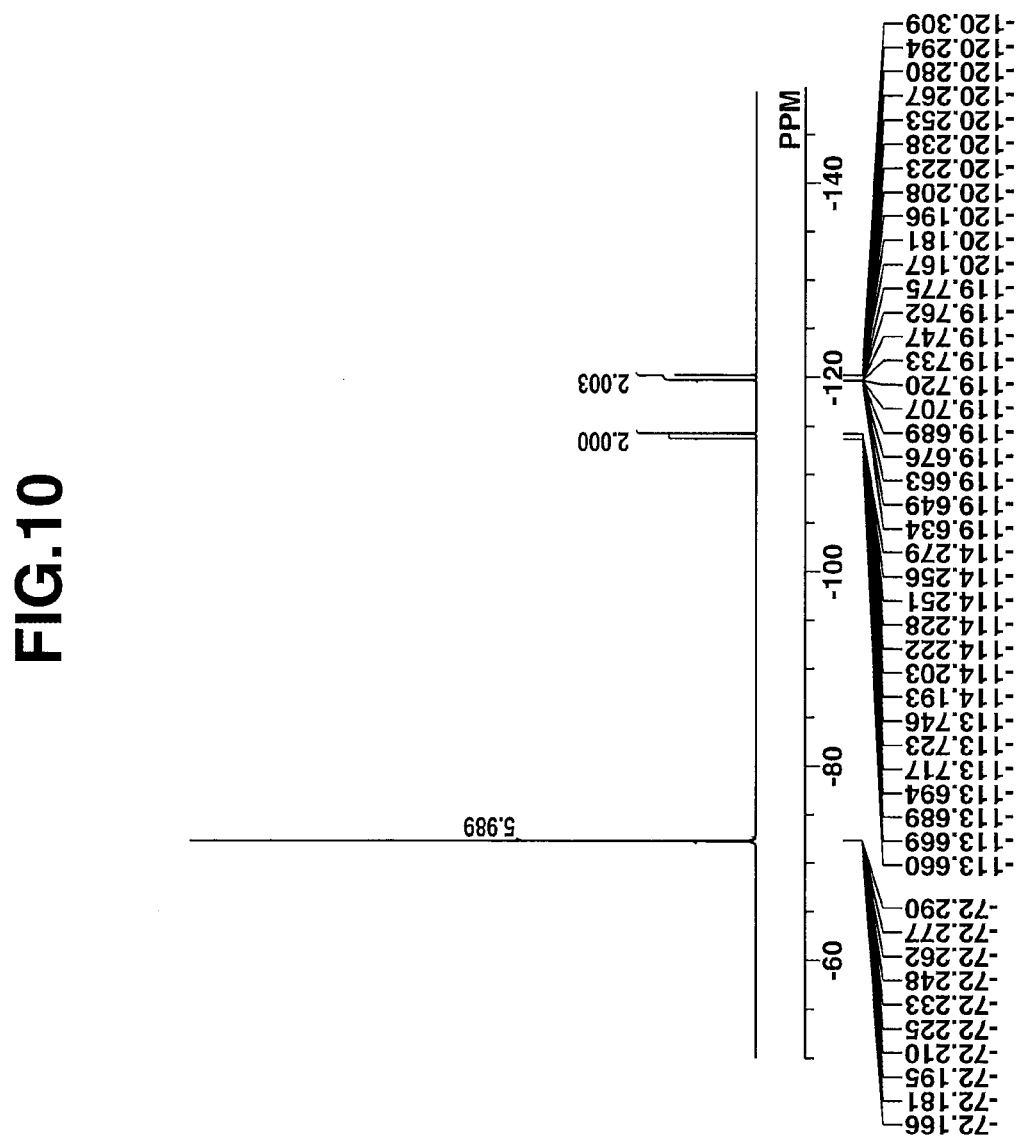

The target compound was analyzed by spectroscopy. The data of IR spectroscopy and TOFMS are shown below. The NMR spectra, $^1$H-NMR and $^{19}$F-NMR in DMSO-d$_6$ are shown in FIGS. 9 and 10. On $^1$H-NMR analysis, minor amounts of residual solvents (diisopropyl ether, methyl isobutyl ketone, water) were observed.

IR Spectra (D-ATR, cm$^{-1}$)
  3501, 3064, 2966, 2873, 1770, 1709, 1478, 1447, 1403, 1369, 1251, 1217, 1185, 1171, 1073, 995, 839, 752, 685, 643, 554 cm$^{-1}$ TOFMS (MALDI)
  Positive M$^+$319 (corresponding to (C$_6$H$_5$)$_2$(C$_4$H$_9$—C$_6$H$_4$)S$^+$)
  Negative M$^-$541 (corresponding to HO$_3$S—CF$_2$CH(CF$_3$)—(OCOC$_2$H$_4$—COO)—CH(CF$_3$)—CF$_2$—SO$_3$$^-$)

Synthesis Example 1-7

Synthesis of PAG-6

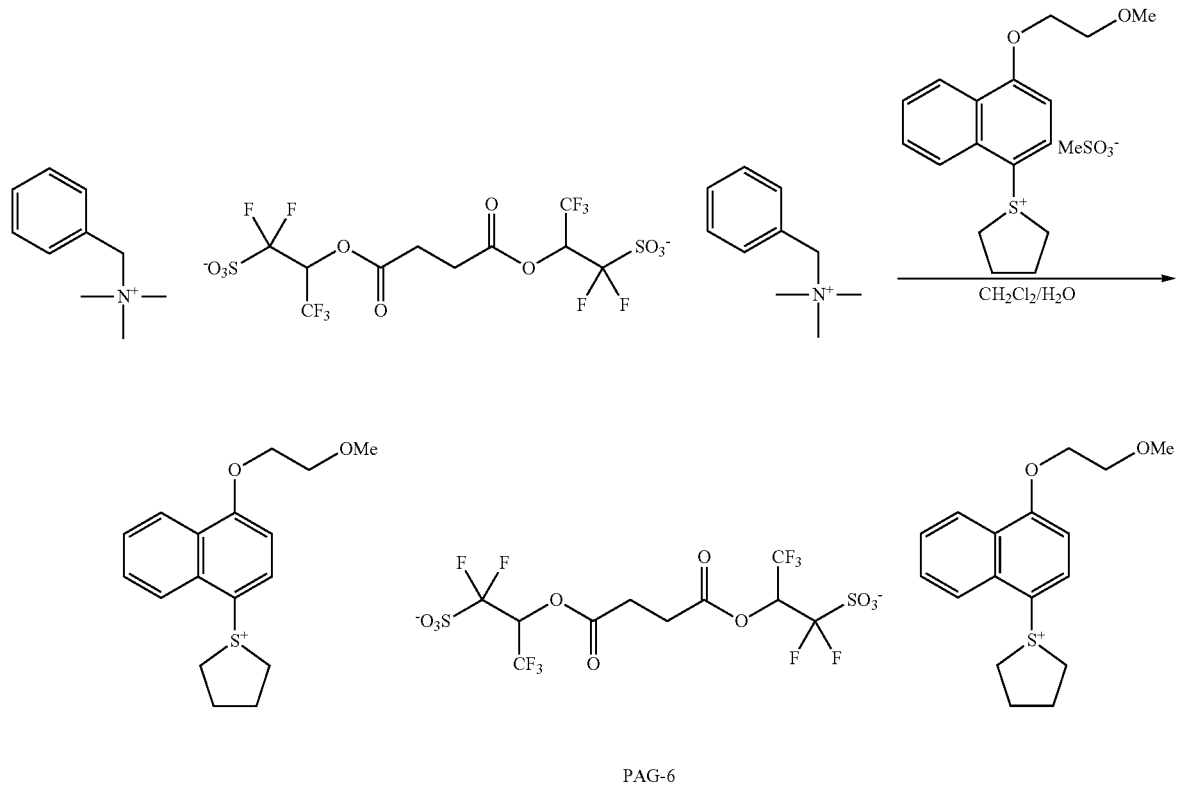

PAG-6

A mixture of 8.4 g of PAG intermediate 1 obtained in Synthesis Example 1-4, 110 g of an aqueous solution of 4-(2-methoxyethoxyl)naphthalene-1-tetrahydrothiophenium methanesulfonate synthesized according to the formulation of JP-A 2012-041320, and 100 g of methylene chloride was stirred at room temperature for 15 hours. This was followed by water washing, separatory operation, and concentration of the methylene chloride solution. 50 g of methyl isobutyl ketone was added to the concentrate, from which water was azeotroped off. Diisopropyl ether was added to the residue, from which the supernatant was removed. The residue was concentrated under reduced pressure, obtaining 9.6 g of the target compound, PAG-6 (yield 86%).

Figure 11:
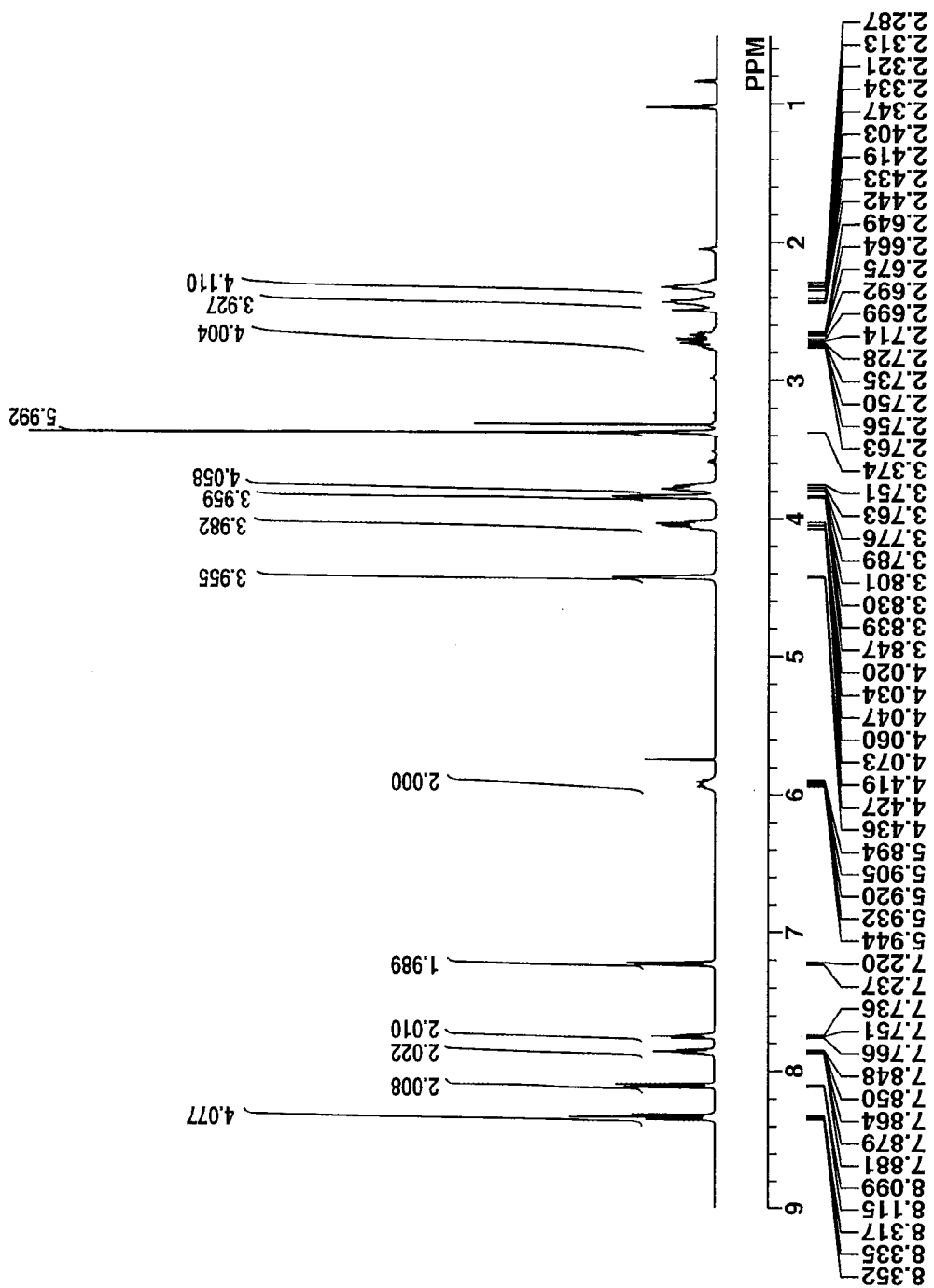
FIGS. 11 and 12 are diagrams showing the $^1$H-NMR/DMSO-$d_6$ and $^{19}$F-NMR/DMSO-$d_6$ spectra of PAG-6 in Synthesis Example 1-7, respectively.
Figure 12:
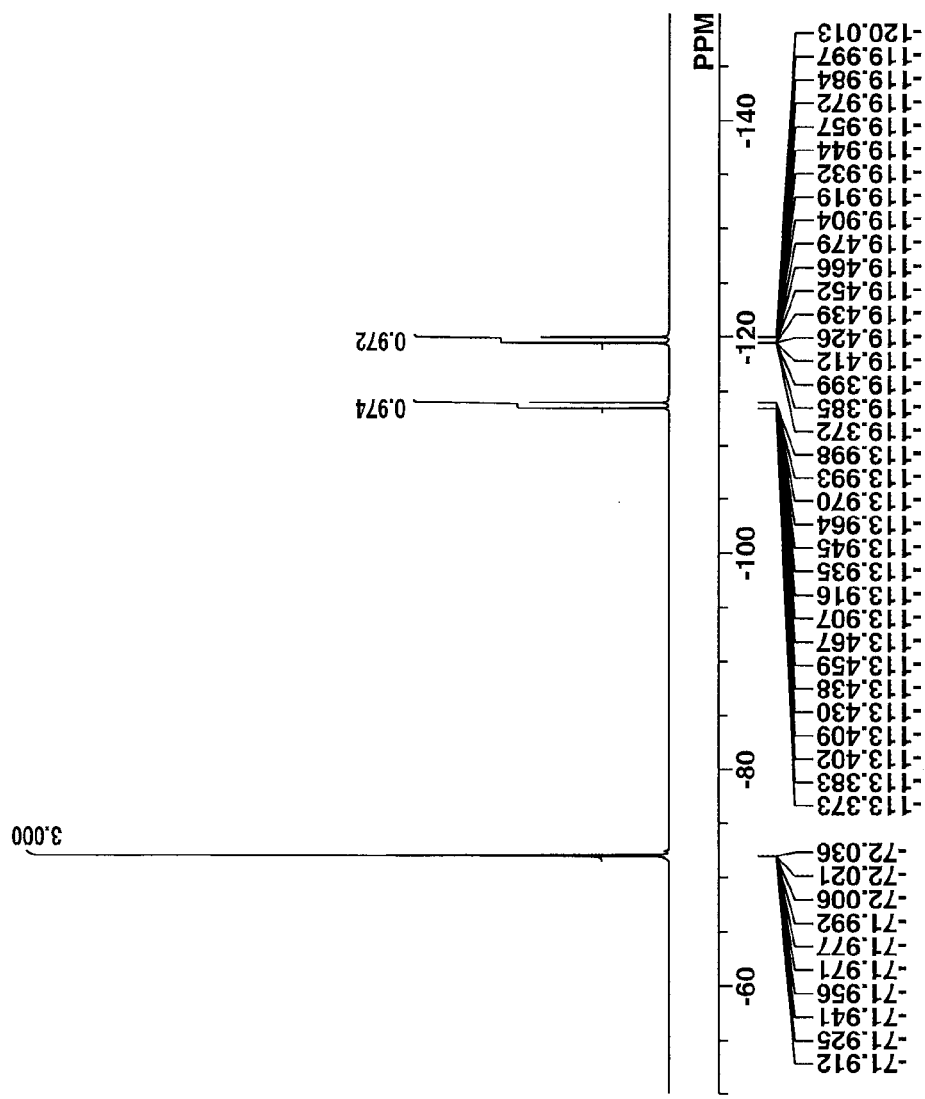

The target compound was analyzed by spectroscopy. The data of IR spectroscopy and TOFMS are shown below. The NMR spectra, $^1$H-NMR and $^{19}$F-NMR in DMSO-$d_6$ are shown in FIGS. 11 and 12. On $^1$H-NMR analysis, minor amounts of residual solvents (diisopropyl ether, methyl isobutyl ketone, water) were observed.

IR Spectra (D-ATR, cm$^{-1}$)
  2969, 1770, 1588, 1571, 1509, 1463, 1428, 1372, 1323, 1248, 1216, 1186, 1170, 1127, 1088, 1033, 992, 764, 643 cm$^{-1}$ TOFMS (MALDI)
  Positive M$^+$289 (corresponding to $(C_{17}H_{21}O_2)S^+$
  Negative M$^-$541 (corresponding to $HO_3S-CF_2CH(CF_3)-(OCOC_2H_4-COO)-CH(CF_3)-CF_2-SO_3$)

Synthesis Example 2

Synthesis of Polymers

Polymers for use in resist compositions were synthesized according to the following formulation. Mw is weight average molecular weight as measured versus polystyrene standards by GPC using tetrahydrofuran solvent, and Mw/Mn is dispersity.

Synthesis Example 2-1

Synthesis of Polymer P-1

In nitrogen atmosphere, 22 g of 1-tert-butylcyclopentyl methacrylate, 17 g of 2-oxotetrahydrofuran-3-yl methacrylate, 0.41 g of dimethyl 2,2'-azobis(2-methylpropionate) (V-601 by Wako Pure Chemical Industries, Ltd.), 0.41 g of 2-mercaptoethanol, and 50 g of methyl ethyl ketone were combined to form a monomer/initiator solution. A flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The precipitate was collected by filtration, washed twice with 240 g of methanol, and vacuum dried at 50° C. for 20 hours, obtaining 36 g of a copolymer in white powder form (yield 90%). On GPC analysis, the copolymer had a Mw of 8,755 and a Mw/Mn of 1.94.

P-1

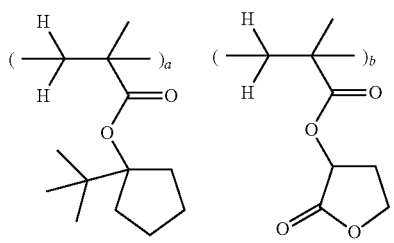

(a = 0.50, b = 0.50)

Synthesis Examples 2-2 to 2-12

Synthesis of Polymers P-2 to P-12

Polymers were synthesized by the same procedure as in Synthesis Example 2-1 aside from changing the type and amount of monomers.

Table 1 shows the proportion (in molar ratio) of units incorporated in these polymers, and Tables 2 and 3 show the structure of recurring units.

TABLE 1

| Polymer | Unit 1 (molar ratio) | Unit 2 (molar ratio) | Unit 3 (molar ratio) | Unit 4 (molar ratio) |
|---|---|---|---|---|
| P-1 | A-1 (0.50) | B-1 (0.50) | — | — |
| P-2 | A-1 (0.40) | B-1 (0.50) | B-3 (0.10) | — |
| P-3 | A-1 (0.50) | B-2 (0.20) | B-3 (0.20) | B-5 (0.10) |
| P-4 | A-2 (0.40) | B-1 (0.60) | — | — |
| P-5 | A-2 (0.40) | B-2 (0.60) | — | — |
| P-6 | A-2 (0.20) | A-3 (0.30) | B-1 (0.40) | B-5 (0.10) |
| P-7 | A-2 (0.20) | A-3 (0.30) | B-2 (0.40) | B-5 (0.10) |
| P-8 | A-1 (0.25) | A-2 (0.25) | B-3 (0.40) | B-5 (0.10) |
| P-9 | A-1 (0.20) | A-2 (0.25) | B-1 (0.35) | B-3 (0.20) |
| P-10 | A-3 (0.25) | A-5 (0.25) | B-1 (0.35) | B-5 (0.15) |
| P-11 | A-4 (0.50) | B-4 (0.50) | — | — |
| P-12 | A-6 (0.35) | B-3 (0.65) | — | — |

TABLE 2

A-1

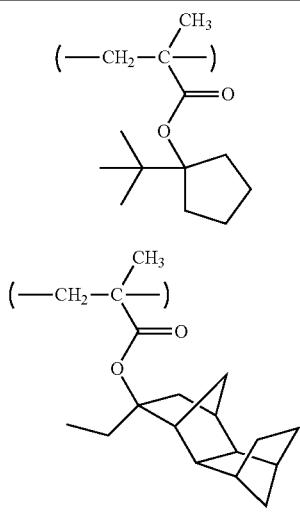

A-2

TABLE 2-continued

A-3

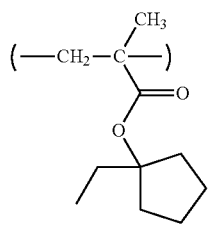

A-4

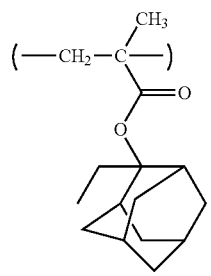

A-5

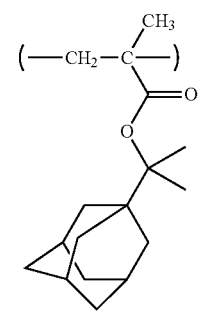

A-6

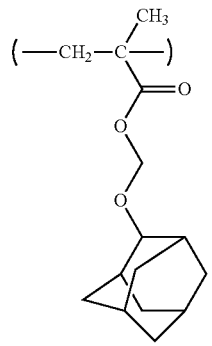

TABLE 3

B-1

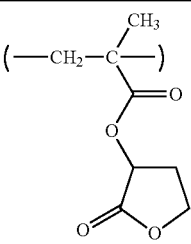

TABLE 3-continued

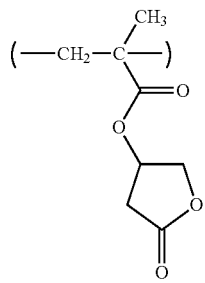 B-2

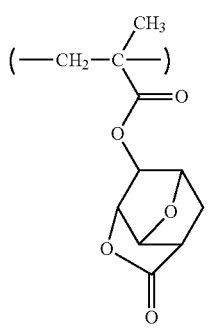 B-3

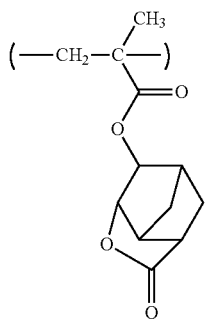 B-4

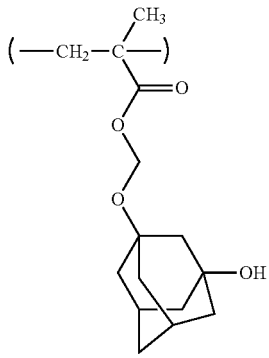 B-5

Examples 1-1 to 1-20 and Comparative Examples 1-1 to 1-7

Preparation of Resist Composition

A resist composition in solution form was prepared by dissolving each sulfonium salt (synthesized above), each polymer (Polymers P-1 to P-12 synthesized above), another sulfonium salt (PAG-X, Y, Z), quencher (Q-1), and alkali-soluble surfactant (F-1) in an organic solvent containing 0.01 wt % of surfactant A, and filtering through a Teflon® filter with a pore size of 0.2 μm. Table 4 shows the formulation of the resulting resist solution.

The quencher (Q-1), solvent, alkali-soluble surfactant (F-1), other sulfonium salt (PAG-X, Y, Z), and surfactant A used herein are identified below.

Q-1: 2-(4-morpholinyl)ethyl octadecanoate

PGMEA: propylene glycol monomethyl ether acetate

GBL: γ-butyrolactone

PAG-X: triphenylsulfonium 2-(adamantane-1-carbonyloxy)-1,1,3,3,3-pentafluoropropane-1-sulfonate (described in JP-A 2007-145797)

PAG-Y: triphenylsulfonium 2-(adamantane-1-carbonyloxy)-3,3,3-trifluoro-2-trifluoromethylpropane-1-sulfonate (described in JP-A 2010-215608)

PAG-Z: triphenylsulfonium 2-(adamantane-1-carbonyloxy)-ethanesulfonate (described in JP-A 2010-155824)

Surfactant (F-1):

poly(2,2,3,3,4,4,4-heptafluoro-1-isobutyl-1-butyl methacrylate/9-(2,2,2-trifluoro-1-trifluoroethyloxy-carbonyl)-4-oxatricyclo[4.2.1.0$^{3,7}$]nonan-5-on-2-yl methacrylate)

Mw=7,700

Mw/Mn=1.82

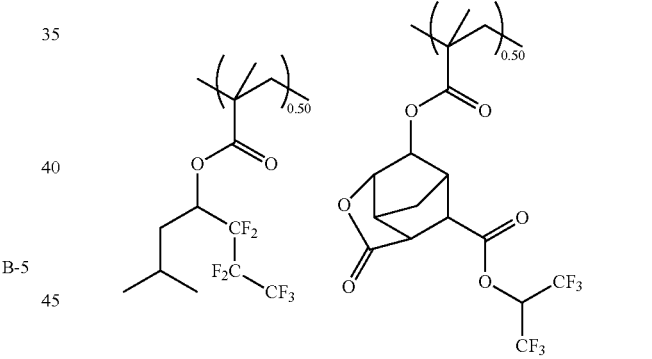

(F-1)

Surfactant A:

3-methyl-3-(2,2,2-trifluoroethoxymethyl)oxetane/tetrahydrofuran/2,2-dimethyl-1,3-propanediol copolymer (Omnova Solutions, Inc.)

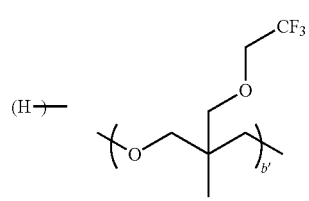

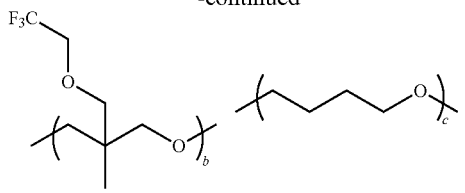

a:(b+b'):(c+c')=1:4-7:0.01-1 (molar ratio)
Mw=1,500

TABLE 4

|  | Resist | Resin (pbw) | PAG (pbw) | Quencher (pbw) | Surfactant (pbw) | Solvent 1 (pbw) | Solvent 2 (pbw) |
|---|---|---|---|---|---|---|---|
| Example 1-1 | R-1 | P-1 (80) | PAG-1 (6.5) | Q-1 (1.7) | F-1 (3.0) | PGMEA (1,728) | GBL (192) |
| 1-2 | R-2 | P-1 (80) | PAG-2 (6.4) | Q-1 (1.7) | F-1 (3.0) | PGMEA (1,728) | GBL (192) |
| 1-3 | R-3 | P-1 (80) | PAG-3 (6.8) | Q-1 (1.7) | F-1 (3.0) | PGMEA (1,728) | GBL (192) |
| 1-4 | R-4 | P-1 (80) | PAG-4 (6.2) | Q-1 (1.7) | F-1 (3.0) | PGMEA (1,728) | GBL (192) |
| 1-5 | R-5 | P-1 (80) | PAG-5 (4.6) PAG-X (3.8) | Q-1 (1.7) | F-1 (3.0) | PGMEA (1,728) | GBL (192) |
| 1-6 | R-6 | P-1 (80) | PAG-6 (4.5) PAG-X (3.8) | Q-1 (1.7) | F-1 (3.0) | PGMEA (1,728) | GBL (192) |
| 1-7 | R-7 | P-2 (80) | PAG-4 (6.2) | Q-1 (1.7) | F-1 (3.0) | PGMEA (1,728) | GBL (192) |
| 1-8 | R-8 | P-3 (80) | PAG-4 (6.2) | Q-1 (1.7) | F-1 (3.0) | PGMEA (1,728) | GBL (192) |
| 1-9 | R-9 | P-4 (80) | PAG-4 (6.2) | Q-1 (1.7) | F-1 (3.0) | PGMEA (1,728) | GBL (192) |
| 1-10 | R-10 | P-5 (80) | PAG-4 (6.2) | Q-1 (1.7) | F-1 (3.0) | PGMEA (1,728) | GBL (192) |
| 1-11 | R-11 | P-6 (80) | PAG-4 (6.2) | Q-1 (1.7) | F-1 (3.0) | PGMEA (1,728) | GBL (192) |
| 1-12 | R-12 | P-7 (80) | PAG-4 (6.2) | Q-1 (1.7) | F-1 (3.0) | PGMEA (1,728) | GBL (192) |
| 1-13 | R-13 | P-8 (80) | PAG-4 (6.2) | Q-1 (1.7) | F-1 (3.0) | PGMEA (1,728) | GBL (192) |
| 1-14 | R-14 | P-9 (80) | PAG-4 (6.2) | Q-1 (1.7) | F-1 (3.0) | PGMEA (1,728) | GBL (192) |
| 1-15 | R-15 | P-10 (80) | PAG-4 (6.2) | Q-1 (1.7) | F-1 (3.0) | PGMEA (1,728) | GBL (192) |
| 1-16 | R-16 | P-11 (80) | PAG-4 (6.2) | Q-1 (1.7) | F-1 (3.0) | PGMEA (1,728) | GBL (192) |
| 1-17 | R-17 | P-12 (80) | PAG-4 (6.2) | Q-1 (1.7) | F-1 (3.0) | PGMEA (1,728) | GBL (192) |
| 1-18 | R-18 | P-1 (80) | PAG-4 (3.1) PAG-X (3.8) | Q-1 (1.7) | F-1 (3.0) | PGMEA (1,728) | GBL (192) |
| 1-19 | R-19 | P-1 (80) | PAG-4 (3.2) PAG-Y (4.8) | Q-1 (1.7) | F-1 (3.0) | PGMEA (1,728) | GBL (192) |
| 1-20 | R-20 | P-1 (80) | PAG-4 (3.1) PAG-Z (3.2) | — | F-1 (3.0) | PGMEA (1,728) | GBL (192) |
| Comparative Example 1-1 | R-21 | P-1 (80) | PAG-X (7.6) | Q-1 (1.7) | F-1 (3.0) | PGMEA (1,728) | GBL (192) |
| 1-2 | R-22 | P-1 (80) | PAG-X (3.2) PAG-Y (4.8) | Q-1 (1.7) | F-1 (3.0) | PGMEA (1,728) | GBL (192) |
| 1-3 | R-23 | P-1 (80) | PAG-X (7.6) PAG-Z (3.2) | — | F-1 (3.0) | PGMEA (1,728) | GBL (192) |
| 1-4 | R-24 | P-2 (80) | PAG-X (7.6) | Q-1 (1.7) | F-1 (3.0) | PGMEA (1,728) | GBL (192) |
| 1-5 | R-25 | P-3 (80) | PAG-X (7.6) | Q-1 (1.7) | F-1 (3.0) | PGMEA (1,728) | GBL (192) |
| 1-6 | R-26 | P-4 (80) | PAG-X (7.6) | Q-1 (1.7) | F-1 (3.0) | PGMEA (1,728) | GBL (192) |
| 1-7 | R-27 | P-5 (80) | PAG-X (7.6) | Q-1 (1.7) | F-1 (3.0) | PGMEA (1,728) | GBL (192) |

Examples 2-1 to 2-20 and Comparative Examples 2-1 to 2-8

Resist Test 1 (ArF Lithography)

On a silicon substrate, an antireflective coating solution (ARC-29A, Nissan Chemical Industries, Ltd.) was coated and baked at 200° C. for 60 seconds to form an ARC of 100 nm thick. Each of the resist solutions shown in Table 4 was spin coated on the silicon substrate and baked on a hot plate at 100° C. for 60 seconds, forming a resist film of 90 nm thick on the ARC. The wafer was exposed on an ArF excimer laser immersion lithography scanner (NSR-S610C by Nikon Corp., NA 1.30, dipole illumination, Cr mask), baked (PEB) at an arbitrary temperature for 60 seconds, and developed in a 2.38 wt % tetramethylammonium hydroxide (TMAH) aqueous solution for 60 seconds, forming a pattern.

Resist evaluation was made on a 40-nm 1:1 line-and-space pattern. On observation under an electron microscope, the optimum exposure dose (Eop) was defined as an exposure dose (mJ/cm$^2$) which provided a line width of 40 nm. The profile of the pattern printed at the optimum dose was compared and judged.

An L/S pattern was formed by exposure in the optimum dose (determined in the sensitivity evaluation) through the mask with the pitch fixed and the line width varied. MEF was calculated from variations of the mask line width and the pattern space width according to the following equation:

MEF=(pattern space width)/(mask line width)−$b$ wherein b is a constant. A value closer to unity (1) indicates better performance.

Further, defects in the pattern as developed were inspected by a flaw detector KLA2800 (KLA-Tencor). A defect density (count/cm$^2$) was computed by dividing the total number of detected defects by a detection area. The pattern formed was an iterated 40-nm 1:1 L/S pattern. The defect inspection conditions included light source UV, inspected pixel size 0.28 µm, and cell-to-cell mode. In this test, the sample was rated good for a defect density of less than 0.05 defect/cm$^2$ and poor for a density of equal to or more than 0.05 defect/cm$^2$.

The collapse limit was a minimum width (nm) of lines which could be resolved without collapse when the line width was reduced by increasing the exposure dose. A smaller value indicates better collapse resistance.

The results of evaluation are shown in Table 5.

TABLE 5

|  | Resist | PEB (°C.) | Eop (mJ/cm²) | MEF | Defect density (count/cm²) | Collapse limit (nm) |
|---|---|---|---|---|---|---|
| Example 2-1 | R-1 | 90 | 26 | 2.5 | 0.03 | 30 |
| 2-2 | R-2 | 90 | 30 | 2.4 | 0.03 | 30 |
| 2-3 | R-3 | 90 | 29 | 2.1 | 0.04 | 29 |
| 2-4 | R-4 | 90 | 27 | 2.2 | 0.03 | 28 |
| 2-5 | R-5 | 90 | 29 | 2.3 | 0.03 | 30 |
| 2-6 | R-6 | 95 | 32 | 2.1 | 0.04 | 30 |
| 2-7 | R-7 | 90 | 27 | 2.3 | 0.05 | 29 |
| 2-8 | R-8 | 90 | 27 | 2.3 | 0.05 | 28 |
| 2-9 | R-9 | 90 | 28 | 2.2 | 0.04 | 30 |
| 2-10 | R-10 | 90 | 28 | 2.2 | 0.04 | 29 |
| 2-11 | R-11 | 95 | 30 | 2.1 | 0.04 | 28 |
| 2-12 | R-12 | 95 | 30 | 2.2 | 0.04 | 28 |
| 2-13 | R-13 | 90 | 28 | 2.2 | 0.05 | 31 |
| 2-14 | R-14 | 90 | 27 | 2.3 | 0.04 | 29 |
| 2-15 | R-15 | 95 | 32 | 2.1 | 0.04 | 30 |
| 2-16 | R-16 | 95 | 33 | 2.4 | 0.05 | 29 |
| 2-17 | R-17 | 85 | 26 | 2.6 | 0.04 | 32 |
| 2-18 | R-18 | 90 | 28 | 2.3 | 0.03 | 30 |
| 2-19 | R-19 | 95 | 33 | 2.2 | 0.03 | 28 |
| 2-20 | R-20 | 95 | 32 | 2.4 | 0.03 | 30 |
| Comparative Example 2-1 | R-21 | 90 | 36 | 4.0 | 0.06 | 38 |
| 2-2 | R-22 | 95 | 38 | 3.8 | 0.07 | 34 |
| 2-3 | R-23 | 95 | 39 | 4.2 | 0.07 | 35 |
| 2-4 | R-24 | 90 | 40 | 4.1 | 0.06 | 36 |
| 2-5 | R-25 | 90 | 38 | 4.2 | 0.06 | 36 |
| 2-6 | R-26 | 90 | 39 | 3.9 | 0.06 | 38 |
| 2-7 | R-27 | 90 | 39 | 4.0 | 0.07 | 40 |
| 2-8 | R-21 | 85 | 48 | 3.2 | 0.086 | 34 |

As seen from the results of Table 5, the resist compositions within the scope of the invention offer advantages including high resolution, satisfactory pattern profile, improved MEF, and minimal defects, and are suited as resist material for ArF immersion lithography.

In Comparative Example 2-8, the PEB temperature is set relatively low to suppress acid diffusion. As a result, MEF is improved at the sacrifice of sensitivity. In contrast, use of the inventive PAG ensures to improve MEF without lowering sensitivity.

Examples 3-1 to 3-20 and Comparative Examples 3-1 to 3-8

Resist Test 2 (ArF Lithography)

On a substrate, a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition in Table 4 was spin coated, then baked on a hot plate at 100° C. for 60 seconds to form a resist film of 100 nm thick. Using an ArF excimer laser immersion lithography scanner NSR-610C (Nikon Corp., NA 1.30, σ 0.98/0.78, 4/5 annular illumination), pattern exposure was performed through Mask A or B described below.

Mask A is a 6% halftone phase shift mask bearing a line pattern with a pitch of 100 nm and a line width of 50 nm (on-wafer size). After exposure through Mask A, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask A were dissolved in the developer, that is, image reversal took place to form a line-and-space (L/S) pattern with a space width of 50 nm and a pitch of 100 nm.

Mask B is a 6% halftone phase shift mask bearing a line pattern with a pitch of 200 nm and a line width of 45 nm (on-wafer size). After exposure through Mask B, the wafer was baked (PEB) for 60 seconds and developed. Specifically, butyl acetate was injected from a development nozzle while the wafer was spun at 30 rpm for 3 seconds, which was followed by stationary puddle development for 27 seconds. As a result, the unexposed regions which had been masked with Mask B were dissolved in the developer, that is, image reversal took place to form an isolated space pattern (referred to as "trench pattern", hereinafter) with a space width of 45 nm and a pitch of 200 nm.

[Evaluation of Sensitivity]

As an index of sensitivity, the optimum dose (Eop, mJ/cm²) which provided an L/S pattern with a space width of 50 nm and a pitch of 100 nm on exposure through Mask A was determined.

[Evaluation of Mask Error Factor (MEF)]

An L/S pattern was formed by exposure in the optimum dose (determined in the sensitivity evaluation) through Mask A with the pitch fixed and the line width varied. MEF was calculated from variations of the mask line width and the pattern space width according to the following equation:

$$MEF = (\text{pattern space width})/(\text{mask line width}) - b$$

wherein b is a constant. A value closer to unity (1) indicates better performance.

[Evaluation of Depth-of-Focus (DOF) Margin]

The exposure dose and DOF which ensured to form a trench pattern with a space width of 35 nm on exposure through Mask B were defined as the optimum exposure dose and the optimum DOF, respectively. The depth (μm) over which focus was changed that could form a resist pattern with a space width of 35 nm±10% (i.e., 31.5 nm to 38.5 nm) was determined and reported as DOF. A larger value indicates a smaller change of pattern size with a change of DOF and hence, better DOF margin.

The results are shown in Table 6.

TABLE 6

|  |  | Resist | PEB (°C.) | Eop (mJ/cm²) | MEF | DOF (nm) |
|---|---|---|---|---|---|---|
| Example | 3-1 | R-1 | 90 | 29 | 2.4 | 140 |
|  | 3-2 | R-2 | 90 | 32 | 2.4 | 130 |
|  | 3-3 | R-3 | 90 | 31 | 2.2 | 140 |
|  | 3-4 | R-4 | 90 | 28 | 2.2 | 140 |
|  | 3-5 | R-5 | 90 | 30 | 2.4 | 130 |
|  | 3-6 | R-6 | 95 | 34 | 2.2 | 130 |
|  | 3-7 | R-7 | 90 | 29 | 2.4 | 140 |
|  | 3-8 | R-8 | 90 | 30 | 2.3 | 140 |
|  | 3-9 | R-9 | 90 | 30 | 2.3 | 150 |
|  | 3-10 | R-10 | 90 | 31 | 2.2 | 140 |
|  | 3-11 | R-11 | 95 | 32 | 2.3 | 150 |
|  | 3-12 | R-12 | 95 | 33 | 2.1 | 140 |
|  | 3-13 | R-13 | 90 | 30 | 2.1 | 140 |
|  | 3-14 | R-14 | 90 | 29 | 2.2 | 140 |
|  | 3-15 | R-15 | 95 | 35 | 2.1 | 120 |
|  | 3-16 | R-16 | 95 | 36 | 2.3 | 120 |
|  | 3-17 | R-17 | 85 | 26 | 2.7 | 140 |
|  | 3-18 | R-18 | 90 | 29 | 2.4 | 130 |
|  | 3-19 | R-19 | 95 | 34 | 2.3 | 150 |
|  | 3-20 | R-20 | 95 | 34 | 2.2 | 140 |
| Comparative Example | 3-1 | R-21 | 90 | 40 | 3.8 | 100 |
|  | 3-2 | R-22 | 95 | 42 | 3.7 | 100 |
|  | 3-3 | R-23 | 95 | 43 | 4.0 | 90 |
|  | 3-4 | R-24 | 90 | 42 | 4.1 | 100 |
|  | 3-5 | R-25 | 90 | 42 | 4.3 | 90 |
|  | 3-6 | R-26 | 90 | 43 | 3.9 | 90 |

TABLE 6-continued

| | Resist | PEB (° C.) | Eop (mJ/cm²) | MEF | DOF (nm) |
|---|---|---|---|---|---|
| 3-7 | R-27 | 90 | 44 | 4.1 | 100 |
| 3-8 | R-21 | 85 | 52 | 3.0 | 100 |

As seen from the results of Table 6, the resist compositions within the scope of the invention form negative patterns via organic solvent development with the advantages of improved MEF without a concomitant drop of sensitivity, and improved DOF margin of trench patterns. The compositions are advantageously applicable to the organic solvent development process.

While the invention has been illustrated and described in typical embodiments, it is not intended to be limited to the details shown, since various modifications and substitutions can be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

Japanese Patent Application No. 2014-088137 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A photoacid generator having the general formula (1a):

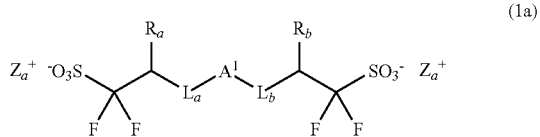

wherein $A^1$ is a straight, branched or cyclic $C_1$-$C_{30}$ divalent hydrocarbon group which may be substituted with or separated by a heteroatom, $L_a$ and $L_b$ are each independently a linking group selected from ether bond, ester bond, sulfonic acid ester bond, carbonate bond, and carbamate bond, $R_a$ and $R_b$ are each independently hydrogen or trifluoromethyl, $Z_a^+$ and $Z_b^+$ are each independently a sulfonium or iodonium cation.

2. The photoacid generator of claim 1, having the structure of the general formula (1b):

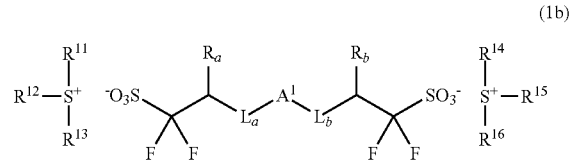

wherein $A^1$, $L_a$, $L_b$, $R_a$ and $R_b$ are as defined above, $R^{11}$, $R^{12}$, $R^{13}$, $R^{14}$, $R^{15}$, and $R^{16}$ are each independently a straight, branched or cyclic $C_1$-$C_{10}$ alkyl or alkenyl group which may be substituted with or separated by a heteroatom, or a $C_6$-$C_{18}$ aryl or aralkyl group which may be substituted with or separated by a heteroatom, any two of $R^{11}$, $R^{12}$ and $R^{13}$ or any two of $R^{14}$, $R^{15}$ and $R^{16}$ may bond together to form a ring with the adjacent sulfur atom.

3. A chemically amplified resist composition comprising a base resin, the photoacid generator of claim 1, and an organic solvent.

4. The resist composition of claim 3 wherein the base resin is a polymer comprising recurring units having the general formula (2) and recurring units having the general formula (3):

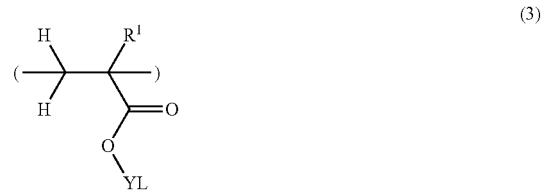

wherein $R^1$ is hydrogen, fluorine, methyl or trifluoromethyl, Z is a single bond, phenylene group, naphthylene group or (backbone)-C(=O)-O-Z'-, Z' is a straight, branched or cyclic $C_1$-$C_{10}$ alkylene group which may contain a hydroxyl radical, ether bond, ester bond or lactone ring, or phenylene group or naphthylene group, XA is an acid labile group, and YL is hydrogen or a polar group having at least one structure selected from the group consisting of hydroxyl, cyano, carbonyl, carboxyl, ether bond, ester bond, sulfonic acid ester bond, carbonate bond, lactone ring, sultone ring and carboxylic anhydride.

5. The resist composition of claim 3, further comprising a photoacid generator other than the photoacid generator.

6. The resist composition of claim 3, further comprising a quencher.

7. The resist composition of claim 3, further comprising a surfactant which is insoluble or substantially insoluble in water and soluble in alkaline developer, and/or a surfactant which is insoluble or substantially insoluble in water and alkaline developer.

8. A pattern forming process comprising the steps of applying the chemically amplified resist composition of claim 3 onto a substrate to form a coating, baking, exposing the coating to high-energy radiation, and developing the exposed coating in a developer.

9. The process of claim 8 wherein the exposure step is carried out by immersion lithography using a liquid having a refractive index of at least 1.0 between the resist coating and a projection lens.

10. The process of claim 9, further comprising the step of coating a protective film on the resist coating prior to the exposure step, wherein immersion lithography is carried out while the liquid is held between the protective film and the projection lens.

11. The process of claim 8 wherein the high-energy radiation is KrF excimer laser, ArF excimer laser, electron beam or soft X-ray having a wavelength of 3 to 15 nm.

* * * * *